US012624398B2

(12) United States Patent
Perera et al.

(10) Patent No.: US 12,624,398 B2
(45) Date of Patent: May 12, 2026

(54) USE OF LONG NON-CODING RNAS IN MEDULLOBLASTOMA

(71) Applicant: THE JOHNS HOPKINS UNIVERSITY, Baltimore, MD (US)

(72) Inventors: Joseph Ranjan Perera, St. Petersburg, FL (US); Keisuke Katsushima, Saint Petersburg, FL (US)

(73) Assignee: The Johns Hopkins University, Baltimore, MD (US)

( * ) Notice: Subject to any disclaimer, the term of this patent is extended or adjusted under 35 U.S.C. 154(b) by 910 days.

(21) Appl. No.: 17/642,752

(22) PCT Filed: Sep. 14, 2020

(86) PCT No.: PCT/US2020/050679
§ 371 (c)(1),
(2) Date: Mar. 14, 2022

(87) PCT Pub. No.: WO2021/051063
PCT Pub. Date: Mar. 18, 2021

(65) Prior Publication Data
US 2022/0325358 A1 Oct. 13, 2022

Related U.S. Application Data

(60) Provisional application No. 62/938,526, filed on Nov. 21, 2019, provisional application No. 62/899,619, filed on Sep. 12, 2019.

(51) Int. Cl.
| *C12Q 1/68* | (2018.01) |
| *C12Q 1/6886* | (2018.01) |
| *C12Q 1/6841* | (2018.01) |

(52) U.S. Cl.
CPC ......... *C12Q 1/6886* (2013.01); *C12Q 1/6841* (2013.01); *C12Q 2600/158* (2013.01); *C12Q 2600/178* (2013.01)

(58) Field of Classification Search
CPC ................ C12Q 1/6886; C12Q 1/6841; C12Q 2600/158; C12Q 2600/178
See application file for complete search history.

(56) References Cited

PUBLICATIONS

ICGC Dataset (Accession No. EGAS00001000215, 1969) (Year: 1969).*
Aldosari (Aldosari et al.; Arch Pathol Lab Med, vol. 126, pp. 540-544, May 2002) (Year: 2002).*

* cited by examiner

*Primary Examiner* — Jehanne S Sitton
*Assistant Examiner* — Bailey Buchanan
(74) *Attorney, Agent, or Firm* — Johns Hopkins Technology Ventures

(57) ABSTRACT

The present invention relates to the field of cancer. More specifically, the present invention provides compositions and methods useful for detecting long non-coding RNAs (lncRNA) in medulloblastoma. In one embodiment, the present invention provides a method comprising detecting lnc RNA HLX2-7 in a biological sample obtained from a patient having or suspected of having medulloblastoma. In certain embodiments, detecting step is performed using RNA fluorescence in situ hybridization (FISH) assay. In specific embodiments, the biological sample is a tissue sample. In particular embodiments, the tissue sample is a formalin-fixed paraffin-embedded (FFPE) sample. In a specific embodiment, the FISH assay comprises oligonucleotide probes that hybridize to lncHLX2-7 (SEQ ID NO:200) and branched DNA signal amplification.

32 Claims, 43 Drawing Sheets

Specification includes a Sequence Listing.

$0$ : *E-box (-CACGTG-)*

CTRL    Inc-HLX-2-7

| Diseases or Functions Annotation | p-value | Predicted Activation State | Activation z-score |
|---|---|---|---|
| Cell viability of cerebral cortex cells | 0.00356 | Inhibited | -0.804 |
| Cell viability of cortical neurons | 0.00385 | Inhibited | -0.739 |
| Cell viability of kidney cell lines | 0.00307 | Inhibited | -0.420 | lnc-HLX-2-7    CTRL

| Diseases or Functions Annotation | p-value | Predicted Activation State | Activation z-score |
|---|---|---|---|
| Cell death of osteosarcoma cells | 4.14E-08 | Increased | 3.500 |
| Cell death of cancer cells | 0.000348 | Increased | 2.807 |
| Cell death of tumor cells | 0.000425 | Increased | 2.338 |

FIG. 12B

| Upstream Regulator | MoleculeType | Predicted activation State | Activation z-score |
|---|---|---|---|
| MYCN | transcription regulator | Inhibited | -4.777 |
| MYC | transcription regulator | Inhibited | -4.448 |
| MLXIPL | transcription regulator | Inhibited | -4.264 |
| NFkB (complex) | complex | Inhibited | -2.889 |
| NFE2L2 | transcription regulator | Inhibited | -2.802 |
| 1,2-dithiol-3-thione | chemical reagent | Inhibited | -2.734 |
| KRAS | enzyme | Inhibited | -2.607 |
| HIF1A | transcription regulator | Inhibited | -2.531 |
| PKM | kinase | Inhibited | -2.425 |
| CD40LG | cytokine | Inhibited | -2.423 |
| ESR2 | ligand-dependent nuclear receptor | Inhibited | -2.414 |
| TNF | cytokine | Inhibited | -2.325 |
| EGFR | kinase | Inhibited | -2.093 |
| IL15 | cytokine | Inhibited | -2.030 |

FIG. 12C

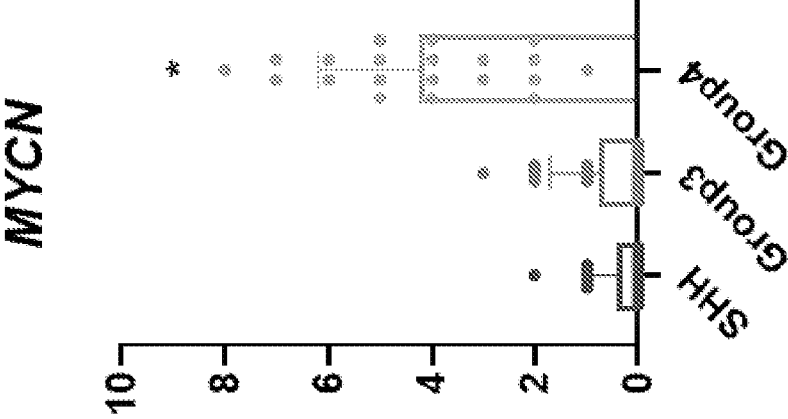
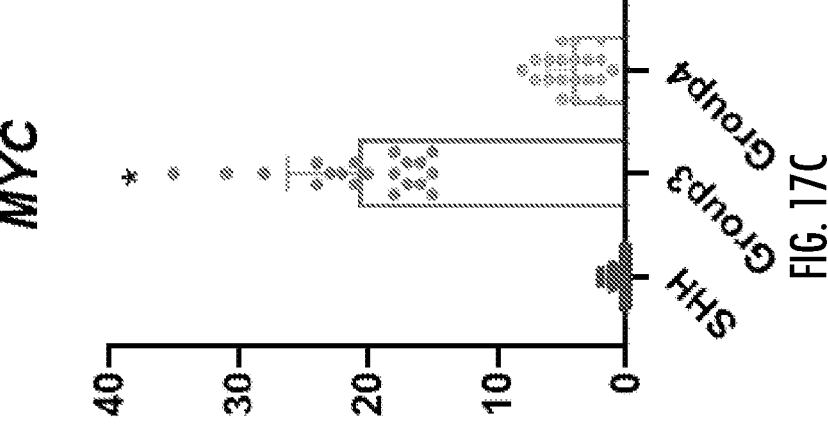
FIG. 17C
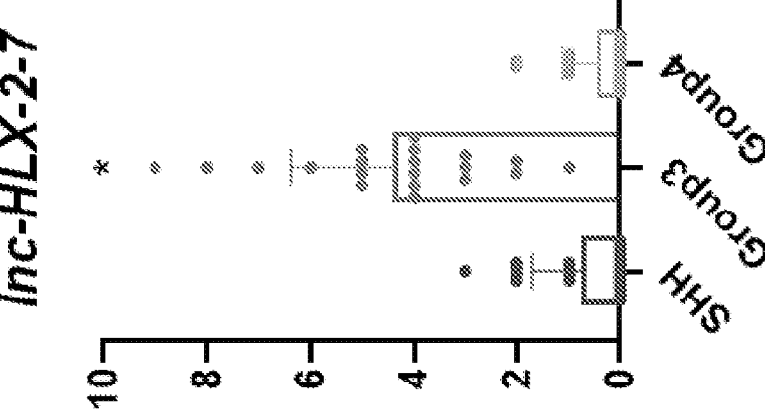

USE OF LONG NON-CODING RNAS IN MEDULLOBLASTOMA

CROSS-REFERENCE TO RELATED APPLICATIONS

This application is a 35 U.S.C. § 371 U.S. national entry of International Application PCT/US2020/050679, having an international filing date of Sep. 14, 2020, which claims the benefit of U.S. Provisional Application No. 62/938,526, filed Nov. 21, 2019, and U.S. Provisional Application 62/899,619, filed Sep. 12, 2019, each of which is incorporated herein by reference in its entirety.

FIELD OF THE INVENTION

The present invention relates to the field of cancer. More specifically, the present invention provides compositions and methods useful for detecting long non-coding RNAs (lncRNA) in medulloblastoma.

INCORPORATION-BY-REFERENCE OF MATERIAL SUBMITTED ELECTRONICALLY

This application contains a sequence listing. It has been submitted electronically via EFS-Web as an ASCII text file entitled "P15814-03_ST25.txt." The sequence listing is 55,637 bytes in size, and was created on Sep. 10, 2020. It is hereby incorporated by reference in its entirety.

BACKGROUND OF THE INVENTION

Medulloblastoma (MB), characterized as WHO group IV, represents the most common and highly malignant pediatric central nervous system tumor, representing 9.2% of all pediatric brain tumor cases and roughly 500 new cases of MB are annually diagnosed. MB are localized in the cerebellum, sharing signatures with embryonic cerebellar lineages, from where they commonly metastasize to other parts of the brain and spinal cord, and, rarely, to extraneural sites. Commonly used treatment strategies for MB, including maximal safe surgical resection, radiotherapy and chemotherapy, are aggressive for patients who are predominantly under 7 years of age. Appropriate treatment therapy selection depends upon clinical subgroup, stage, extent of resection and location, and patient's ability to withstand the treatment. To aide treatment options a combinatorial genome wide sequencing, genetic alteration and DNA methylation approach has improved MB diagnosis into four clinically and molecularly distinct subgroup: wingless (WNT) sonic hedgehog (SHH), group 3 and group 4. Despite these significant advances in early diagnosis and effective treatment approaches, MB remains a deadly disease with around 30% fatality rate. Often eradication of tumor still results in deteriorated overall quality of life due to side effects including organ dysfunction, neurocognitive impairment, endocrine disabilities, and secondary tumors. In addition, even with advances in molecular classification, the defining molecular mechanism remains unknown in group 3 and group 4, making the proper diagnosis and treatment of the respective patient challenging. Hence, there is an urgent need to identify causative molecular mechanism to drive precision medicine based approaches that could improve the quality of life of patients and increase our understanding of MB in general.

SUMMARY OF THE INVENTION

Medulloblastoma (MB) is an aggressive brain tumor that predominantly affects children. Recent high-throughput sequencing studies suggest that the non-coding RNA genome, in particular long non-coding RNAs (lncRNAs), contributes to MB sub-grouping. Here we report the identification of a novel lncRNA, lnc-HLX-2-7, as a potential molecular marker and therapeutic target in group 3 MBs.

Publicly available RNA sequencing (RNA-seq) data from 175 MB patients were interrogated to identify lncRNAs that differentiate between MB subgroups. After characterizing a subset of differentially expressed lncRNAs in vitro and in vivo, the group 3-enriched lncRNA lnc-HLX2-7 was deleted by CRISPR/Cas9 in the MB cell line. Intracranial injected tumors were further characterized by bulk and single-cell RNA-sequencing.

lnc-HLX-2-7 is highly upregulated in group 3 MB cell lines, patient-derived xenografts, and primary MBs compared to other MB sub-groups as assessed by qRT-PCR, RNA-seq, and RNA fluorescence in situ hybridization (FISH). Depletion of lnc-HLX-2-7 significantly reduced cell proliferation and 3D colony formation and induced apoptosis. lnc-HLX-2-7-deleted cells injected into mouse cerebella produced smaller tumors than those derived from parental cells. Pathway analysis revealed that lnc-HLX2-7 modulated oxidative phosphorylation, mitochondrial dysfunction, and sirtuin signaling pathways. The MY C oncogene regulated lnc-HLX-2-7 and the small molecule BET-bromodomain (BRD4) inhibitor JQ1 reduced lnc-HLX2-7 expression.

lnc-HLX-2-7 is oncogenic in MB and represents a promising novel molecular marker and a potential therapeutic target in group 3 MBs.

BRIEF DESCRIPTION OF THE FIGURES

FIG. 1A: Schematic of the identification of group 3-specific lncRNAs in the four MB subgroups (WNT, SHH, group 3 and group 4). FIG. 1B: Top 50 lncRNAs with the highest expression in group 3 MBs compared to other MB subgroups are shown. x-axis indicates p-value (−log 10) of each lncRNA and y-axis indicates fold change value (log 2) of each lncRNA. FIG. 1C: The heat map represents the similarity of expression within group 3 MBs of each lncRNA shown in (B). FIG. 1D: Boxplot showing distribution of normalized expression values of lnc-HLX-1, lnc-HLX-2, lnc-HLX-5, and lnc-HLX-6 in WNT, SHH, group 3 and group 4 MBs. Dots represent the expression value for each MB patient. *p<0.01, Kruskal-Wallis analysis. FIG. 1E-1F: qRT-PCR analysis showing the distribution of normalized expression values of lnc-HLX-2-7 in MB cell lines (FIG. 1E) and PDX samples (FIG. 1F) of group 3, group 4, and SSH MBs. Values indicate fold change relative to cerebellum.

FIG. 2A: Expression level of lnc-HLX-2-7 in D425 Med and MED211 cells treated with ASO against the genes indicated on the x-axis. Relative expression level to mock (non-transfected) is indicated on the y-axis. *p<0.01, Kruskal-Wallis analysis. Viable cell numbers (FIG. 2B) and apoptotic cell numbers (FIG. 2C) in D425 Med and MED211 cells treated with either ASO-luc or ASO-lnc-HLX-2-7. Relative value to mock is indicated on the y-axis. *p<0.01, Kruskal-Wallis analysis. FIG. 2D: Expression level of lnc-HLX-2-7 in D425 Med and MED211 control (CTRL) and D425 Med and MED211-lnc-HLX-2-7-sgRNA (lnc-HLX-2-7) cells. Relative expression level to CTRL is indicated on the y-axis. *p<0.01, Student's t-test. FIG. 2E: Cell viability assays performed with D425 Med and MED211 control (CTRL)

and D425 Med and MED211-lnc-HLX-2-7-sgRNA (lnc-HLX-2-7) cells. Points represent the mean and standard deviation of three biological replicates. *p<0.01, Student's t-test. FIG. 2F: Colony formation assays performed with D425 Med and MED211 control (CTRL) and D425 Med and MED211-lnc-HLX-2-7-sgRNA (lnc-HLX-2-7) cells. Three independent experiments were performed, and data are presented as mean±SD. *p<0.01, Student's t-test.

FIG. 3A: D425 Med and MED211 control (CTRL) and D425 Med- and MED211-lnc-HLX-2-7-sgRNA (lnc-HLX-2-7) cells expressing luciferase were implanted into the right forebrains of NOD-SCID mice, and tumor formation was assessed by bioluminescence imaging. Changes in bioluminescent signal were examined weekly after tumor implantation. FIG. 3B: Quantification of total photon counts from mice implanted with D425 Med and MED211 control (CTRL) and D425 Med- and MED211-lnc-HLX-2-7-sgRNA (lnc-HLX-2-7) cells. n=9, *p<0.05, Student's t-test. FIG. 3C: Ki67 and (D) TUNEL staining of xenograft tumors. Nuclei are stained with DAPI. Scale bars, 50 μm. Quantification of Ki67 and TUNEL-positive cells were shown. *p<0.05, Student's t-test. FIG. 3E: Overall survival was determined by Kaplan-Meier analysis, and the log-rank test was applied to assess the differences between groups. *p<0.05, Mantel-Cox log-rank test.

FIG. 4A: Expression levels of MYC and lnc-HLX-2-7 in D425 Med and MED211 cells treated with siRNA against the indicated genes on the x-axis. Relative expression level to mock (non-transfected) is indicated on the y-axis. *p<0.01, Kruskal-Wallis analysis. FIG. 4B: Schematic diagram showing E-box motifs around the TSS of lnc-HLX-2-7. Open circles indicate E-box motifs. Arrows show the primer location of ChIP-qPCR. FIG. 4C: Enrichment of MYC in the lnc-HLX-2-7 promoter regions in DAOY, D425 Med, and MED211 cells. Enrichment is expressed as a percentage of input DNA. *p<0.01, Student's t-test. FIG. 4D: Expression level of MYC and lnc-HLX-2-7 in D425 Med, and MED211 cells treated with JQ1. Values are indicated relative to abundance in DMSO-treated cells. *p<0.01, Kruskal-Wallis analysis.

FIG. 5A: Heatmap representation of genes up and downregulated after lnc-HLX2-7 depletion in D425 xenografts. FIG. 5B: Molecular and cellular functions and diseases associated with these genes. FIG. 5C: IPA Canonical Pathway analysis was performed to predict signaling pathway activity. The 10 most significant pathways with lowest p-values are presented. FIG. 5D: Uniform Manifold Approximation and Projection (UMAP) plot of transcriptionally distinct cell populations from aggregate CTRL and lnc-HLX-2-7-deleted xenograft scRNA-seq samples. Five distinct clusters (1-5) were identified. FIG. 5E: UMAP plot with CTRL and lnc-HLX-2-7-deleted xenograft samples highlighted. Bar chart indicates the percentage of cells from each xenograft sample for the clusters corresponding to FIG. 5D. FIG. 5F: IPA Canonical Pathway analysis to predict signaling pathway activity in clusters 1, 2, 3, 4, and 5. The top canonical pathways with lowest adjusted p-values are shown. FIG. 5G: Pseudotemporal trajectory of cells from CTRL to lnc-HLX-2-7-deleted cells. Numbered circle with white background denotes the root node selected for pseudotemporal ordering, black circles represent branch nodes (where cells can proceed to different outcomes), and gray circles indicate different outcomes. The red trajectory denotes the structure of pseudotime graph. Cell colors denote the progression of cells along pseudotime.

FIG. 6A: Representative RNA-FISH analysis of lnc-HLX-2-7 and MYC in MB tissues. RNA-FISH analysis of lnc-HLX-2-7 and MYC in group 3 MB patients (upper panels) and group 4 MB patients (lower panels). FIG. 6B: Representative RNA-FISH analysis of lnc-HLX-2-7 and MYCN in MB tissues. RNA-FISH analysis of lnc-HLX-2-7 and MYCN in group 3 MB patients (upper panels) and group 4 MB patients (lower panels). Nuclei are stained with DAPI. Scale bars, 10 μm. FIG. 6C: The spot numbers relating to lnc-HLX-2-7, MYC, and MY CN were quantified per cell in group 3 and group 4 MB patients. n=20, *p<0.01, Student's t-test. FIG. 6D: Correlation between lnc-HLX-2-7 and MYC expression in group 3 MB patients. n=20, *p<0.01, Pearson correlation coefficient. FIG. 6E: Kaplan-Meier survival curves of group 3 MB patients according to lnc-HLX-2-7 and MYC expression. n=10, *p<0.01, log-rank test.

FIG. 7A: lnc-HLX-2-7 is a 517 bp intronic lncRNA encoded within the HLX gene located 2300 bp downstream of the HLX gene. The fourth and the fifth exons of the lnc-HLX-2-7 are repeated elements. The first exon has a 32 bp repeat at its end, while the second and third exons are non-repeated. FIG. 7B: lnc-HLX-2 contains 11 transcripts (lnc-HLX-2-1 to lnc-HLX-2-11). FIG. 7C: Boxplot showing distribution of normalized expression values of 11 transcripts (lnc-HLX-2-1 to lnc-HLX-2-11) of lnc-HLX-2 in group 3 MBs. *p<0.01, Kruskal-Wallis analysis. FIG. 7D: Boxplot showing distribution of normalized expression values of lnc-HLX-2-7 in the eight molecular subtypes of group 3 and group 4 MB. Dots represent the expression value for each MB patient. *p<0.01, Kruskal-Wallis analysis.

FIG. 9A: Expression levels of HLX in D425 Med and MED211 cells treated with siRNA against the indicated genes in the x-axis. FIG. 9B: Viable cell numbers in D425 Med and MED211 cells treated with either si-NC or si-HLX. Relative value to mock is indicated in the y-axis. *p<0.01, Kruskal-Wallis analysis.

FIG. 10A: D425 Med and MED211 cells expressing luciferase were implanted into the right forebrains of NOD-SCID mice. Seven days after injection, mice were administered DMSO or JQ1. Tumor formation was assessed by bioluminescence imaging. Changes in bioluminescent signal were examined weekly after tumor implantation. FIG. 10B: Quantification of total photon counts from mice treated with JQ1 or DMSO. n=4, *p<0.05, Student's t-test. FIG. 10C: Expression levels of MY C and lnc-HLX-2-7 were examined by qPCR in DMSO or JQ1-treated mouse xenografts. Relative expression levels compared to those in the DMSO-treated tumor are indicated on the y-axis (n=4). Error bars indicate s.e.m. n=4, *p<0.01, Student's t-test.

FIG. 11A: Expression levels of lnc-HLX-2-7 in pcDNA4 or pcDNA4-lnc-HLX-2-7-expressing D425 Med and MED211 cells treated with JQ1. Relative value to pcDNA4 is indicated in the y-axis. *p<0.01, Student's t-test. FIG. 11B-11C: Viable cell numbers (FIG. 11B) and expression level of MYC (FIG. 11C) in pcDNA4 or pcDNA4-lnc-HLX-2-7-expressing D425 Med and MED211 cells treated with JQ1. Relative value to DMSO is indicated in the y-axis. *p<0.01, Kruskal-Wallis analysis.

FIG. 12A-12C. lnc-HLX2-7 interacting pathway genes in D425 Med cells. FIG. 12A: Heatmap representation of genes up- and downregulated after lnc-HLX2-7 depletion in D425 Med cells (p<0.05). FIG. 12B: Molecular and cellular functions and diseases associated with these genes. FIG. 12C: The most significant upstream regulators inhibited by depletion of lnc-HLX-2-7.

FIG. 16A: Representation of RNA-FISH analysis of lnc-HLX-2-7 and MYC in MB tissues. RNA-FISH analysis of lnc-HLX-2-7 and MYC in normal mouse brains (upper panels) and D425 Med xenografts (lower panels). Nuclei are stained with DAPI. Scale bars, 10 μm. FIG. 16B: The spot numbers relating to lnc-HLX-2-7 and MYC were quantified per cell in normal mouse brain and D425 Med xenograft. *p<0.01.

FIG. 17A-17C. RNA-FISH confirms that lnc-HLX-2-7 is not expressed in SHH MB patients. RNA-FISH analysis of lnc-HLX-2-7 and MY C (FIG. 17A) or MY CN (FIG. 17B) in SHH MB tissues. Nuclei are stained with DAPI. Scale bars, 10 μm. FIG. 17C: The spot numbers relating to lnc-HLX-2-7, MYC, and MYCN were quantified per cell in Group 3, Group 4, and SHH MB patients. n=20, *p<0.01.

DETAILED DESCRIPTION OF THE INVENTION

Figure 1A:
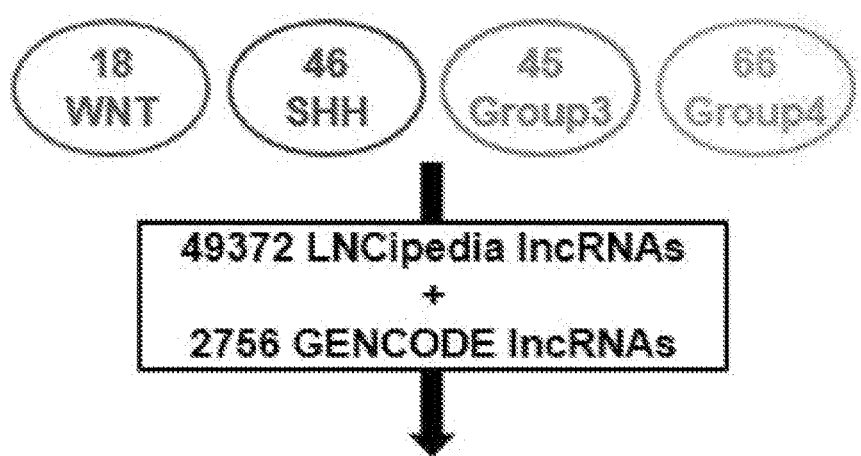
FIG. 1A-F. Identification and validation of the group 3-specific lncRNA, lnc-HLX-2-7.
Figure 1B:
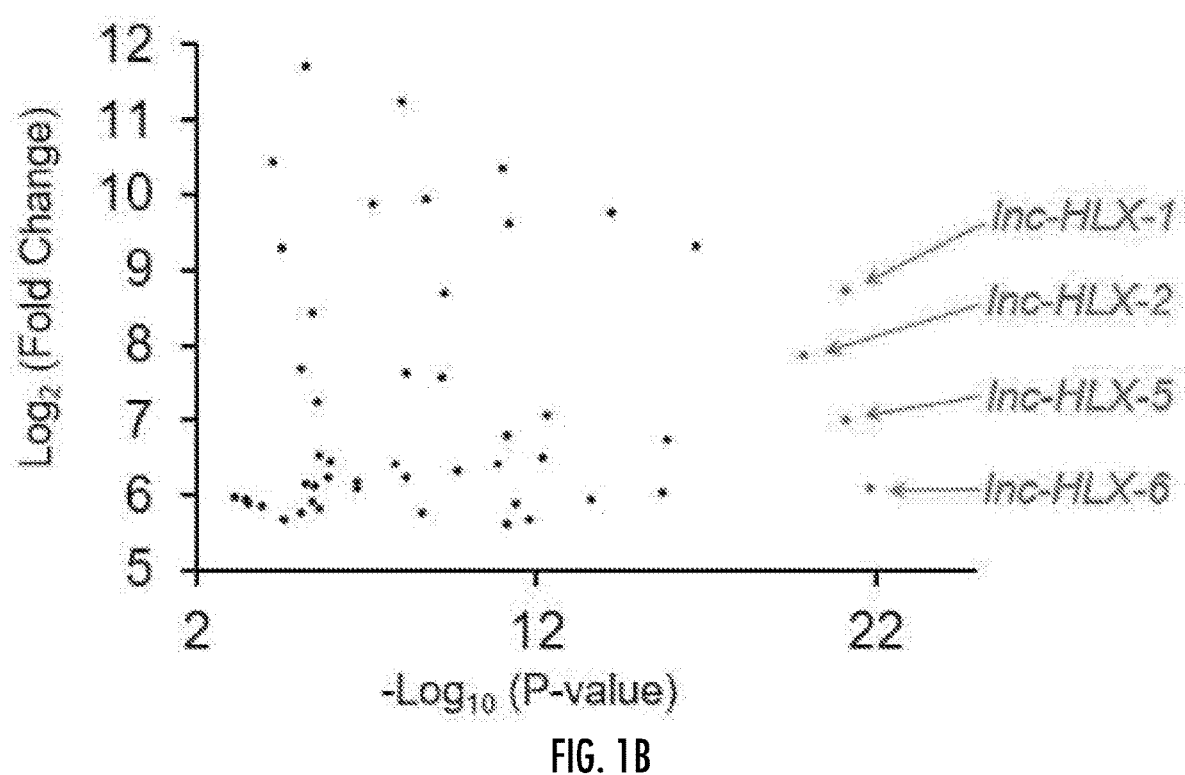

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Accordingly, in one aspect, the present invention provides methods and compositions useful for detecting long non-coding (lnc) RNAs. In one embodiment, the present invention provides a method comprising detecting lnc RNA HLX2-7 in a biological sample obtained from a patient having or suspected of having medulloblastoma. In certain embodiments, detecting step is performed using RNA fluorescence in situ hybridization (FISH) assay. In specific embodiments, the biological sample is a tissue sample. In particular embodiments, the tissue sample is a formalin-fixed paraffin-embedded (FFPE) sample. In a specific embodiment, the FISH assay comprises oligonucleotide probes that hybridize to lncHLX2-7 (SEQ ID NO:200) and branched DNA signal amplification. In a more specific embodiment, the probes comprise at least one of SEQ ID NOS:3-4 and 8-21. In an alternative embodiment, the probes comprise SEQ ID NOS:3-4 and 8-21. In another embodiment, the probes further comprise at least one of SEQ ID NOS:5-7. In yet another embodiment, the probes further comprise SEQ ID NOS:5-7.

In another embodiment, the method further comprises detecting MYC expression in the biological sample. In specific embodiments, the biological sample is a tissue sample. In particular embodiments, the tissue sample is a formalin-fixed paraffin-embedded (FFPE) sample. In a specific embodiment, the FISH assay comprises oligonucleotide probes that hybridize to MYC (SEQ ID NO:202) and branched DNA signal amplification. In a more specific embodiment, the probes comprise at least one of SEQ ID NOS:51-56, 59-60, 62-63, 66-69, 72-73, 75-78, 81-98, 101-102. In a range of 'n' probes where 'n' is the total number of listed probes, the term "at least one of" includes the terms at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 . . . up to and including n probes.

In an alternative embodiment, the probes comprise SEQ ID NOS:51-56, 59-60, 62-63, 66-69, 72-73, 75-78, 81-98, 101-102. In another embodiment, the probes further comprise at least one of SEQ ID NOS:57-58, 61, 64-65, 70-71, 74, 79-80, 99-100. In yet another embodiment, the probes further comprise SEQ ID NOS:57-58, 61, 64-65, 70-71, 74, 79-80, 99-100.

In embodiments detecting HLX2-7 and/or MYC expression, the method can further comprise detecting lnc RNA SPRY4-IT1 in the biological sample. In specific embodiments, the biological sample is a tissue sample. In particular embodiments, the tissue sample is a formalin-fixed paraffin-embedded (FFPE) sample. In a specific embodiment, the FISH assay comprises oligonucleotide probes that hybridize to SPRY4-IT1 (SEQ ID NO:201) and branched DNA signal amplification. In a more specific embodiment, the probes comprise at least one of SEQ ID NOS:22-25 and 27-50. In an alternative embodiment, the probes comprise SEQ ID NOS:22-25 and 27-50. In another embodiment, the probes further comprise SEQ ID NO:26.

In embodiments detecting HLX2-7, MYC and/or SPRY4-IT1 expression, the method can further comprise detecting MYCN in the biological sample. In specific embodiments, the biological sample is a tissue sample. In particular embodiments, the tissue sample is a formalin-fixed paraffin-embedded (FFPE) sample. In a specific embodiment, the FISH assay comprises oligonucleotide probes that hybridize to MYCN (SEQ ID NO:203) and branched DNA signal amplification. In a more specific embodiment, the probes comprise at least one of SEQ ID NOS:103-104, 107-108, 111-112, 114-125, 127-130, 133-144, 147-152. In an alternative embodiment, the probes comprise SEQ ID NOS:103-104, 107-108, 111-112, 114-125, 127-130, 133-144, 147-152. In another embodiment, the probes further comprise at least one of SEQ ID NOS:105-106, 109-110, 113, 126, 131-132, 145-146. In yet another embodiment, the probes further comprise SEQ ID NOS:105-106, 109-110, 113, 126, 131-132, 145-146.

In additional embodiments, the method can further comprise one or more lnc RNA selected from the group consisting of MIR100HG, USP2-AS1, lnc-CFAP100-4, ARHGEF7-AS2, lnc-HLX-1, lnc-EXPH5-2, lnc-CH25H-2, and lnc-TDRP-3. Such lnc RNAs can be used to distinguish Group 3 MB from Group 4 MB.

The compositions and methods of the present invention can be used to differentiate Group 3 MB from Group 4 MB. As described herein, HLX2-7 can be used to differentiate Group 3 MB from Group 4 MB. HLX2-7 is a Group 3 specific lncRNA in MB. In other embodiments, HLX2-7 and MYC can be used together as Group 3 MBs have a higher MYC oncogene expression compared to other MB groups.

In further embodiments, the compositions and methods of the present invention also utilize detection of SPRY4-IT1 ("SPRIGHTLY") and/or MYCN. SPRY4-IT1 is highly expressed primarily in Group 4 MB as compared to other groups. MYCN is also useful as a negative control for Group 3, as expression of MYCN is seen in Group 4.

In another aspect, the present invention provides compositions and methods useful for classifying all MB subgroups. In one embodiment, an 11 lnc RNA panel comprising MIR100HG, lnc-CFAP100-4, ENSG00000279542, lnc-ABCE1-5, USP2-AS1, lnc-RPL12-4, OTX2-AS1, lnc-TBC1D16-3, ENSG00000230393, ENGSG00000260249, and lnc-CCL2-2 is detected. In another embodiment, a 14 lnc RNA panel comprising DPYSL4, HUNK, PDIAS, PYY, CACNA1A, RBM24, KIF26A, DISP3, GABRA5, COL25A1, TENM1, GAD1, ADAMTSL1, and FBXL7 is detected. In an alternative embodiment, a 9 lnc RNA panel comprising MIR100HG, lnc-CFAP100-4, ENSG00000279542, lnc-ABCE1-5, USP2-AS1, lnc- RPL12-4, OTX2-AS1, lnc-TBC1D16-3, and ENSG00000230393 is detected.

In a further aspect, the present invention provides compositions and methods useful for prognosing patients having MB. In one embodiment, a 17 lnc RNA panel comprising lnc-TMEM258-3, ZNRF3-AS1, lnc-TMEM121-3, MAP3K14-AS1, LINC01152, KLF3-AS1, lnc-PRR34-1, lnc-FOXD4L5-25, AC209154.1, TTC28-AS1, FAM222A-AS1, LINC00336, LINC-01551, H19, lnc-RRM2-3, lnc-CDYL-1, and AL139393.2 is detected. See Table 6 which includes favorable prognosis markers and less favorable prognostic markers.

It is understood that in the embodiments in which a panel of lnc RNAs is detected, that the scope of such embodiments includes at least one of the recited panel. In a range of 'n' lnc RNAs where 'n' is the total number of listed lnc RNAs, the term "at least one of" includes the terms at least 1, at least 2, at least 3, at least 4, at least 5, at least 6, at least 7, at least 8, at least 9, at least 10, at least 11, at least 12, at least 13, at least 14, at least 15, at least 16 . . . up to and including at least n lnc RNAs. For example, it is understood that in the 11 lnc RNA panel useful for classifying all MB subgroups, one can utilize at least one of the 11 lnc RNAs and such embodiments include at least 1, at least 2, at least 3, at least 4, at least 5, at least 6, at least 7, at least 8, at least 9, at least 10 and 11 lnc RNAs.

In particular embodiments, the methods of the present invention utilize a FISH assay. In such embodiments, the assay utilizes probe sets for the target RNA and branched DNA signal amplification. For example, a probe set of oligonucleotide pairs hybridizes to the target RNA. Signal amplification is achieve through hybridization of adjacent oligonucleotide pairs to bDNA structured, which are formed by pre-amplifiers, amplifiers and fluorochrome-conjugated label probes. These embodiments result in greater specificity, lower background and higher signal-to-noise ratios. The probes useful for detection of HLX2-7, MYC, SPRY4-IT1, MYCN and MALAT1 (a control) are shown in Tables 1-5, respectively. Such oligos include label extenders and blocker oligos.

In another aspect, the present invention provides compositions and methods useful for detecting HLX2-7, as well as SPRY4-IT1, MYC and/or MYCN in cerebrospinal fluid. In such embodiments, the targets are detected in CSF using polymerase chain reaction including, but not limited to, qPCR and digital PCR.

In yet another aspect, the present invention provides methods of treatment. Such methods can include the detection of HLX2-7, as well as SPRY4-IT1, MYC and/or MYCN, followed by treatment of the patient. Further embodiments include detection of at least one of MIR100HG, USP2-AS1, lnc-CFAP100-4, ARHGEF7-AS2, lnc-HLX-1, lnc-EXPH5-2, lnc-CH25H-2, and lnc-TDRP-3. In still further embodiments, detection can include the lnc RNA panels also described herein. Treatment can include maximal safe surgical resection, radiotherapy and chemotherapy (e.g., cisplatin, cyclophosphamide, vincristine, lomustine, in various dosing regimens; standard dosing is typically 9 cycles, high dose is typically 4 cycles). Combination treatment can be used including, but not limited to, pemetrexed and gemcitabine. Surgery may be needed to treat hydrocephalus (fluid build-up in the skull) and to remove the tumor. Treatment can further include (alone or in combination) endoscopic third ventirculostomy (ETV) or ventriculo-peritoneal shunt (VP shunt). Indeed, the markers described herein can be used to decide whether to reduce radiation, provide a prognosis and reduce chemo exposure In another aspect, lnc-HLX2-7 can be used as a target for therapy. In certain embodiments, expression of lnc-HLX2-7 can be disrupted. Knock out technology can comprise gene editing. For example, gene editing can be performed using a nuclease, including CRISPR associated proteins (Cas proteins, e.g., Cas9), Zinc finger nuclease (ZFN), Transcription Activator-Like Effector Nuclease (TALEN), and meganucleases. In other embodiments, expression of the target can be disrupted using RNA interference technology including, but not limited to, a short interfering RNA (siRNA) molecule, a microRNA (miRNA) molecule, or an antisense molecule.

In a further aspect, the present invention provides one or more probes useful in the methods described herein. In one embodiment, the probes bind HLX2-7 and comprise at least one of SEQ ID NOS:3-21. In another embodiment, the probes bind SPRY4-IT and comprise at least one SEQ ID NOS:22-50.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: The Long Non-Coding RNA lnc-HLX-2-7 is Oncogenic in Group 3 Medulloblastomas Group 3 MBs are associated with poor clinical outcomes, are difficult to subtype clinically, and their biology is poorly understood. In an effort to address these problems, we identified a group 3-specific long non-coding RNA, lnc-HLX-2-7, in an in silico analysis of 175 MBs and confirmed its expression in group 3 MB cell lines, patient-derived xenografts, and formalin-fixed paraffin-embedded (FFPE) samples. Knockdown of lnc-HLX-2-7 significantly reduced cell growth and induced apoptosis. Deletion of lnc-HLX-2-7 in cells injected into mouse cerebellums reduced tumor growth compared to parental cells, and bulk and single-cell RNA-seq of these tumors revealed lnc-HLX-2-7-associated modulation of cell viability, cell death, and energy metabolism signaling pathways. The MYC oncogene regulated lnc-HLX-2-7, and its expression was reduced by JQ1. lnc-HLX-2-7 is a candidate biomarker and a potential therapeutic target in group 3 MBs.

Introduction

Medulloblastoma (MB) is the most common malignant pediatric brain tumor.[1] Recent large-scale and high-throughput analyses have subclassified MBs into four molecularly distinct subgroups, each characterized by specific developmental origins, molecular features, and prognoses.[1-4] The well characterized WNT and SHH subgroups have been causally linked to activated wingless and sonic hedgehog developmental cascades, respectively.[1] However, significant gaps remain in our understanding of the signaling pathways underlying group 3 and group 4 MBs, which account for 60% of all diagnoses and are frequently metastatic at presentation (~40%).[4] Group 3 and group 4 tumors display significant clinical and genetic overlap, including similar location and presence of isochromosome 17q, and identifying these subgroups can be challenging without the application of multi-gene expression or methylation profiling. Therefore, improved understanding of group 3 tumor drivers and theranostic targets is urgently needed.

The vast majority of the genome serves as a template not only for coding RNAs but also non-coding RNAs (ncRNAs). Of the non-coding RNAs, long non-coding RNAs (lncRNAs), which describe a class of RNAs >200 nucleotides in length, have been widely investigated and identified as key regulators of various biological processes including cellular proliferation, differentiation, apoptosis, migration, and invasion.[5-8] LncRNAs are functionally diverse and participate in transcriptional silencing,[9] function as enhancers,[10] and sequester miRNAs from their target sites.[11] LncRNAs can also act as hubs for protein-protein and protein-nucleic acid interactions.[12] There is now a considerable body of evidence implicating lncRNAs in both health and disease, not least human tumorigenesis.[8,13,14] It has recently been reported that various lncRNAs play important roles in MB biology,[2,15-18] although the functional significance of many remains uncertain. Since many lncRNAs are uniquely expressed in specific cancer types,[19] they may function as powerful MB subgroup-specific biomarkers and therapeutic targets.

By analyzing RNA sequencing data derived from human MBs, here we report that the novel lncRNA lnc-HLX-2-7 differentiates group 3 from other MBs. CRISPR/Cas9 deletion of lnc-HLX-2-7 in group 3 MB cells significantly reduced cell growth in vitro and in vivo. RNA sequencing of xenografts revealed lnc-HLX-2-7-associated modulation of cell viability and cell death signaling pathways. lnc-HLX-2-7 is a promising novel biomarker and potential therapeutic target for group 3 MBs.

Materials and Methods

MB tissue and RNA samples. Eighty MB tissue samples obtained from a tumor database maintained by the Department of Pathology at the Johns Hopkins Hospital (JHH) were analyzed (Table 7) under IRB approved protocol NA_00015113. Detailed information about the RNA samples are described in the Supplementary Materials and Methods.

Patient in silico data. Raw FASTQ files for RNA sequencing data corresponding to 175 MB patients (referred to as the ICGC dataset) belonging to the four MB subgroups (accession number EGAS00001000215) were downloaded from the European Genome-Phenome Archive after obtaining Institutional Review Board approval.[20]

Cell culture. Cell lines were authenticated using single tandem repeat profiling. D425 Med cells were cultured in DMEM/F12 with 10% serum and 1% glutamate/penicillin/ streptomycin. MED211 cells were cultured in medium composed of 30% Ham's F12/70% DMEM, 1% antibiotic antimycotic, 20% B27 supplement, 5 µg/mL heparin, 20 ng/mL EGF, and 20 ng/mL FGF2. DAOY cells were cultured in DMEM with 10% serum and 1% glutamate/penicillin/streptomycin. All cells were grown in a humidified incubator at 37° C., 5% $CO_2$. For blocking of BET bromodomain protein in D425 Med and MED211 cells, JQ1 (SML1524-5MG, Sigma Aldrich, St. Louis, MO) was added, and the medium was changed every other day.

Quantitative real-time PCR (qRT-PCR). Total RNA was purified using the Direct-zol RNA Miniprep kit (Zymo Research, Irvine, CA). To obtain RNA from xenografts, tumor tissues were pulverized and then used for purification. Quantitative PCR was carried out using SYBR Green mRNA assays as previously described.[8] Primer sequences are listed in Table 8.

ASO-lnc-HLX2-7. Antisense oligonucleotides (ASOs) were designed using the Integrated DNA Technologies (IDT) Antisense Design Tool (IDT, Coralville, IA). ASO knockdowns were performed with 50 nM (final concentration) locked nucleic acid (LNA) GapmeRs transfected with Lipofectamine 3000 (Thermo Fisher Scientific, Waltham, MA). All ASOs were modified with phosphorothioate (PS) linkages. The following ASOs were used: ASO targeting lnc-HLX-2-7 (ASO-lnc-HLX-2-7): +T*+G*+ A*G*A*G*A*T*T*A*A*T*C*T*A*G*A*T*+T*+G*+C (SEQ ID NO:240) and control ASO targeting luciferase (ASO-Luc): +T*+C*+ G*A*A*G*T*A*C*T*C*A*G*C*G*T*A*A*+G*+T*+T (SEQ ID NO:241). The PS linkages are indicated with * and LNA-modified oligonucleotides are indicated with +.

siRNA-mediated knockdown of HLX, MYC, and MYCN. siRNAs targeting HLX (catalog no. 4427037, ID: s6639) and MYC (catalog no. 4427037, ID: s9129) were purchased from Thermo Fisher Scientific. siRNAs were transfected at 20 nM for 48 h using Lipofectamine RNAiMAX (Thermo Fisher Scientific). The efficiency was determined by qRT-PCR.

Cell proliferation, apoptosis, and 3D colony formation assays. Cells were plated in 96-well plates at $5 \times 10^3$ cells per well in triplicate. After 72 hours of ASO or siRNA transfection, living cells were counted by trypan blue staining. Apoptotic cells were analyzed using a GloMax luminometer (Promega, Fitchburg, WI) with conditions optimized for the Caspase-Glo 3/7 Assay. For the 3D colony formation assay, cells were seeded in 24-well plates at a density of $1 \times 10^2$ cells/well and were stained with crystal violet solution approximately 14 days later. Colony number was determined using the EVE cell counter (Nano Entek, Pleasanton, CA), and staining intensity was analyzed using ImageJ software.

lnc-HLX-2-7 CRISPR/Cas9 knockdown in D425 Med cells. The single guide RNA (sgRNA) targeting lnc-HLX-2-7 was designed using Zhang Lab resources (http://crispr .mit.edu/) and synthesized to make the lenti-lnc-HLX-2-7-sgRNA-Cas9 constructs as described previously.[21] The DNA sequences for generating sgRNA were forward: 5'-GGACCCACTCTCCAACGCAG-3' (SEQ ID NO:1) and reverse: 5'-GCAGGGACCCCTCATTGACG-3' (SEQ ID NO:2). For the control plasmid, no sgRNA sequence was inserted into the construct. Lnc-HLX-2-7-edited cells and control cells were selected using 4 µg/ml puromycin. To determine the genome editing effect, total RNA was extracted from the lnc-HLX-2-7-edited cells and control cells and the expression of lnc-HLX-2-7 quantified by qRT-PCR.

Medulloblastoma xenografts (intracranial). All mouse studies were approved and performed in accordance with the policies and regulations of the Animal Care and Use Committee of Johns Hopkins University. Intracranial MB xenografts were established by injecting D425 Med cells, MED211 cells, D425 Med cells with lnc-HLX-2-7 deleted, and MED211 cells with lnc-HLX-2-7 deleted into the cerebellums of NOD-SCID mice (Jackson Laboratory, Bar Harbor, ME). Cerebellar coordinates were −2 mm from lambda, +1 mm laterally, and 1.5 mm deep. Seven days after injection, mice were administered JQ1 (50 mg/kg) or vehicle alone (DMSO) on alternating days via intraperitoneal injection for 14 days. Tumor growth was evaluated by weekly bioluminescence imaging using an in vivo spectral imaging system (IVIS Lumina II, Xenogen, Alameda, CA).

Immunohistochemistry. For the analysis of cell proliferation, tumor sections were incubated with anti-Ki67 (Alexa Fluor 488 Conjugate) antibodies (#11882, 1:200, Cell Signaling Technology, Danvers, MA) at 4° C. overnight. For the analysis of apoptosis, DeadEnd™ Fluorometric TUNEL System (Promega) was performed on the tumor sections, according to the manufacturer's instructions. The stained sections were imaged using a confocal laser-scanning microscope (Nikon C1 confocal system, Nikon Corp, Tokyo, Japan). The acquired images were processed using the NIS (Nikon) and analyzed with the Image J software (https:// imagej.nih.gov/ij/).

Chromatin immunoprecipitation (ChIP). Cells ($1 \times 10^6$) were treated with 1% formaldehyde for 8 minutes to cross-link histones to DNA. The cell pellets were resuspended in lysis buffer (1% SDS, 10 mmol/L EDTA, 50 mmol/L Tris-HCl pH 8.1, and protease inhibitor) and sonicated using a Covaris 5220 system (Covaris Inc., Woburn, MA). After diluting the cell lysate 1:10 with dilution buffer (1% Triton-X, 2 mmol/L EDTA, 150 mmol/L NaCl, 20 mmol/L Tris-HCl pH 8.1), diluted cell lysates were incubated for 16 h at 4° C. with Dynabeads Protein G (100-03D, Thermo Fisher Scientific) precoated with 5 µL of anti-MYC antibody (ab32, Abcam, Cambridge, UK). ChIP products were analyzed by SYBR Green ChIP-qPCR using the primers listed in Table 9.

RNA library construction and sequencing. Total RNA was prepared from cell lines and orthotopic xenografts using Direct-zol RNA Miniprep kits (Zymo Research, Irvine, CA). RNA quality was determined with the Agilent 2100 Bioanalyzer Nano Assay (Agilent Technologies, Santa Clara, CA). Using a TruSeq Stranded Total RNA library preparation Gold kit (Illumina Inc., San Diego, CA), strand-specific RNA-seq libraries were constructed as per the instructions. The quantification and quality of final libraries were determined using KAPA PCR (Kapa Biosystems, Waltham, MA) and a high-sensitivity DNA chip (Agilent Technologies), respectively. Libraries were sequenced on an Illumina NovaSeq 6000 using 1×50 base paired-end reads. Detailed methods of sequence and data analysis are described in Supplementary Materials and Methods.

Ingenuity pathway analysis (IPA). To analyze pathways affected by lnc-HLX-2-7, differentially expressed genes between D425 Med and D425 Med with lnc-HLX-2-7 deleted were compiled and analyzed using Qiagen's IPA. Analysis was conducted via the IPA web portal.

Data availability. RNA-seq data described in the manuscript is accessible at NCBI GEO accession number GSE151810 and GSE156043, which is expressly incorporated by reference.

RNA-fluorescence in situ hybridization (RNA-FISH). RNA was visualized in paraffin-embedded tissue sections using the QuantiGene ViewRNA ISH Tissue Assay Kit (Affymetrix, Frederick, MD). In brief, tissue sections were rehydrated and incubated with proteinase K. Subsequently, they were incubated with ViewRNA probesets designed against human lnc-HLX-2-7, MYC, and MY CN (Affymetrix, Santa Clara, CA). Custom Type 1 primary probes targeting lnc-HLX-2-7, Type 6 primary probes targeting MYC, and Type 6 primary probes targeting MY CN were designed and synthesized by Affymetrix (Tables 1, 3 and 4). Hybridization was performed according to the manufacturer's instructions.

Statistical analysis. Statistical analyses were performed using GraphPad Prism software and Limma R package. Data are presented as mean±SD of three independent experiments. Differences between two groups were analyzed by the paired Student's t-test and correlations with the Pearson correlation coefficient. Kruskal-Wallis analysis was used to evaluate the differences between more than two groups. Survival analysis was performed using the Kaplan—Meier method and compared using the log-rank test.

Results

Figure 1C:
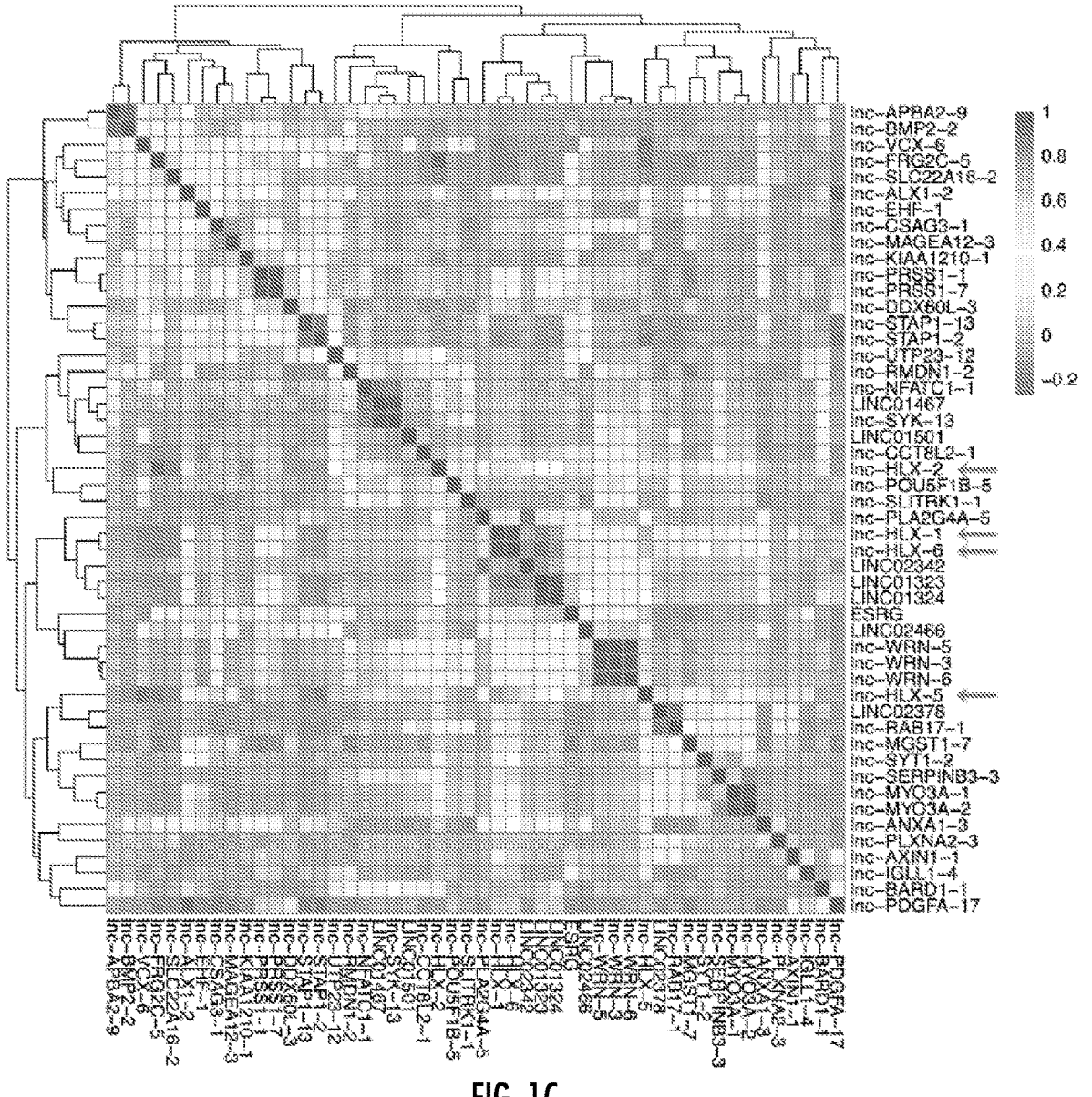
Figure 1D:
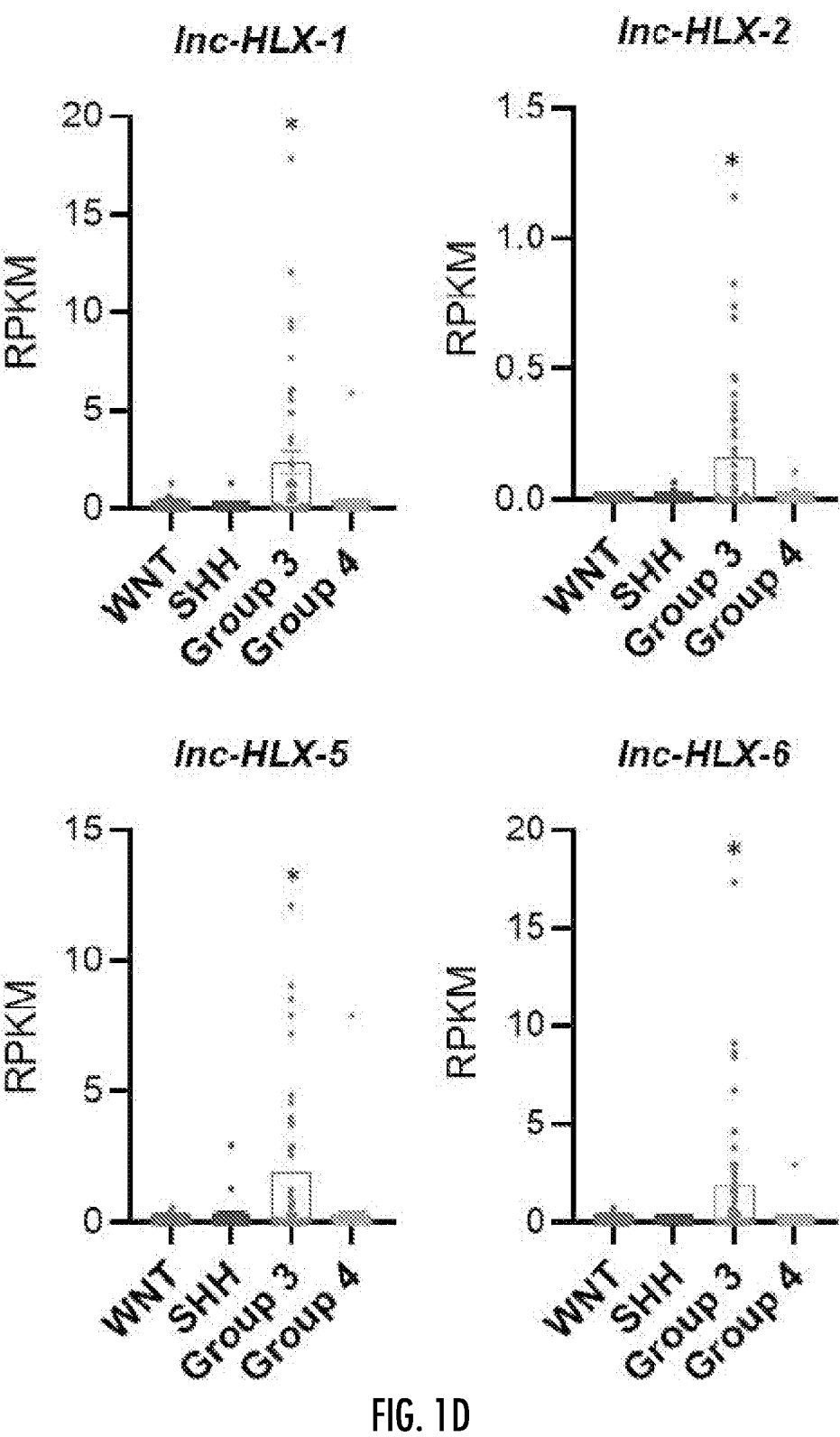
Figure 1E:
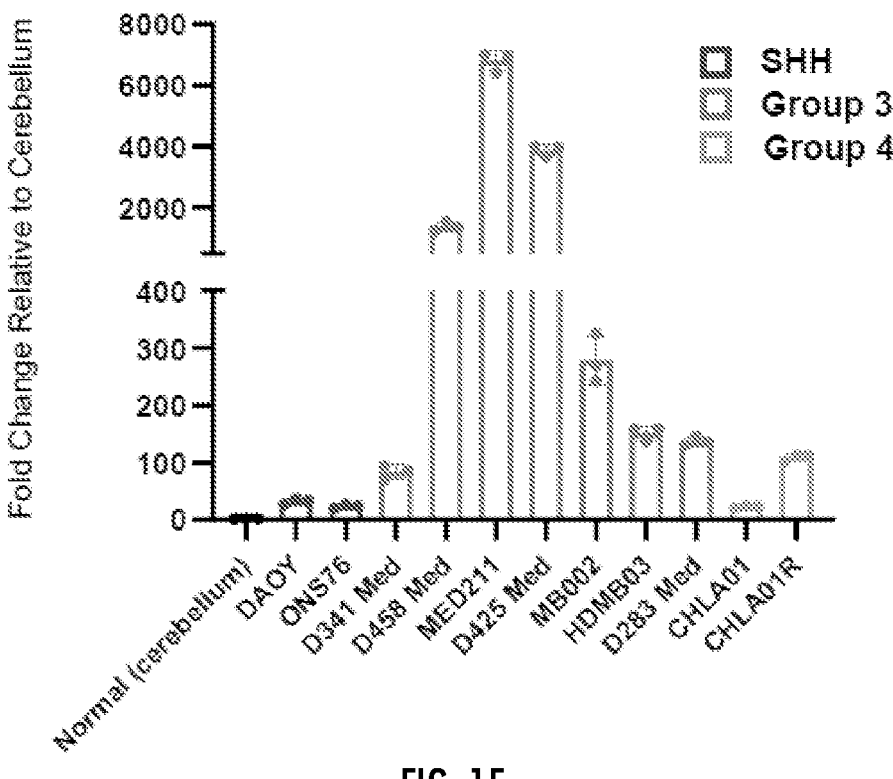
Figure 1F:
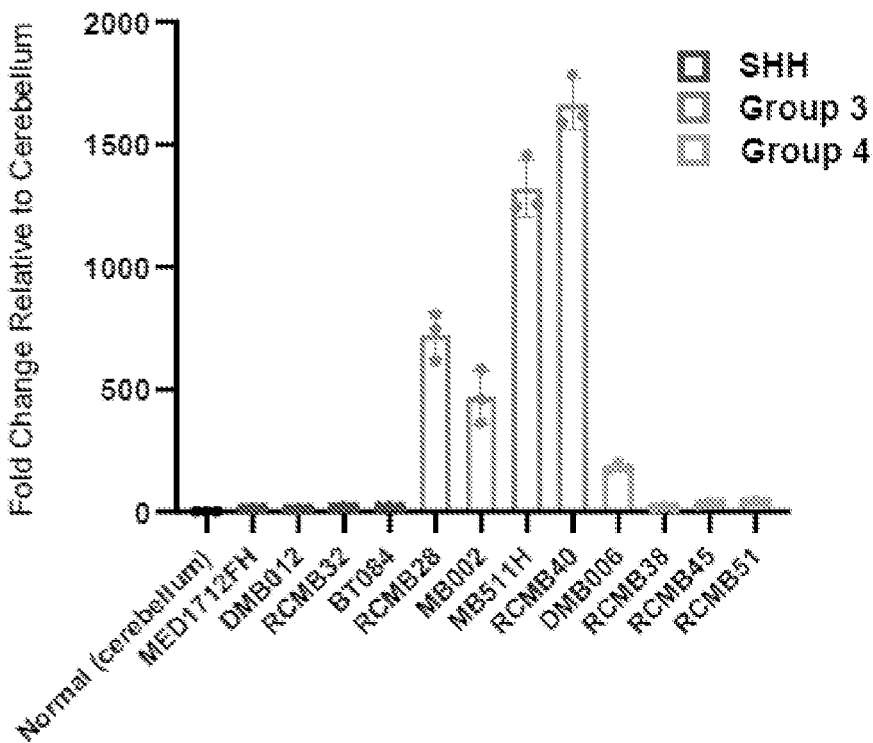
Figure 2C:
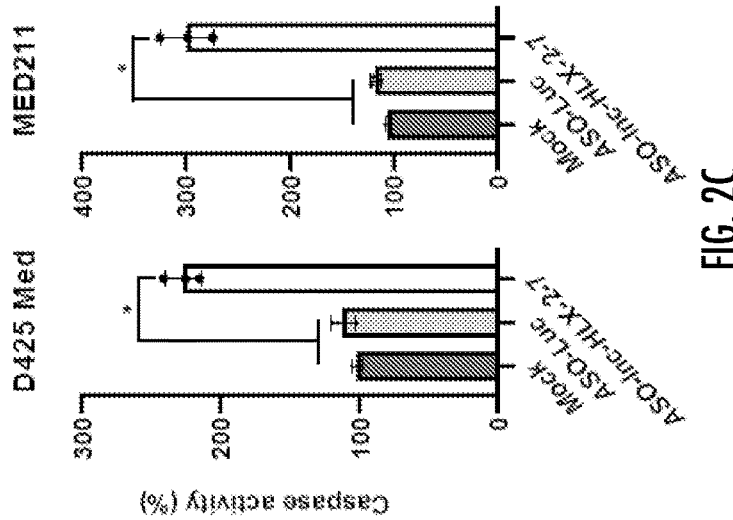
FIG. 2A-2F. Effects of lnc-HLX-2-7 expression on the proliferation and apoptosis of group 3 MB cells.
Figure 2B:
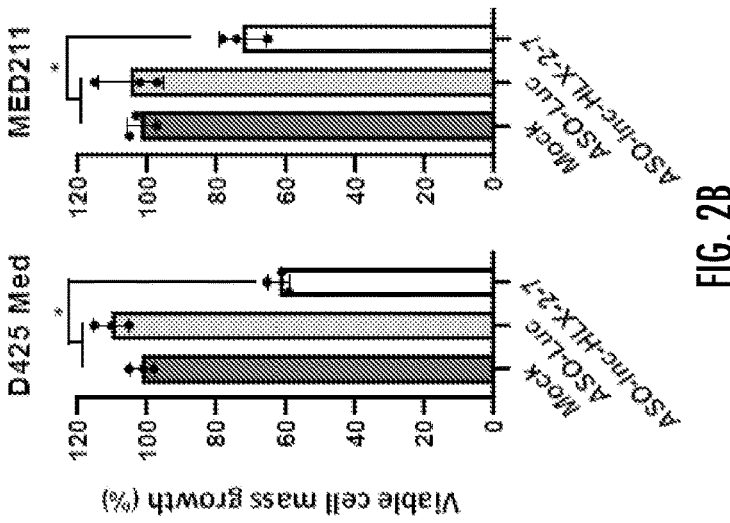
Figure 2A:
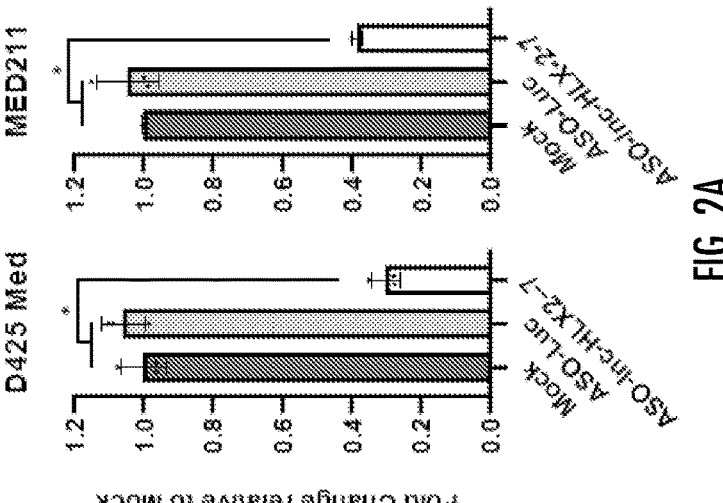
Figure 2D:
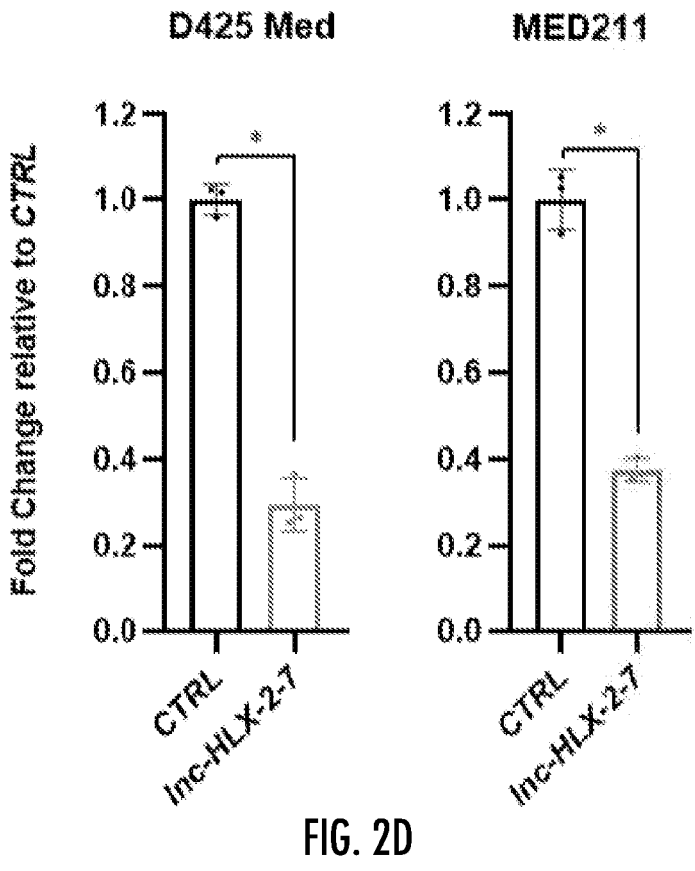
Figure 2E:
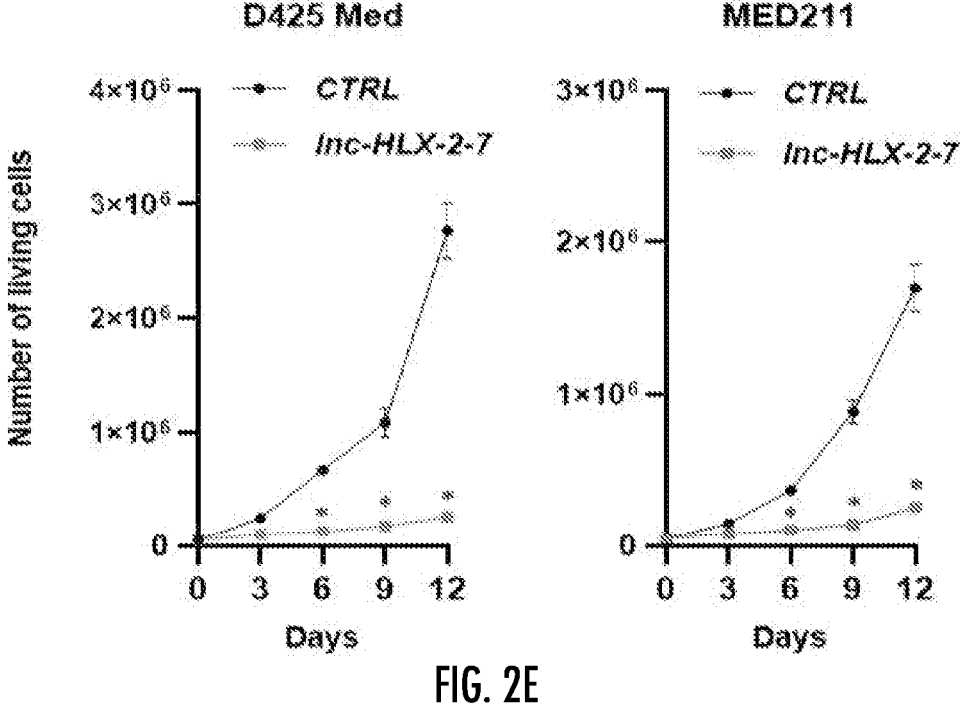
Figure 2F:
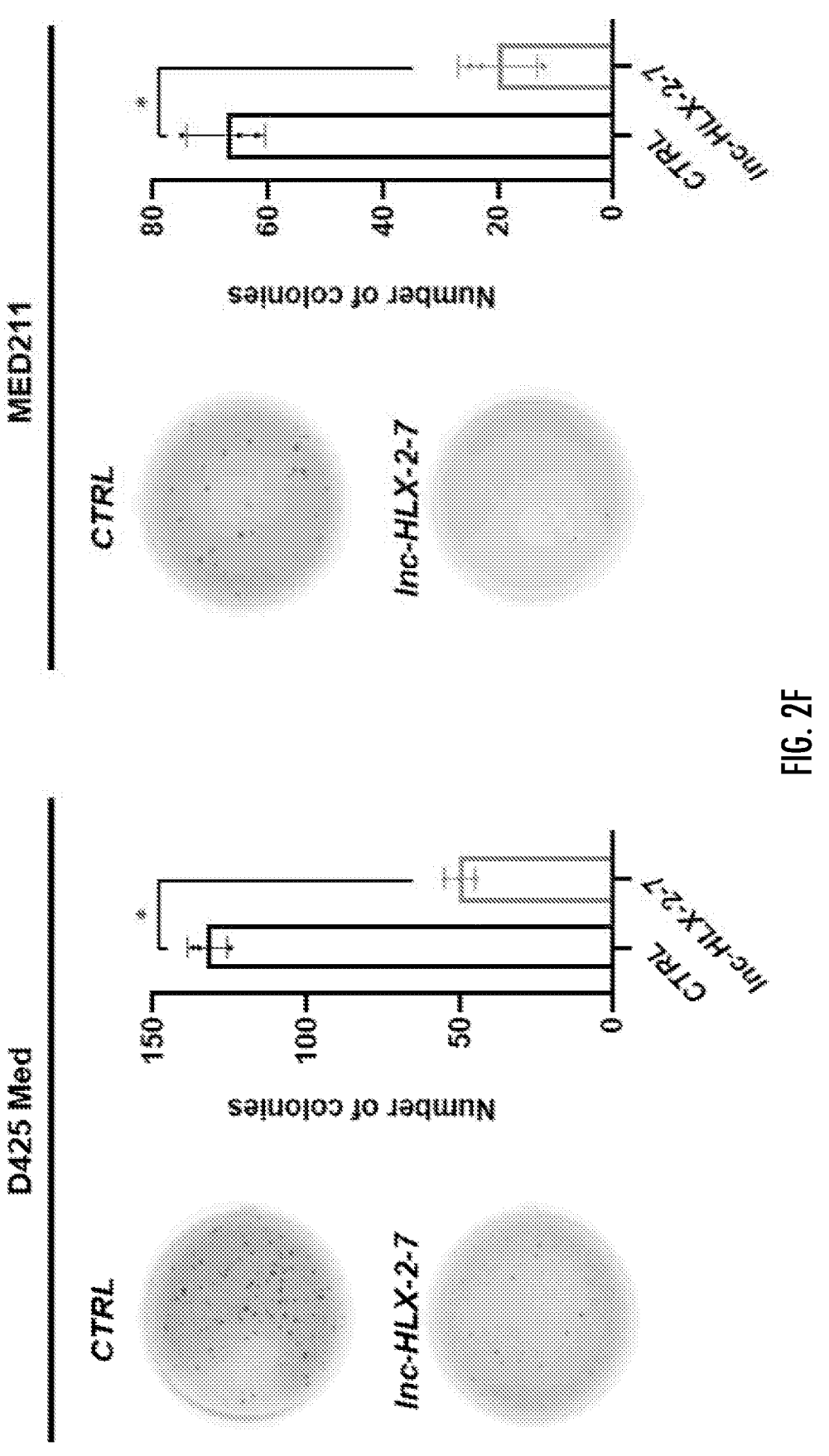
Figure 7A:
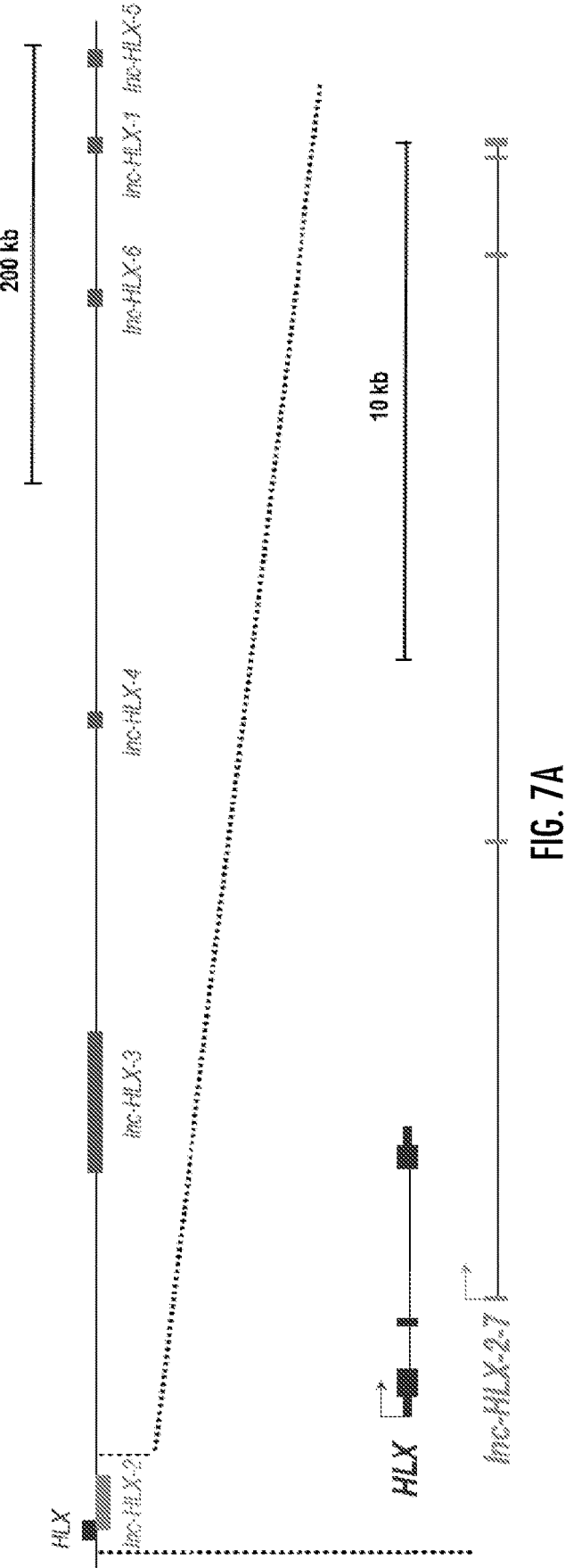
FIG. 7A-7D. Location of HLX and lnc-HLX-2-7 and expression levels of lnc-HLX-2-7 variants.
Figure 7B:
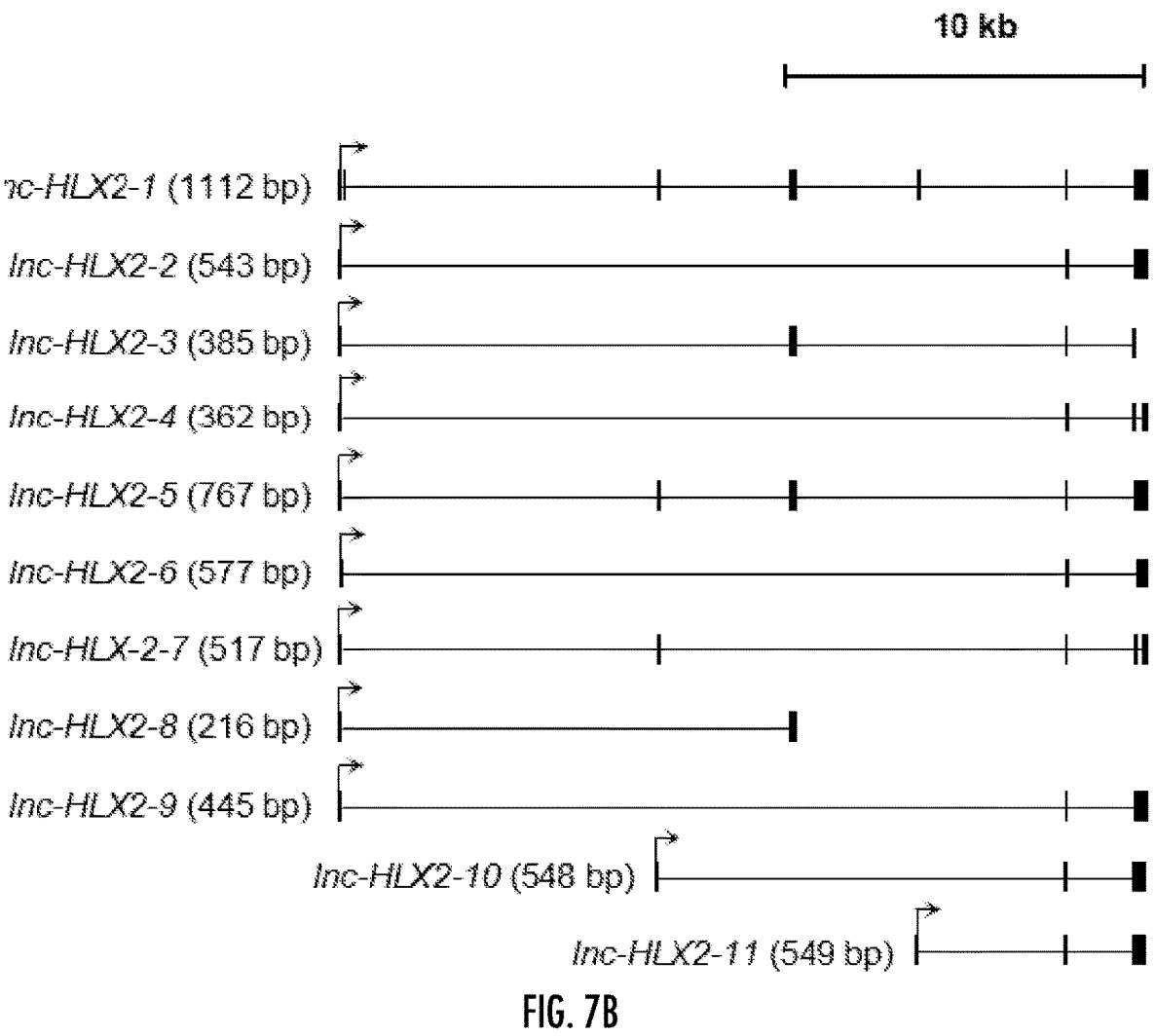
Figure 7C:
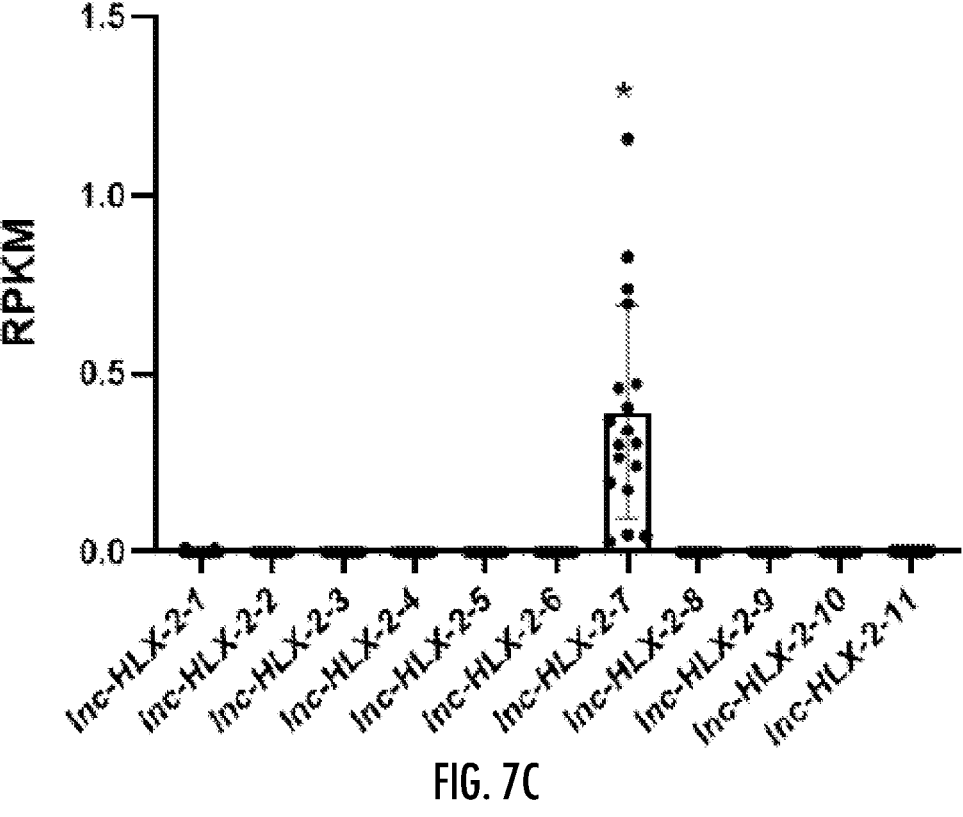
Figure 7D:
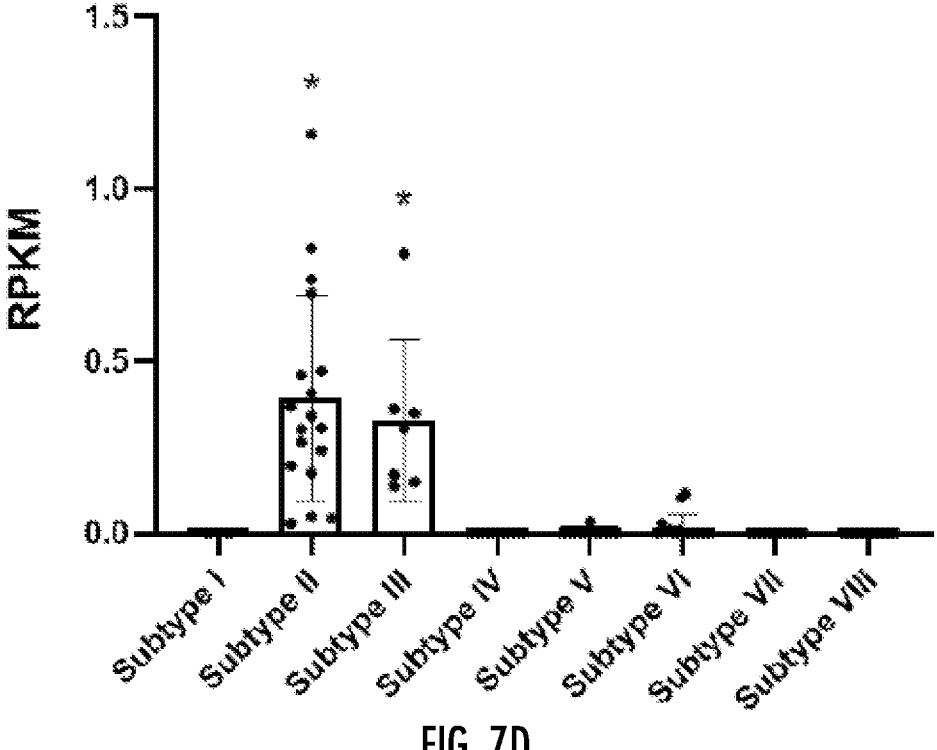

Identification of the group 3-specific long-noncoding RNA, lnc-HLX-2-7. To identify MB group 3-specific lncRNAs, we obtained 175 RNA-seq files (FASTq) representing the four MB subgroups (WNT, SHH, group 3 and group 4) from the European Genome-Phenome Archive (EGA) and applied combined GENCODE and LNCipedia annotations.[22] Given the need to find novel biomarkers that differentiate group 3 from other groups, we identified a set of lncRNAs (lnc-HLX-1, lnc-HLX-2, lnc-HLX-5, and lnc-HLX-6) with markedly elevated and significant overexpression in group 3 MB (FIG. 1A, B and Table 10). lnc-HLX-1, lnc-HLX-2, lnc-HLX-5, and lnc-HLX-6 showed a high expression correlation (FIG. 1C) and were highly expressed in group 3 MB patient samples compared to other subgroups (p<0.01, FIG. 1D). We recently reported that some of these lncRNAs also show group 3-specific differential expression.[23] Due to lnc-HLX-2's proximity to its host coding gene transcription factor and homeobox gene HB24 (HLX) and a recent study reporting that the lnc-HLX-2 region is a group 3 MB-specific enhancer region (not shown),[24] we focused on lnc-HLX-2. lnc-HLX-2 is located 2300 bp downstream of the transcriptional start site (TSS) of HLX (FIG. 7A) and consists of 11 transcripts (lnc-HLX-2-1 to lnc-HLX-2-11; FIG. 7B), of which lnc-HLX-2-7 was highly expressed in group 3 MBs (FIG. 7C). qRT-PCR analysis verified that lnc-HLX-2-7 was highly upregulated in group 3 MB cell lines (FIG. 1E) and PDX samples (FIG. 1F) compared to other groups. It was recently shown through a combined analysis of Group 3 and 4 MBs that they can be further subdivided into eight molecular subtypes, designated I to VIII.[20] In a combined analysis of group 3 and group 4 cases, lnc-HLX-2-7 showed high expression in subtype II and III MBs compared to other subtypes (FIG. 7D).

lnc-HLX-2-7 functions as an oncogene in vitro. To investigate the function of lnc-HLX-2-7, we used antisense oligonucleotides (ASOs) to inhibit lnc-HLX-2-7 expression in D425 Med and MED211 MB cells. Transfection with ASO-lnc-HLX-2-7 significantly decreased lnc-HLX-2-7 expression compared to controls (ASO-luc) in both cell lines (p<0.01, FIG. 2A), which significantly suppressed MB cell growth and induced apoptosis (p<0.01, FIG. 2B, C). Next, CRISPR/Cas9 knock-down was used to generate single-cell colonies and further investigate the effect of lnc-HLX-2-7 in MB cells. We generated stable D425 Med and MED211-lnc-HLX-2-7-sgRNA cells, which constitutively expressed sgRNAs against lnc-HLX-2-7 to reduce lnc-HLX-2-7 expression (FIG. 2D). As expected, D425 Med and MED211-lnc-HLX-2-7-sgRNA cells showed reduced growth (FIG. 2E) and colony-forming ability (FIG. 2F) when compared D425 Med and MED211 control cells in vitro.

Figure 3A:
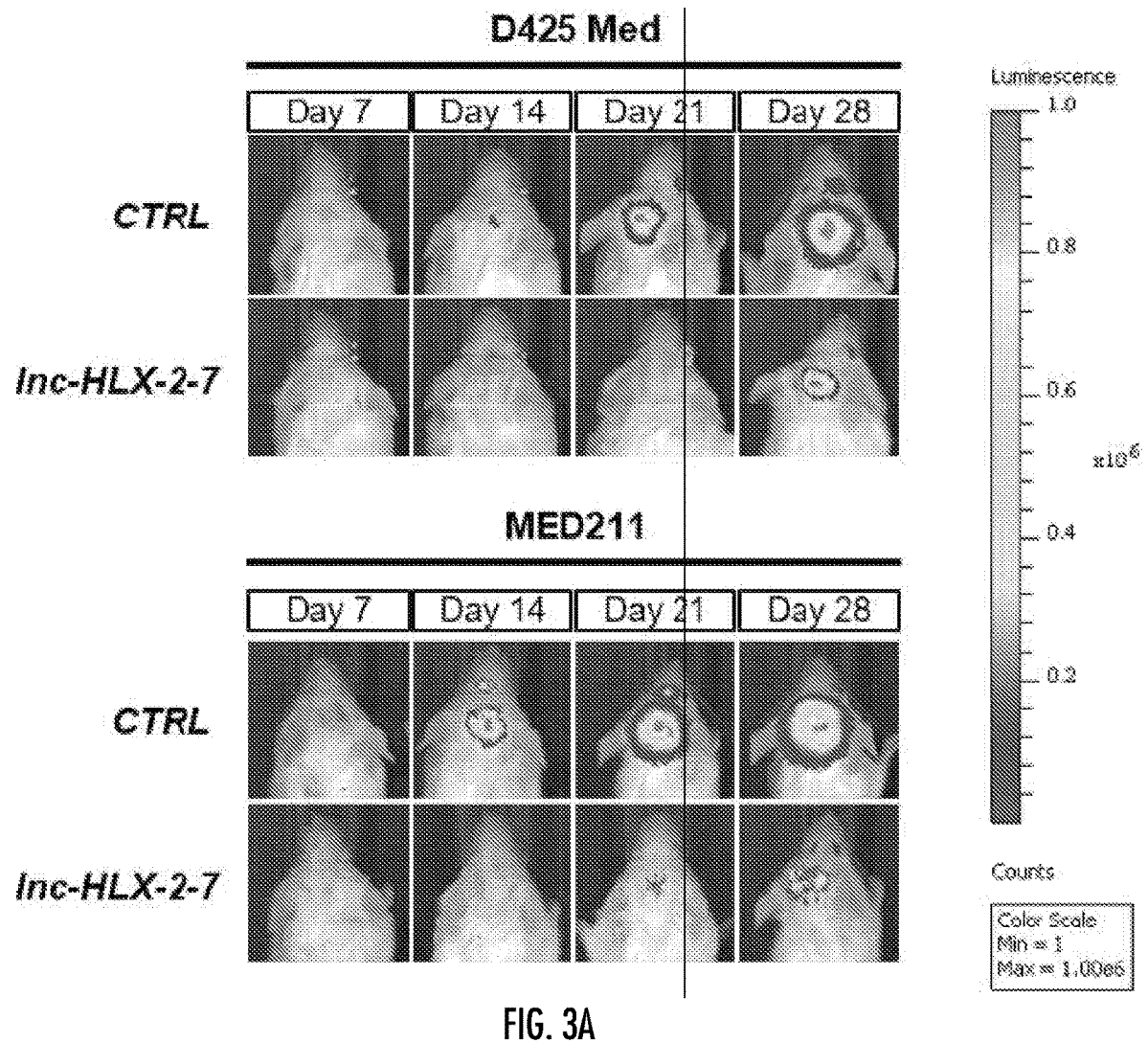
FIG. 3A-3E. lnc-HLX-2-7 promotes the tumorigenicity of group 3 MB cells in vivo.
Figure 3B:
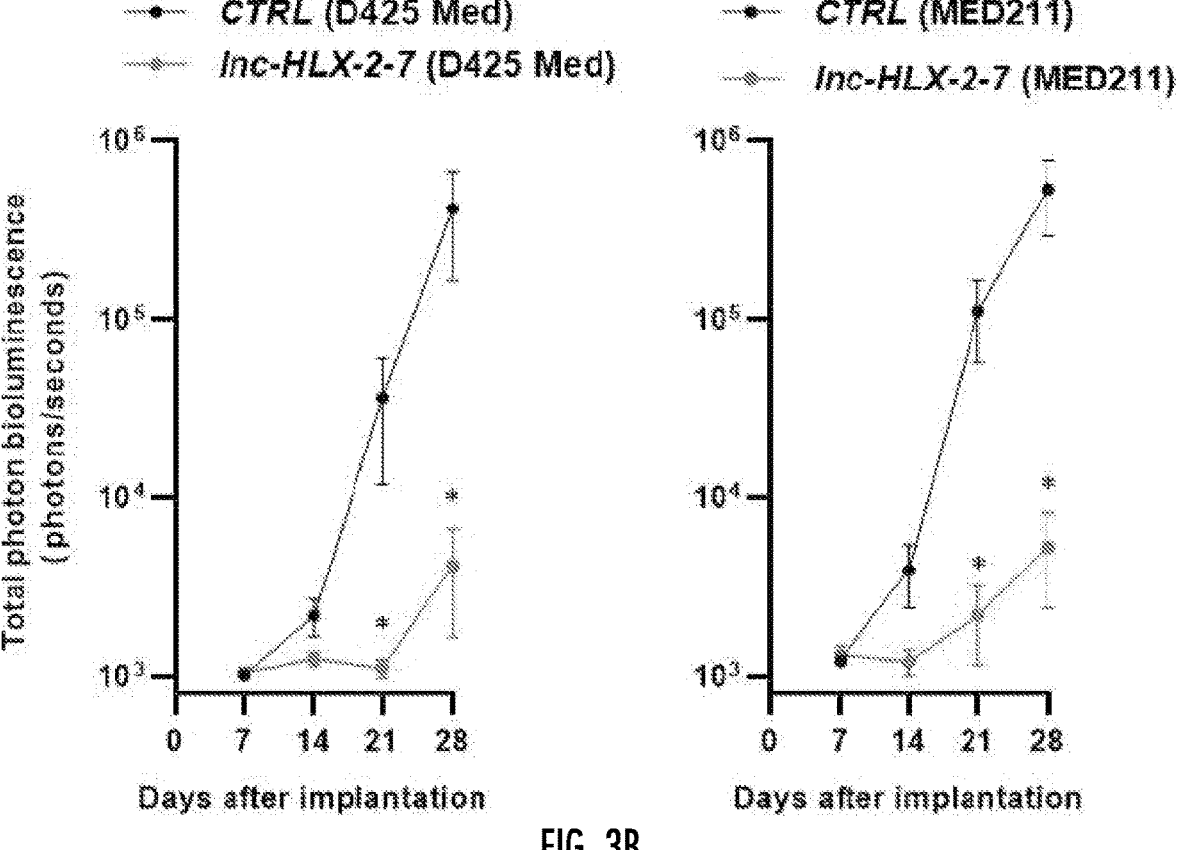
Figure 3C:
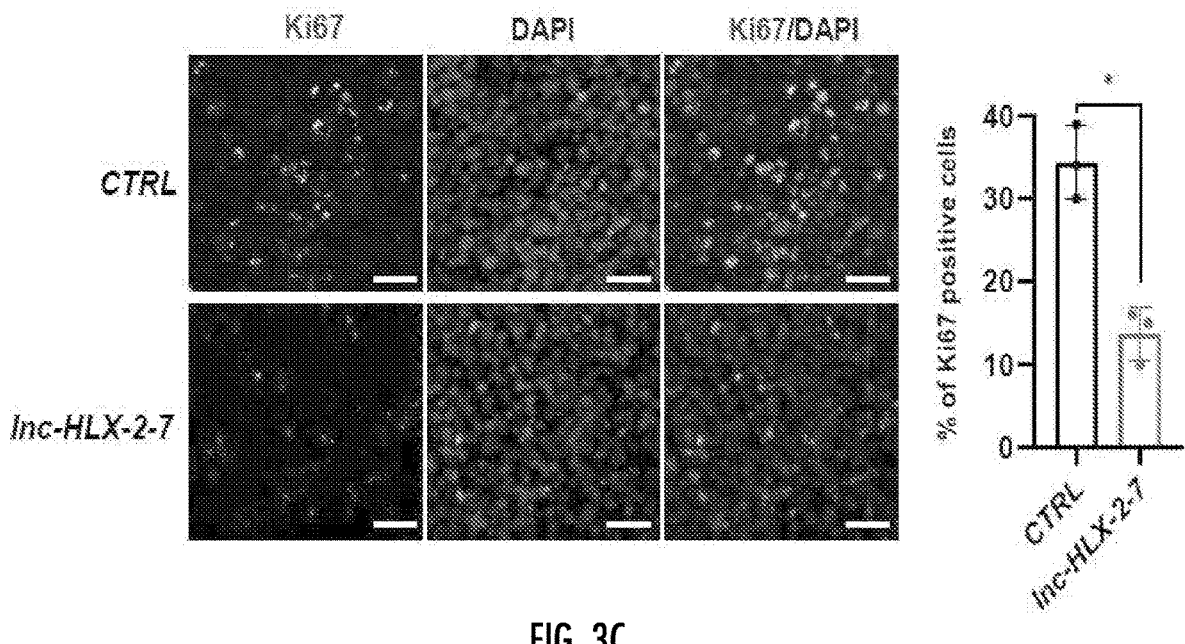
Figure 3D:
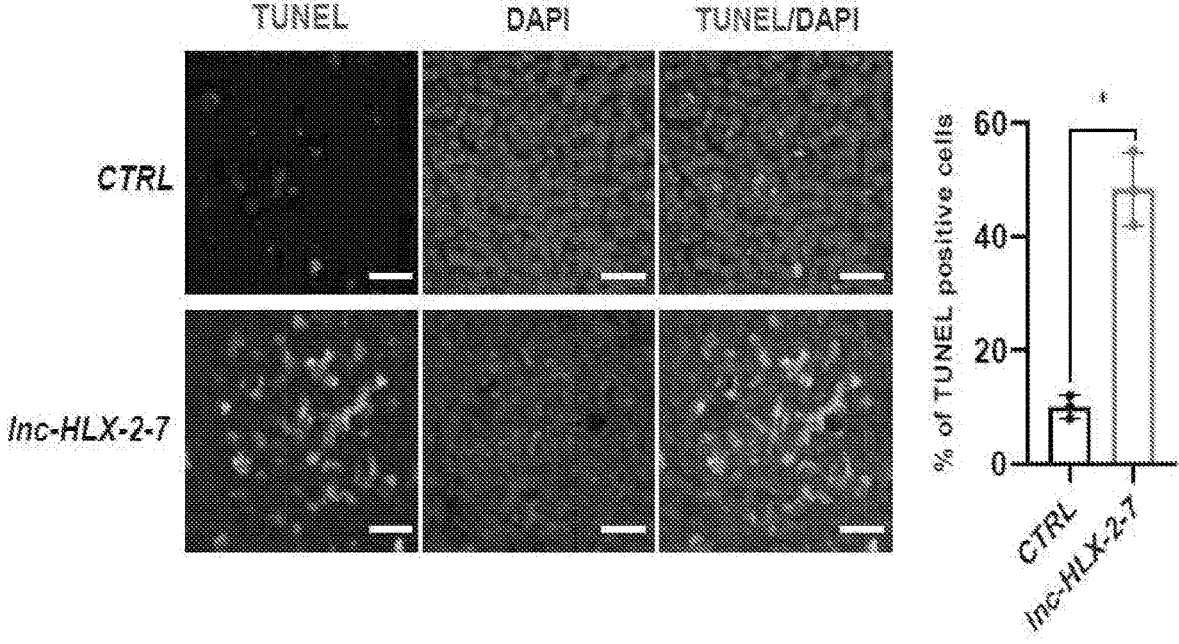
Figure 3E:
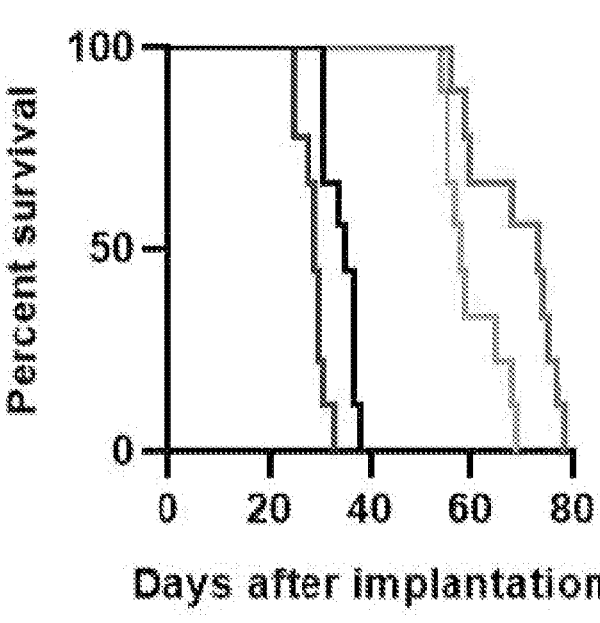
Figure 8:
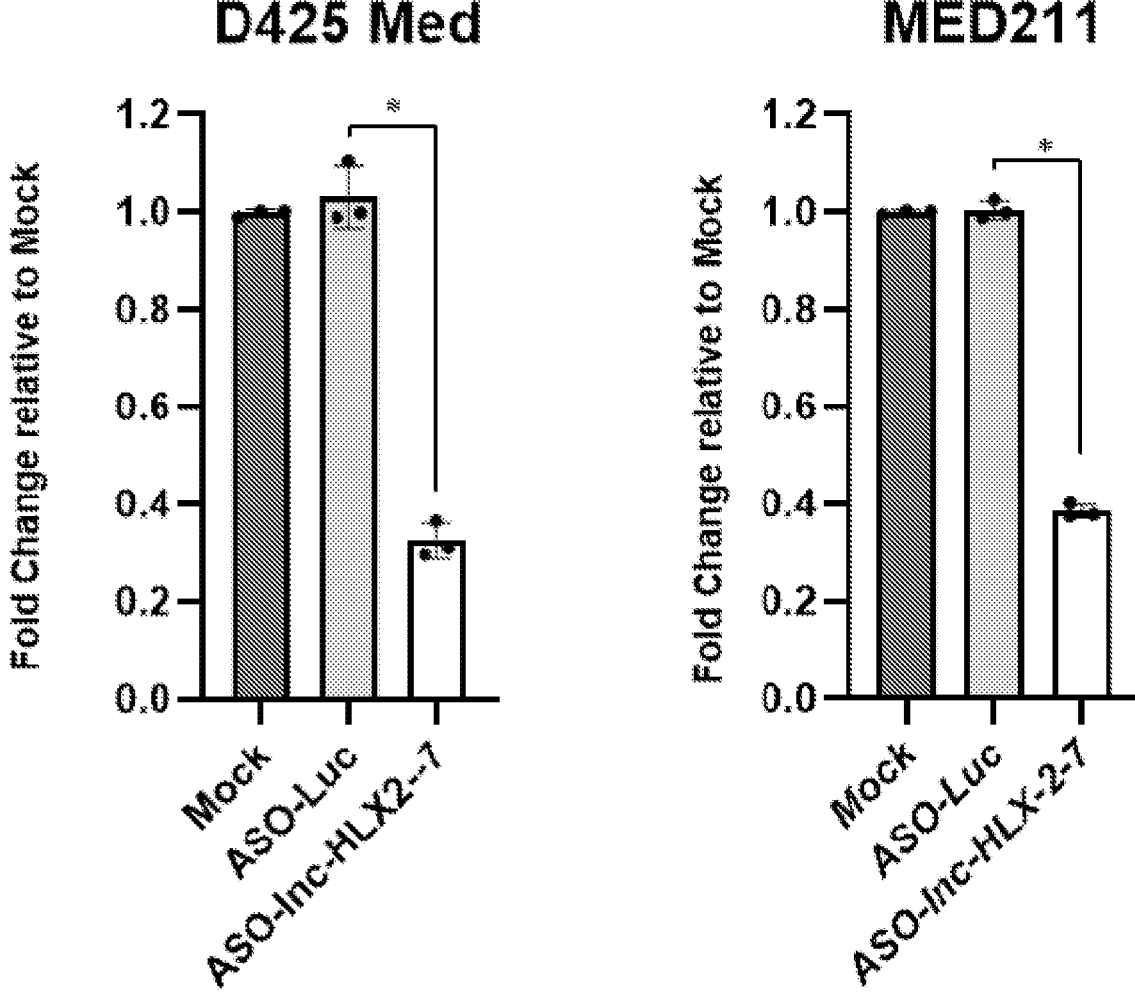
FIG. 8. lnc-HLX-2-7 regulates the expression of HLX coding gene. Expression levels of HLX in D425 Med and MED211 cells treated with ASO against the indicated genes in the x-axis. Relative expression level to mock is indicated in the y-axis. *p<0.01, Kruskal-Wallis analysis.
Figures 9A, 9B:
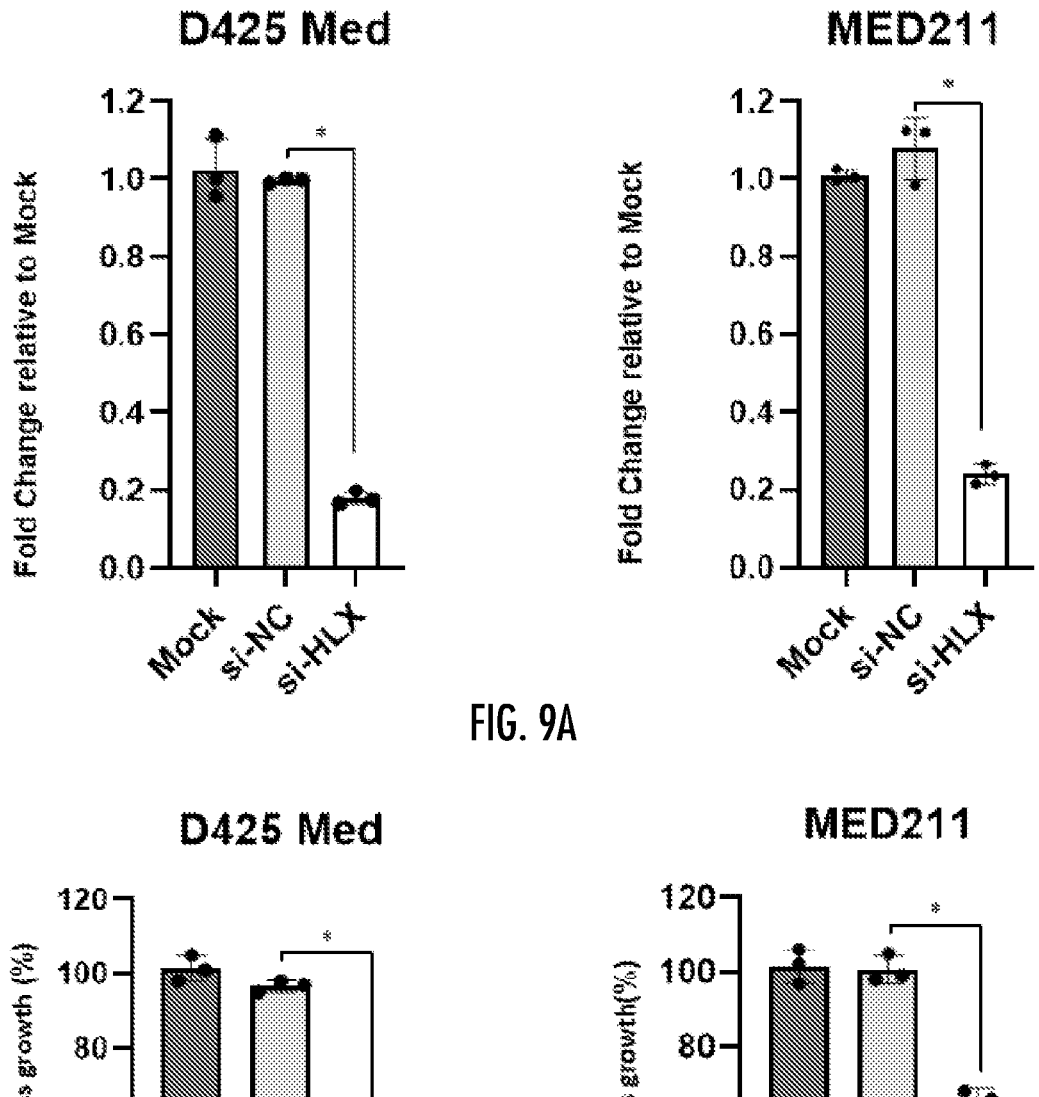
FIG. 9A-9B. Effects of HLX expression on the proliferation of D425 Med and MED211.

While the functions of the majority of lncRNAs are not yet known, some have been shown to function in cis by regulating the expression of neighboring genes.[25-27] Since lnc-HLX-2-7 is located downstream of the HLX transcription start site (TSS; FIG. 7A), we determined whether lnc-HLX-2-7 regulates HLX expression; indeed, HLX expression was significantly reduced in D425 Med and MED211 cells following treatment with ASO-lnc-HLX-2-7 (FIG. 8). In addition, HLX knockdown significantly decreased the growth of D425 Med and MED211 cells (FIG. 9A-9B). While the current study focuses on the role of lncRNA HLX-2-7, understanding the molecular function of its host-coding gene HLX requires further investigation, which is ongoing.

lnc-HLX-2-7 regulates tumor formation in mouse intracranial xenografts. To evaluate the effect of lnc-HLX-2-7 on tumor growth in vivo, we established intracranial MB xenografts in NOD-SCID mice. D425 Med and MED211 control cells and D425 Med and MED211-lnc-HLX-2-7-sgRNA cells were pre-infected with a lentivirus containing a luciferase reporter. Weekly evaluation of tumor growth by bioluminescence imaging revealed significantly smaller tumors in mice transplanted with D425 Med and MED211-lnc-HLX-2-7-sgRNA cells compared to mice transplanted with control cells (n=9, p<0.05, FIG. 3A, B). At day 30, tumors were harvested and cut into sections and then subjected to Ki67 and TUNEL staining. Ki67 analysis showed reduced cell proliferation in D425 Med-lnc-HLX-2-7-sgRNA cell-transplanted mice (p<0.01, FIG. 3C). TUNEL analysis found out that lnc-HLX-2-7 depletion induced significantly higher percentage of TUNEL-positive cells than compared to mice transplanted with control cells (p<0.01, FIG. 3D). Kaplan-Meier plots demonstrated that the group transplanted with D425 Med and MED211-lnc-HLX-2-7-sgRNA cells had significantly prolonged survival compared to the control (FIG. 3E). Together, these results demonstrate that lnc-HLX-2-7 regulates tumor growth in vivo and may function as an oncogene.

Figure 4A:
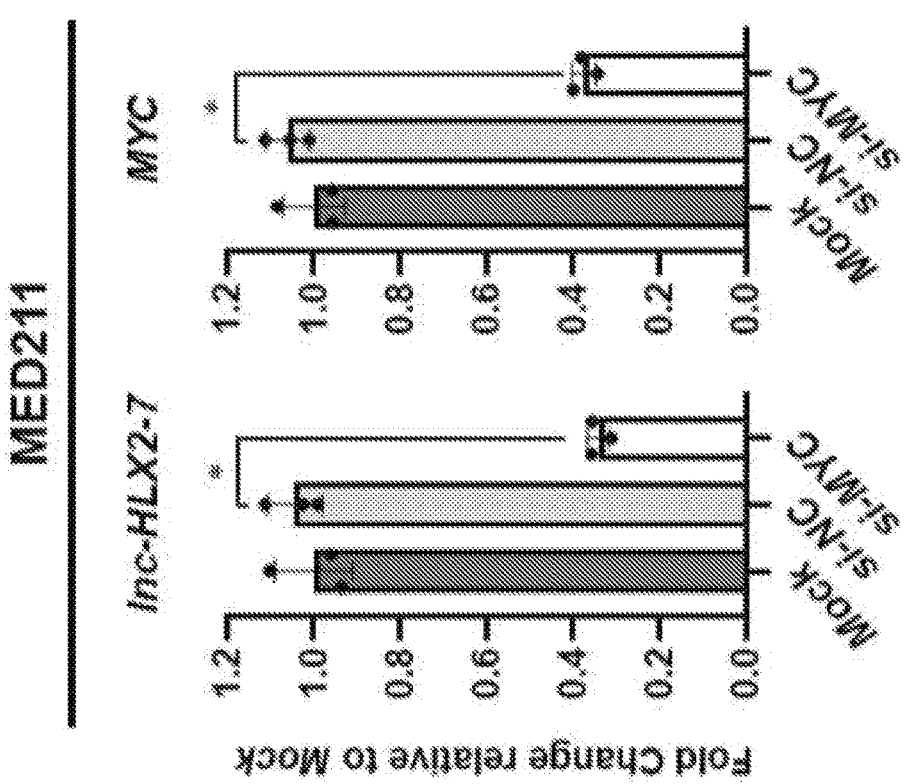
FIG. 4A-4D. MYC regulates the expression of lnc-HLX-2-7 in group 3 MB.
Figure 4A:
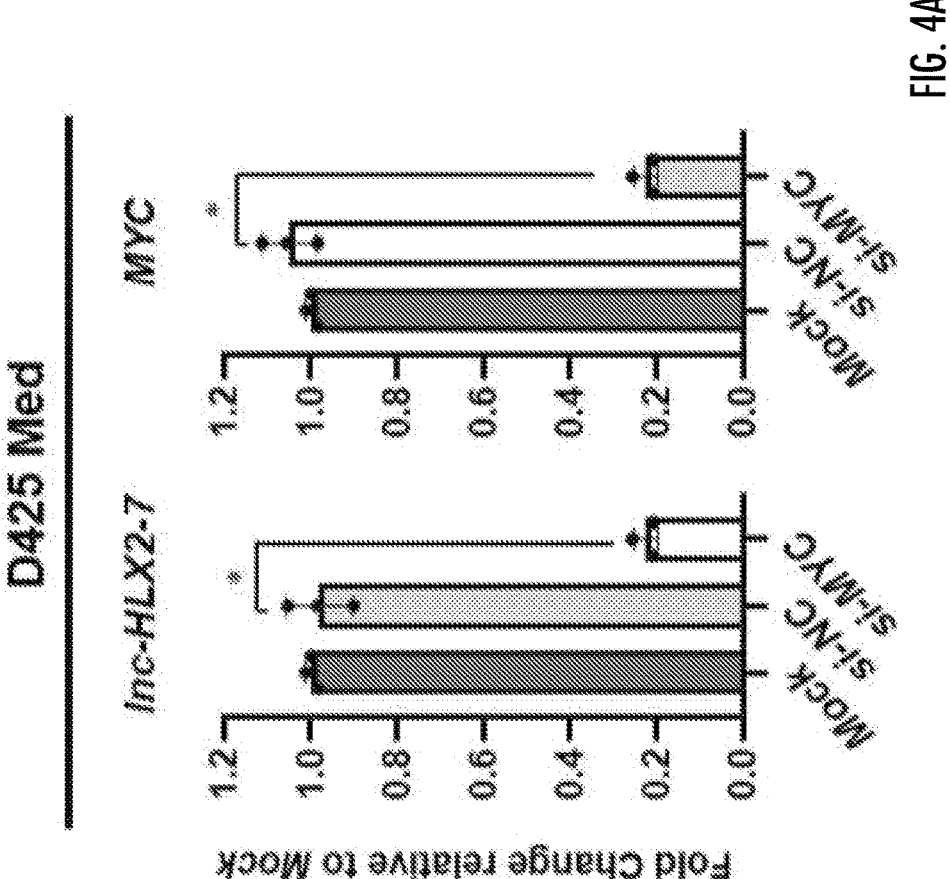
Figure 4B:
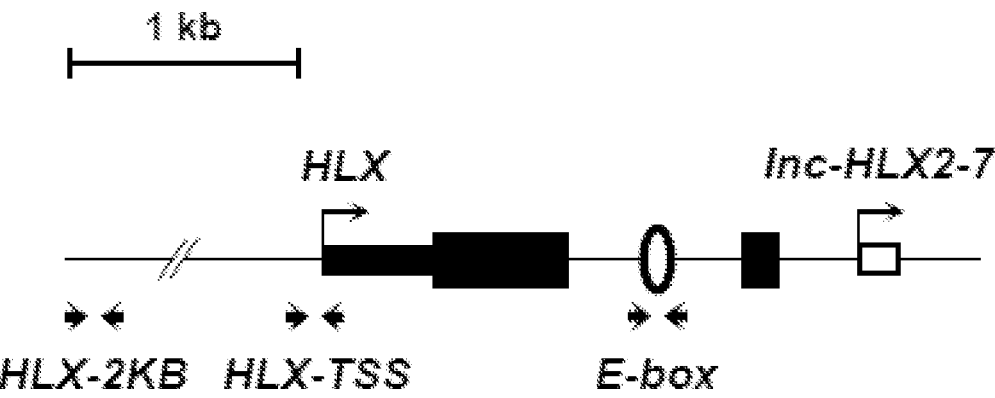
Figure 4C:
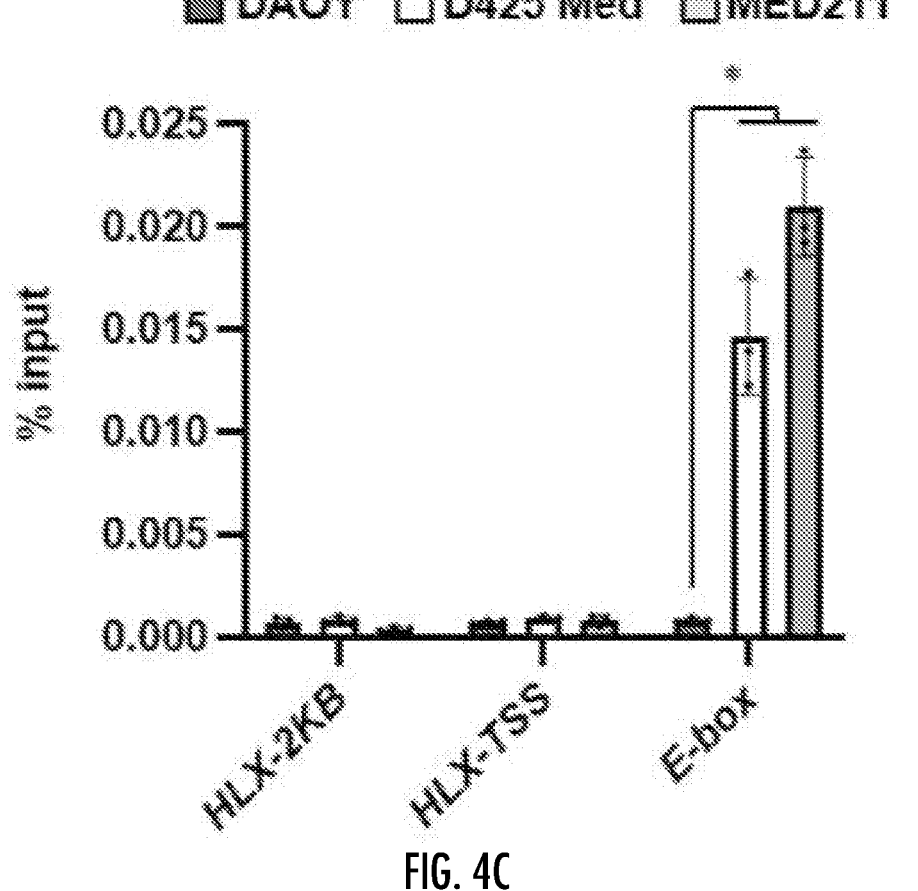

Transcriptional regulation of lnc-HLX-2-7 by the MYC oncogene. Since the majority of group 3 tumors exhibit elevated expression and amplification of the MYC oncogene,[2,28] we hypothesized that MYC may regulate the expression of lnc-HLX-2-7. We therefore knocked down MYC by siRNA in D425 Med and MED211 cells, which decreased the expression of both MYC and lnc-HLX-2-7 (FIG. 4A), suggesting that MYC may be an upstream regulator of lnc-HLX-2-7. To further support this, we also identified a MYC-binding motif (E-box; -CACGTG-) 772 bp upstream of the putative TSS of lnc-HLX-2-7 using the JASPAR CORE database (http://jaspar.binf.ku.dk/)[29] (FIG. 4B). To test whether MYC could interact with the endogenous lnc-HLX-2-7 promoter, chromatin immunoprecipitation (ChIP) was performed in D425 Med and MED211 cells. ChIP analysis revealed that MYC bound to the E-box motif within the upstream region of lnc-HLX-2-7 in D425 Med and MED211 cells, but not in DAOY cells (FIG. 4C). These results strongly suggest that MYC is a direct regulator of lnc-HLX-2-7.

Figure 4D:
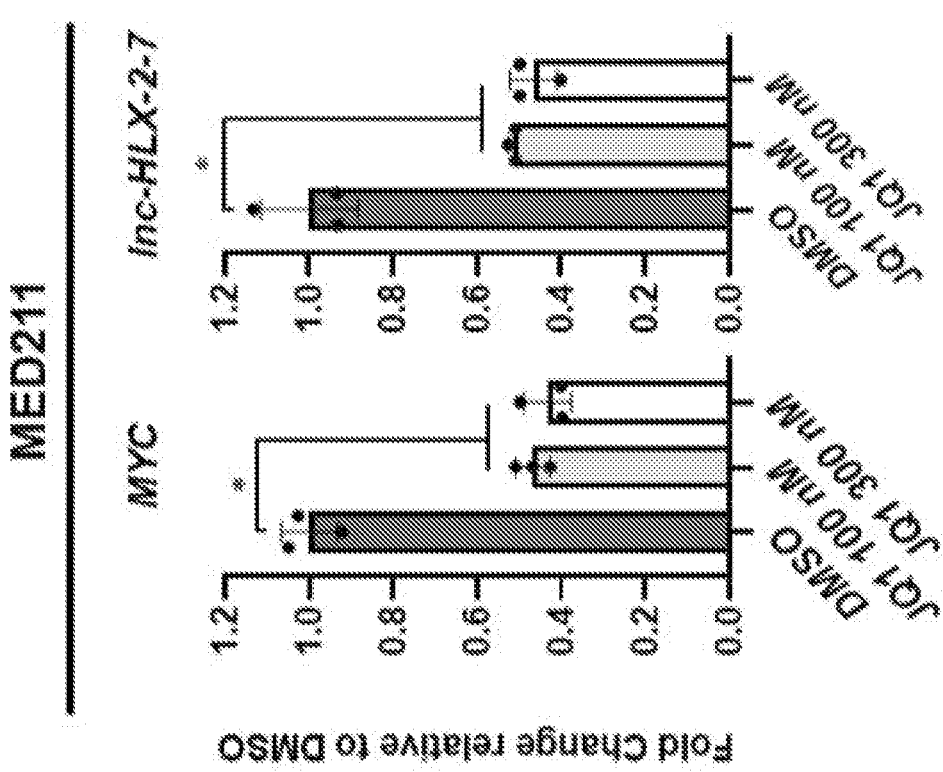
Figure 4D:
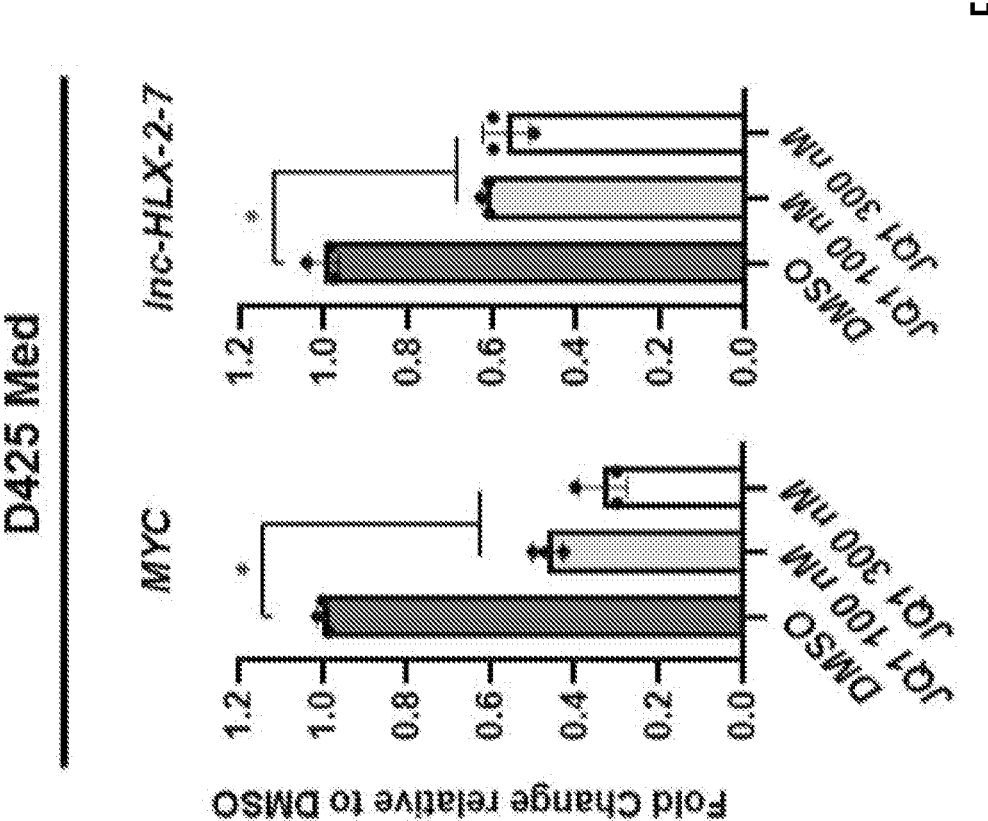
Figure 10A:
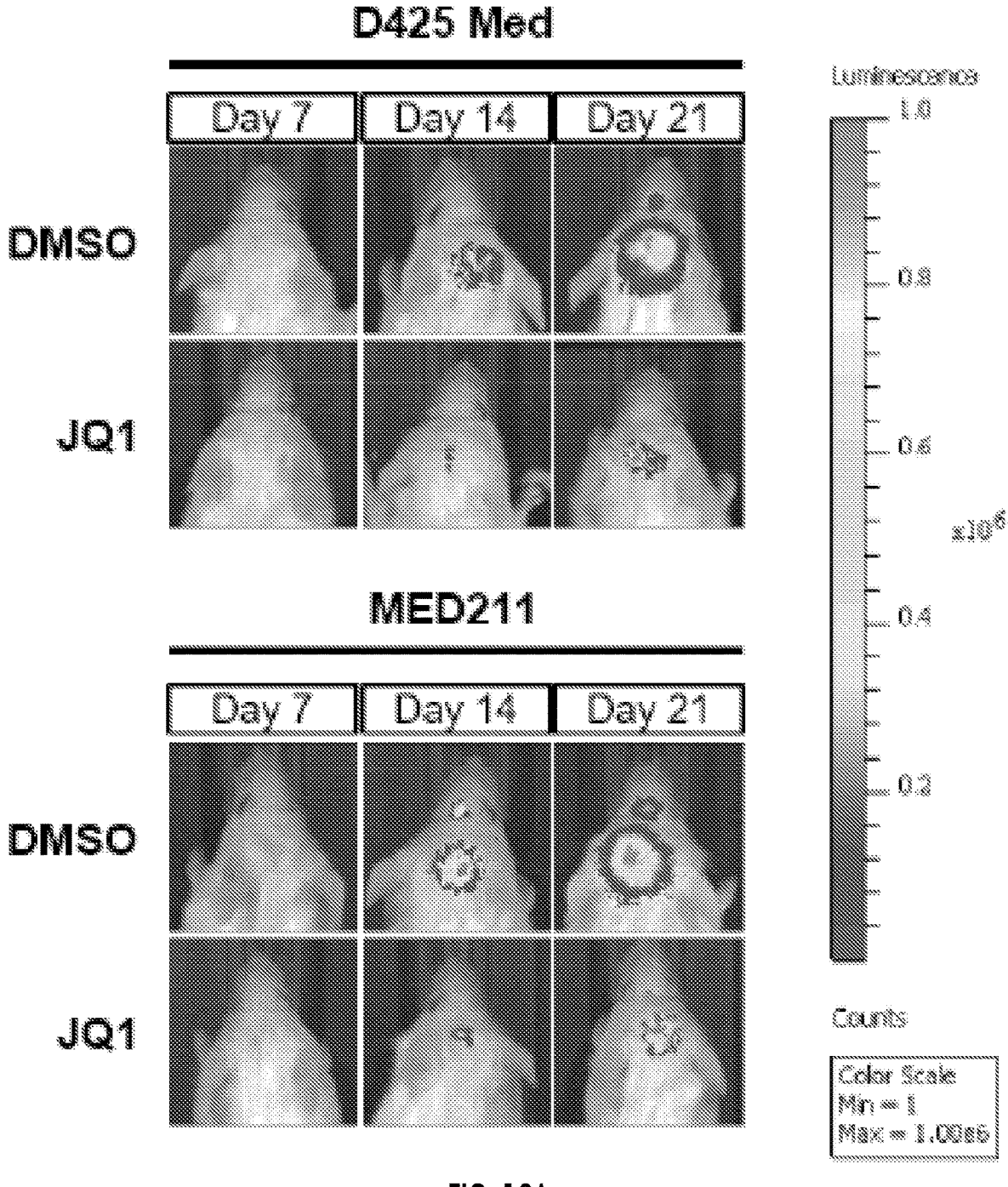
FIG. 10A-10C. JQ1 regulates lnc-HLX2-7 via MYC in vivo.
Figure 10B:
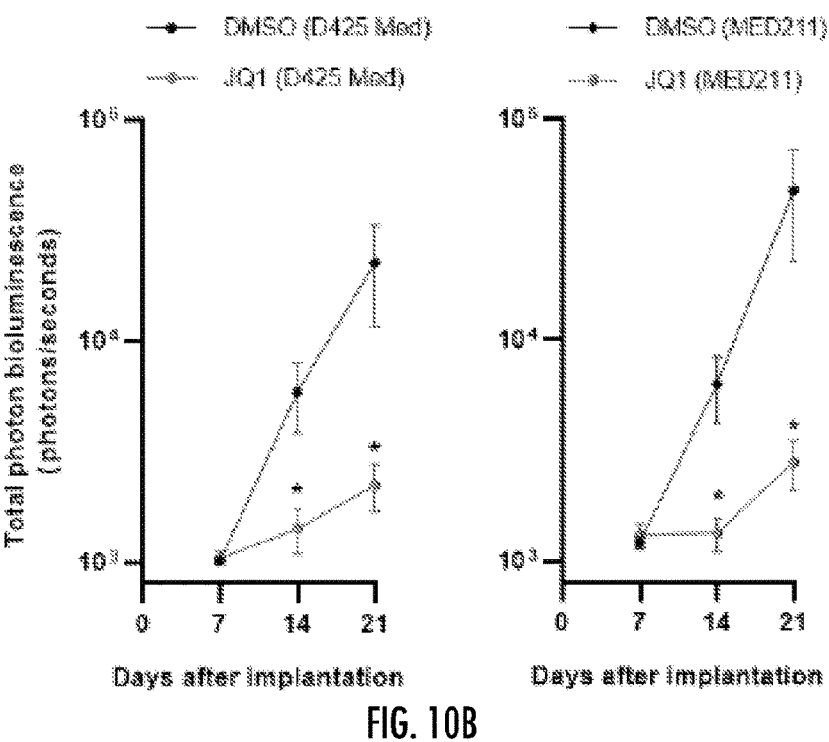
Figure 10C:
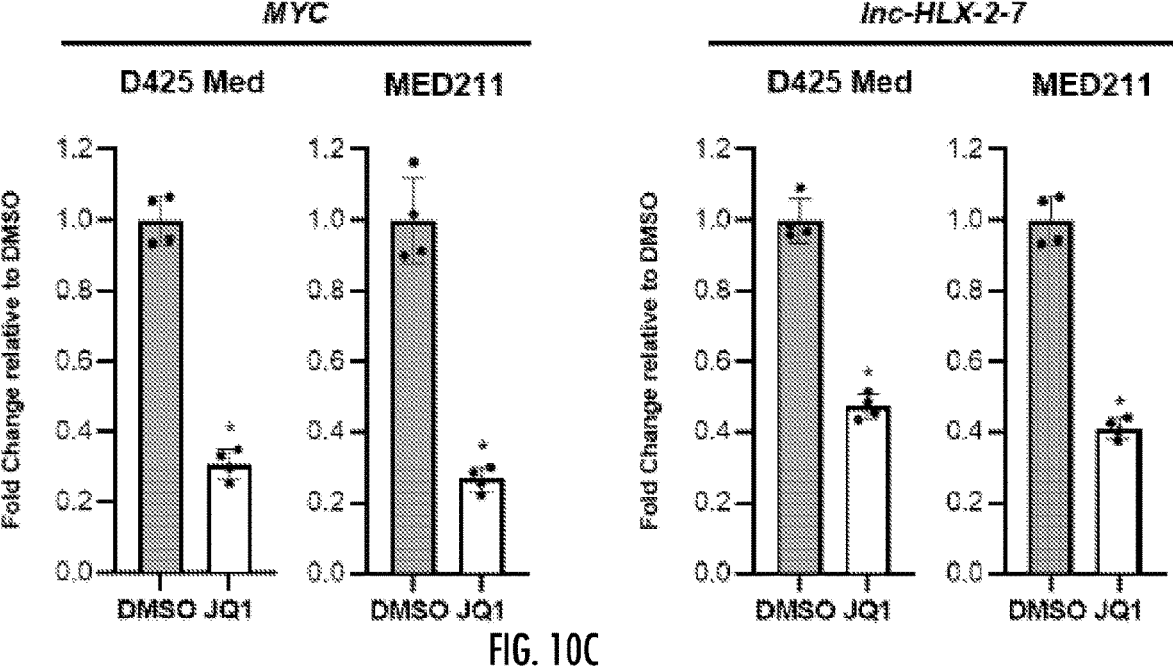
Figure 11A:
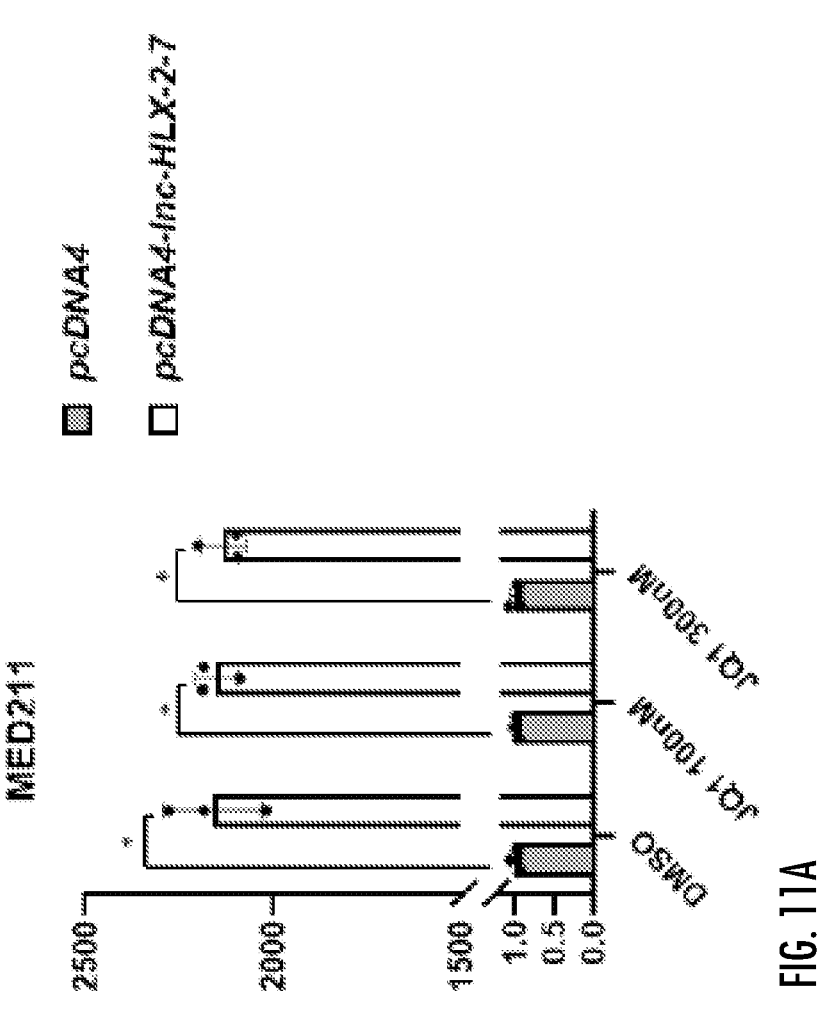
FIG. 11A-11C. Overexpression of lnc-HLX-2-7 rescued cell growth inhibition and downregulation of MYC by JQ1.
Figure 11A:
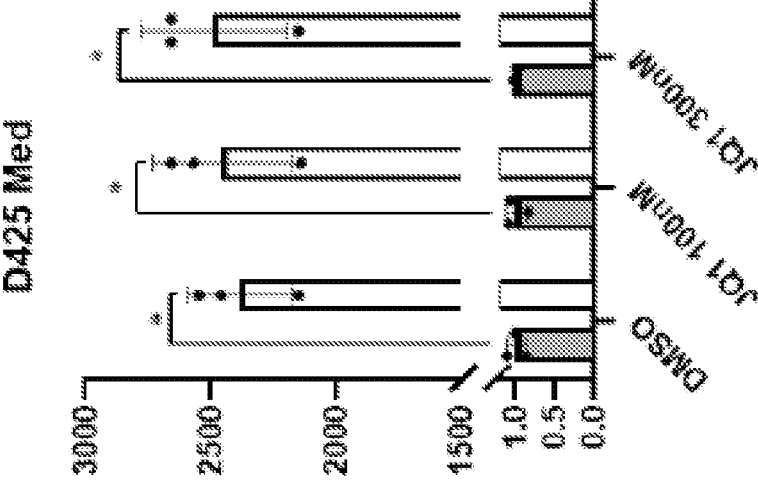
Figure 11B:
Figure 11B:
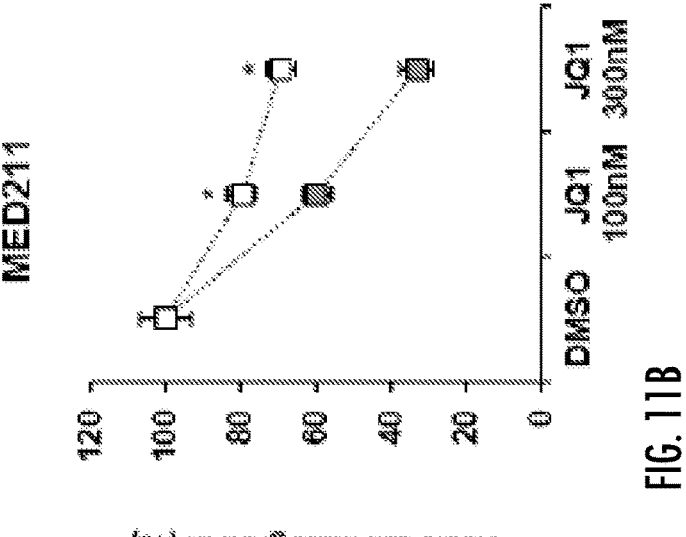
Figure 11B:
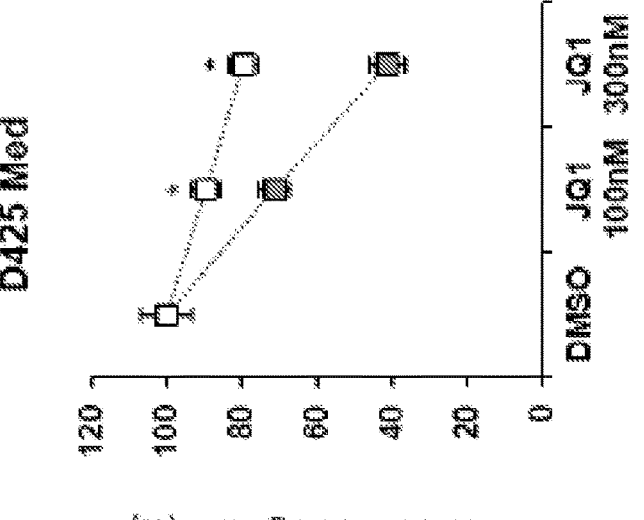
Figure 11C:
Figure 11C:
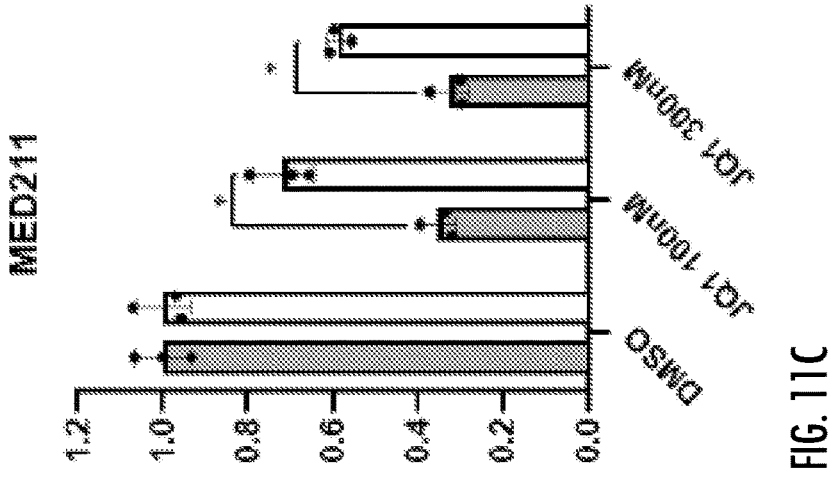
Figure 11C:
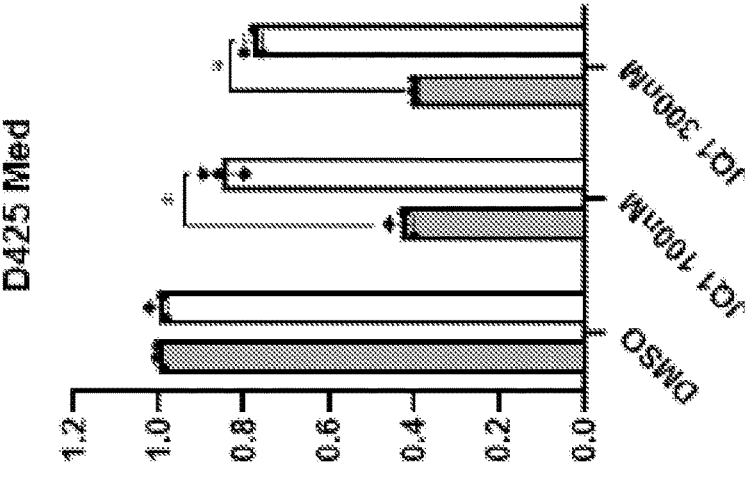

JQ1 regulates lncHLX2-7 via MYC. Several previous studies have demonstrated that BRD4, a member of the bromodomain and extraterminal domain (BET) family, regulates MYC transcription and that JQ1 effectively suppresses cancer cell proliferation by inhibiting BRD4-mediated regulation of MYC in various types of cancer including MB.[30-34] To test the JQ1 effect on lnc-HLX-2-7 regulation, we treated D425 Med and MED211 cells with different doses (100 or 300 nM) of the drug. As shown in FIG. 4D, both MYC and lnc-HLX-2-7 were downregulated in D425 Med and MED211 cells. In addition, downregulation of lnc-HLX2-7 by JQ1 was also confirmed in vivo (FIG. 10A-10C). Interestingly, overexpression of lnc-HLX-2-7 suppressed cell growth inhibition and downregulation of MYC by JQ1 (FIG. 11A-11C). Collectively, our results show that BRD4 inhibitors can be used to target MYC-mediated regulation of lnc-HLX-2-7 expression.

Figure 5A:
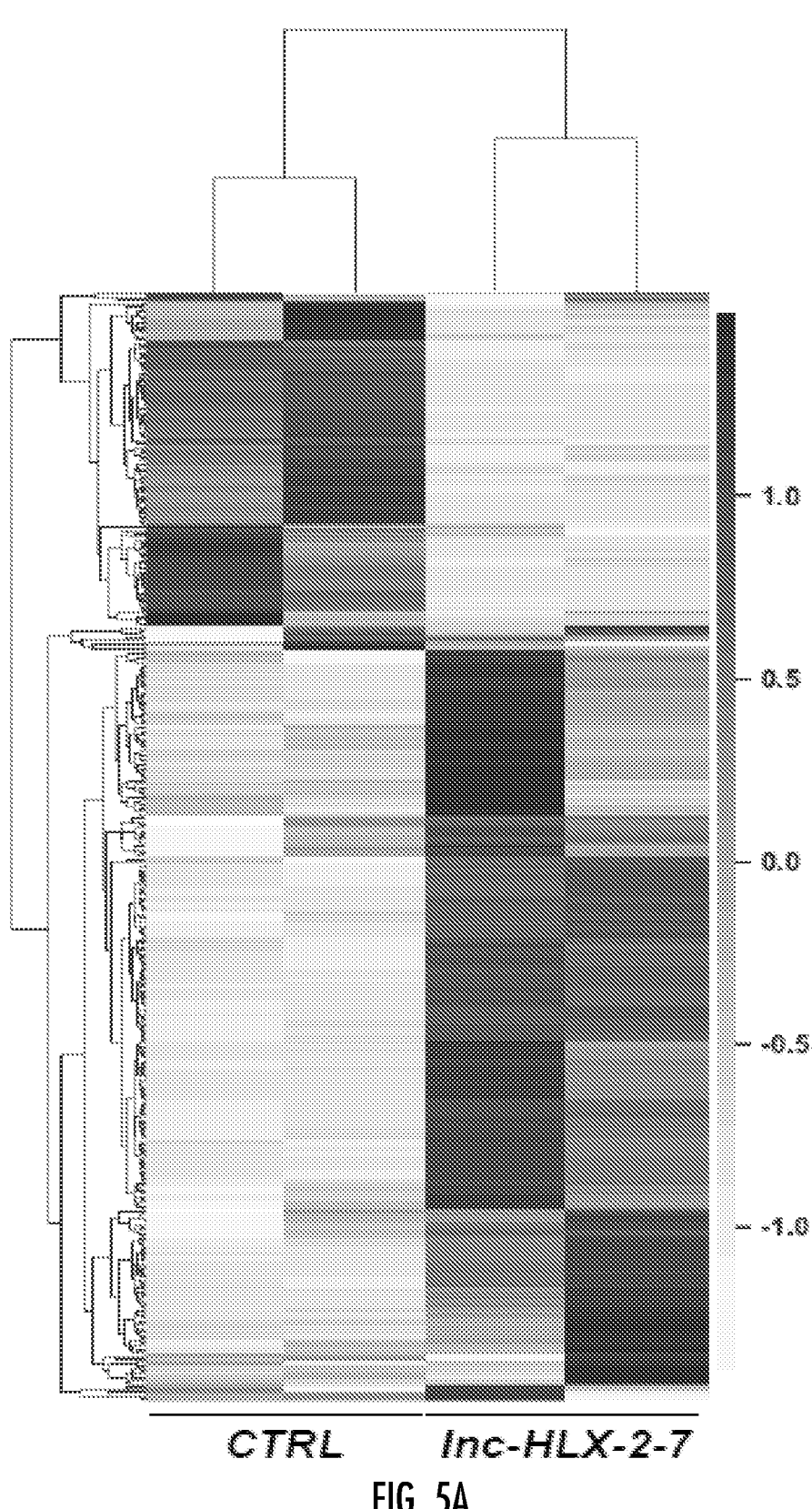
FIG. 5A-5G. RNA sequencing detects lnc-HLX-2-7 interacting genes and pathways.
Figures 5B, 5C:
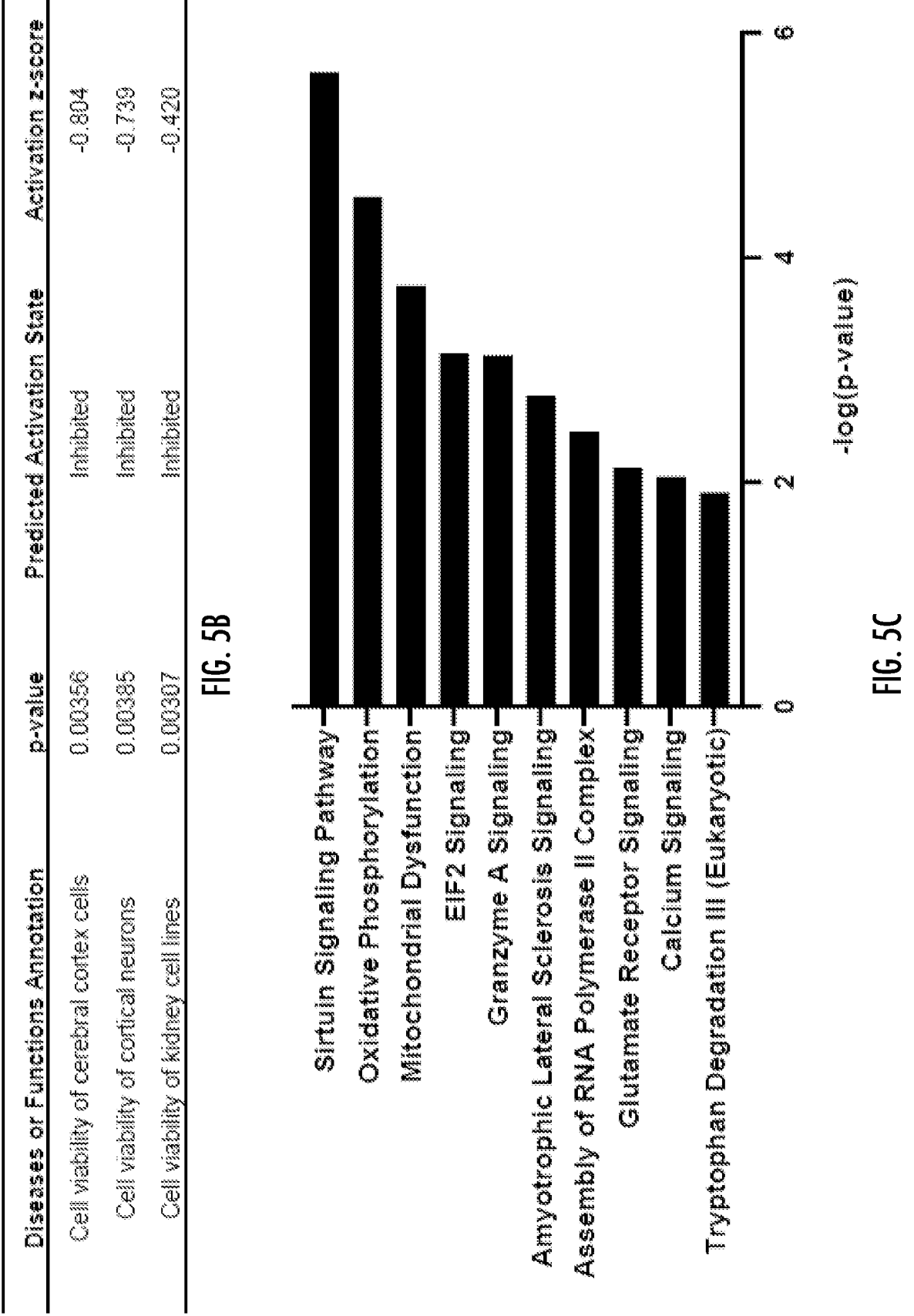
Figure 5D:
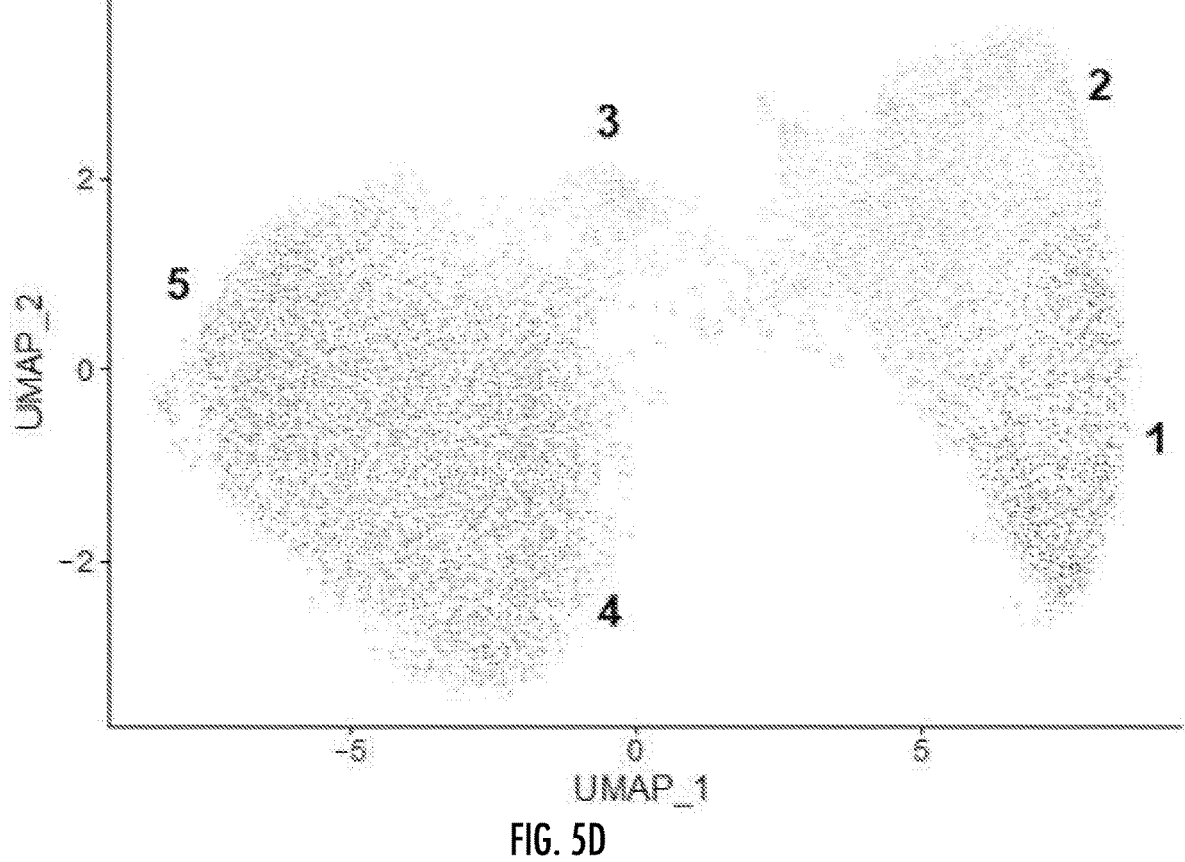
Figure 5E:
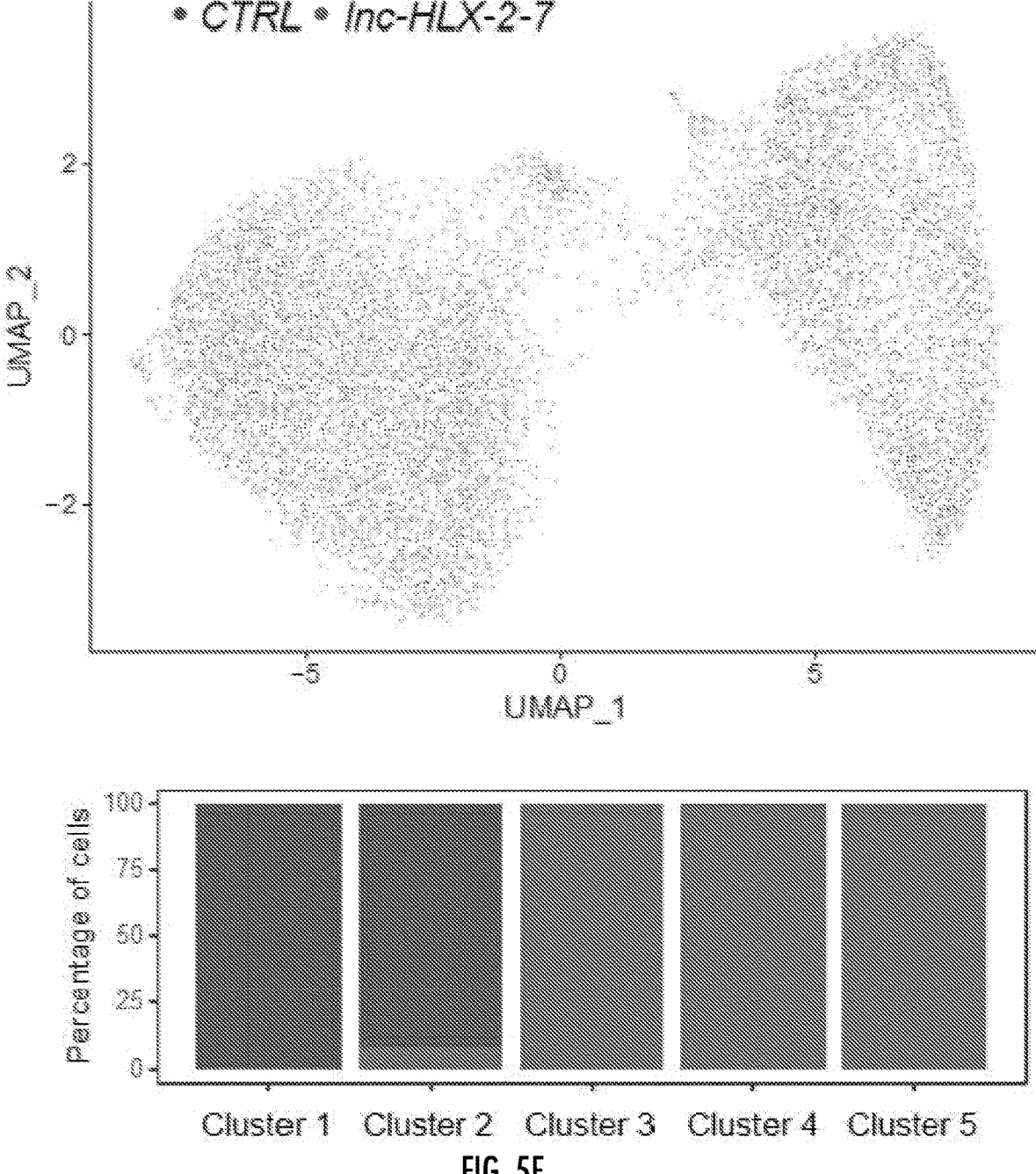
Figure 5F:
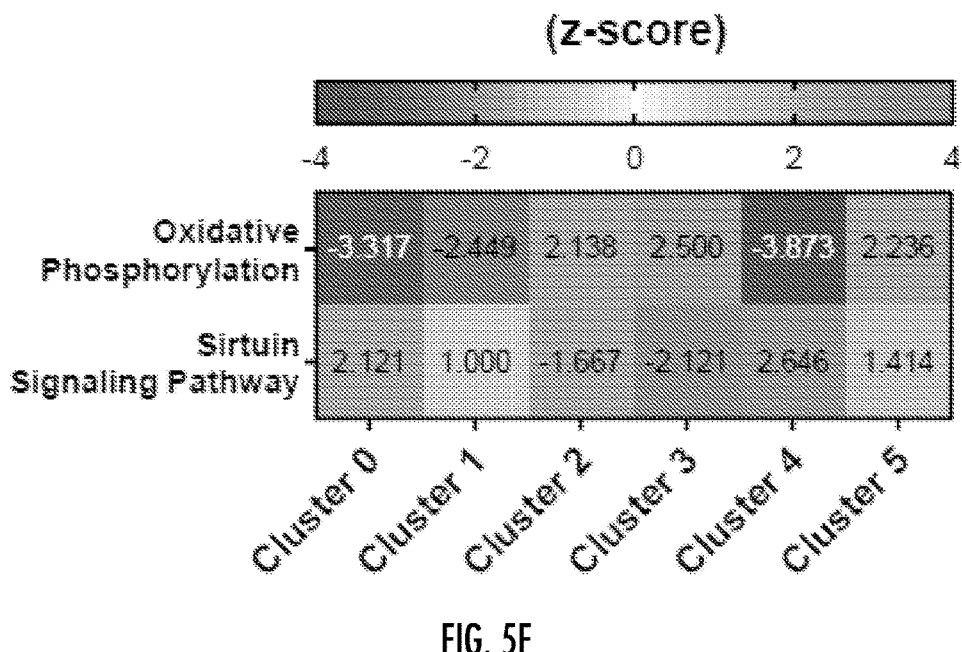
Figure 5G:
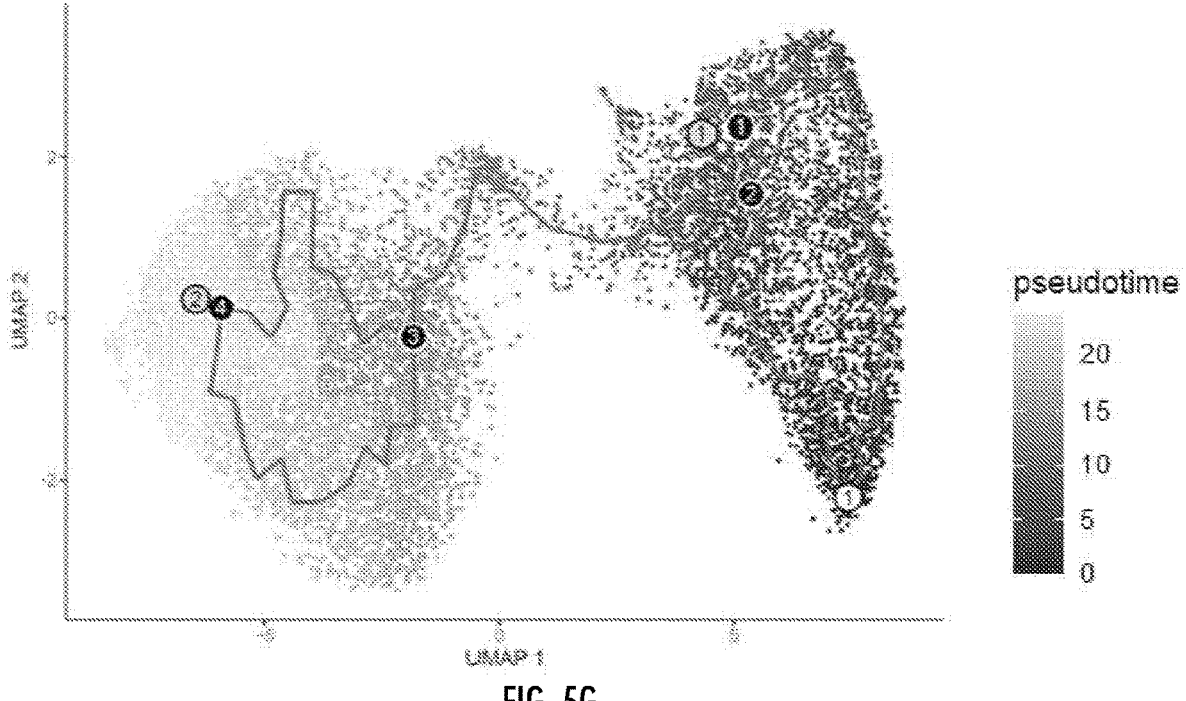
Figure 6A:
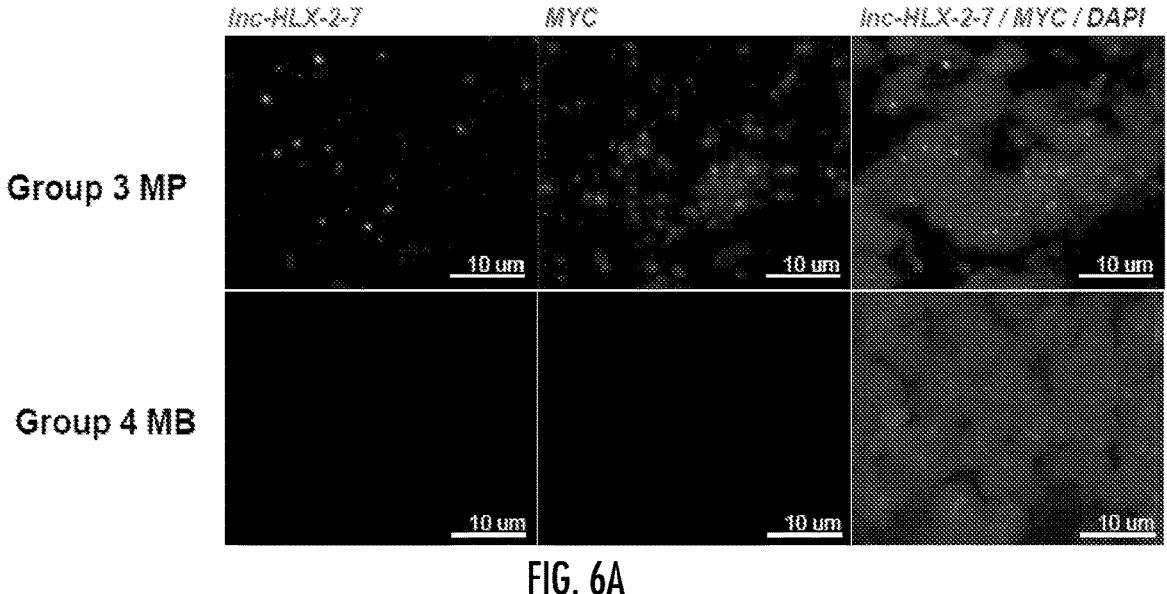
FIG. 6A-6E. RNA-FISH confirms that lnc-HLX-2-7 expression is specific to group 3 MB patients.
Figure 6B:
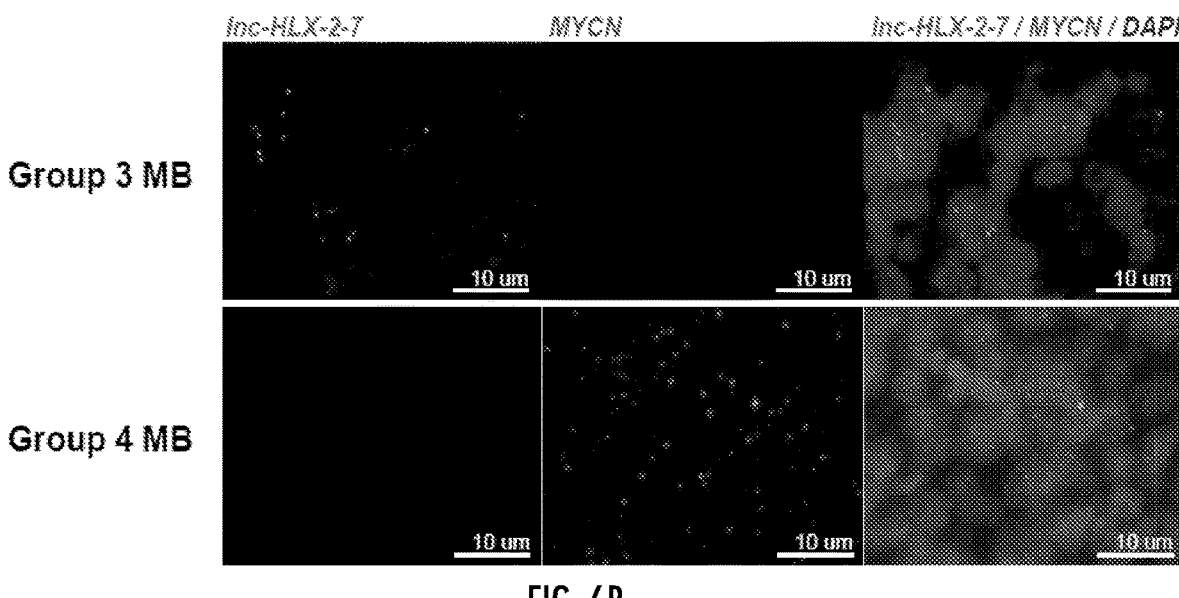
Figures 6C, 6D:
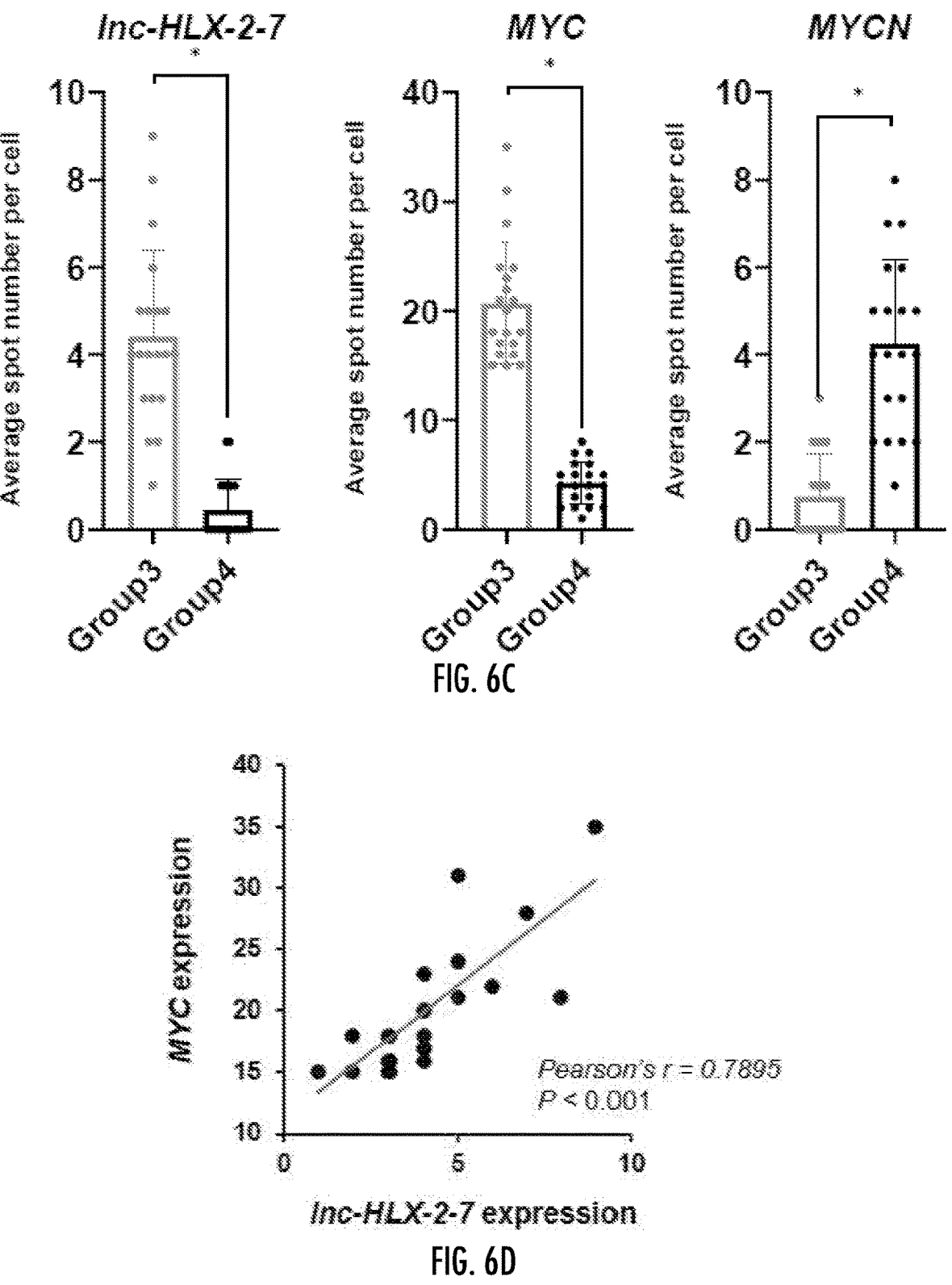
Figure 6E:
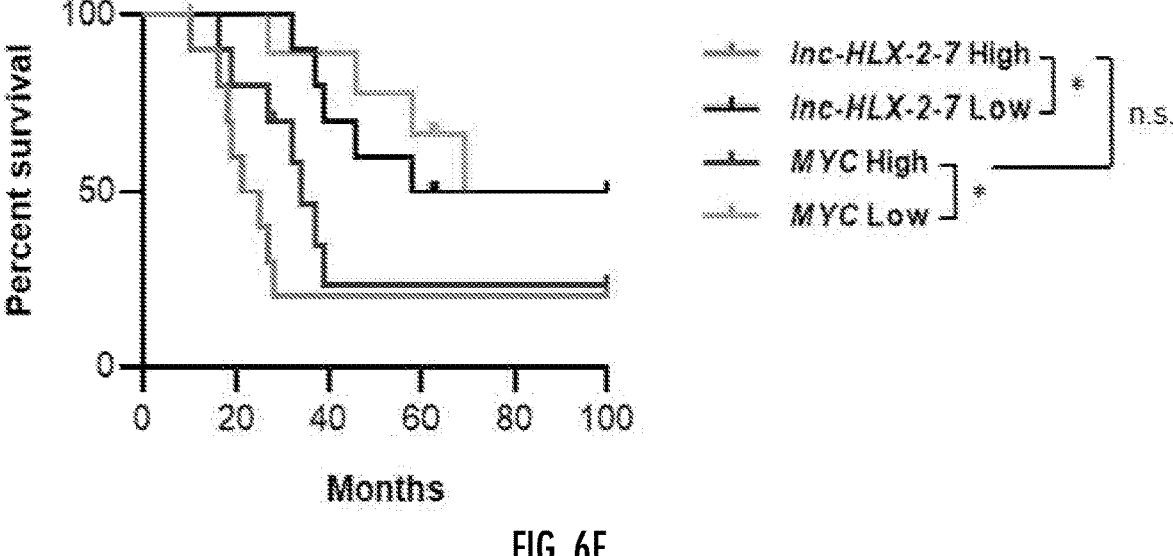
Figure 12A:
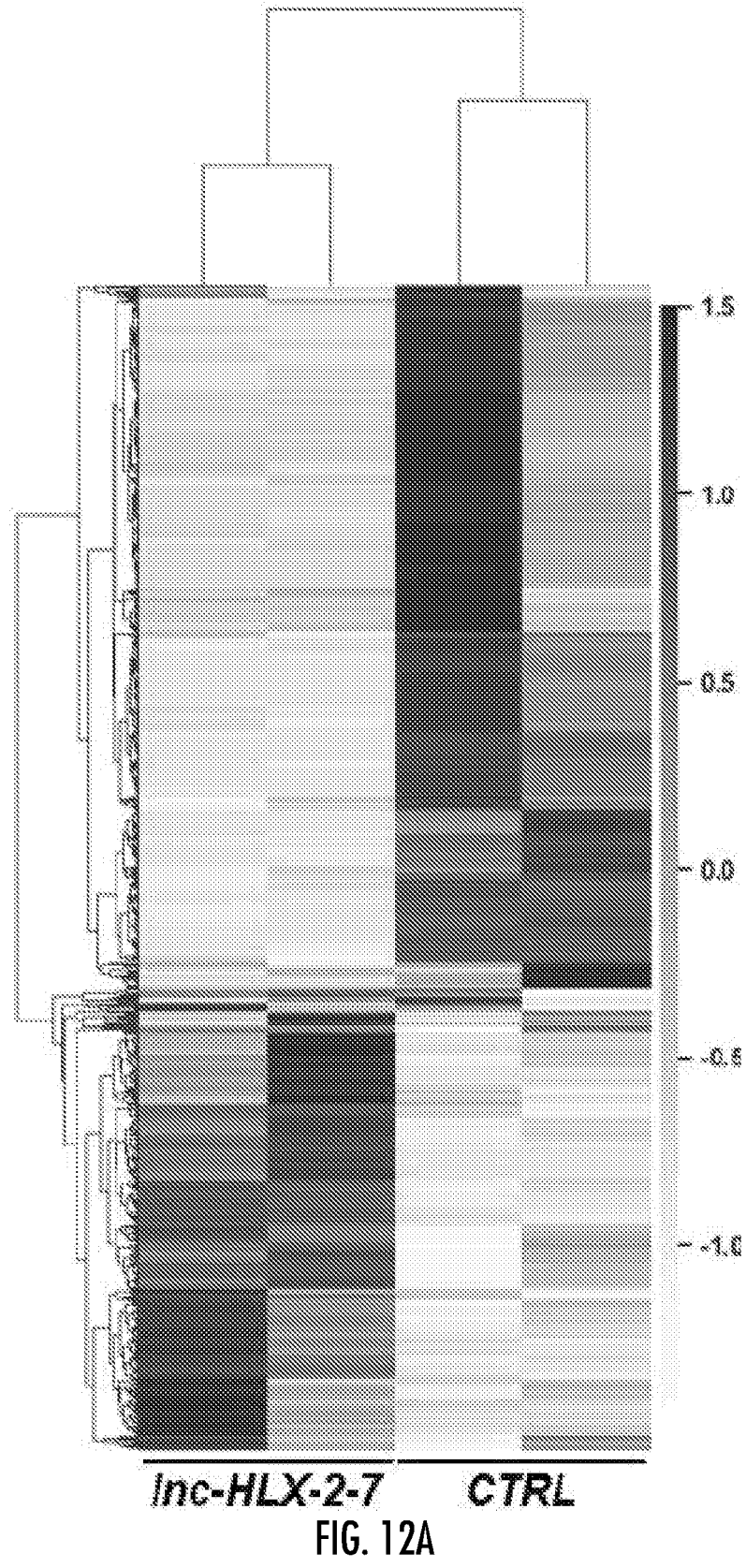
Figure 13:
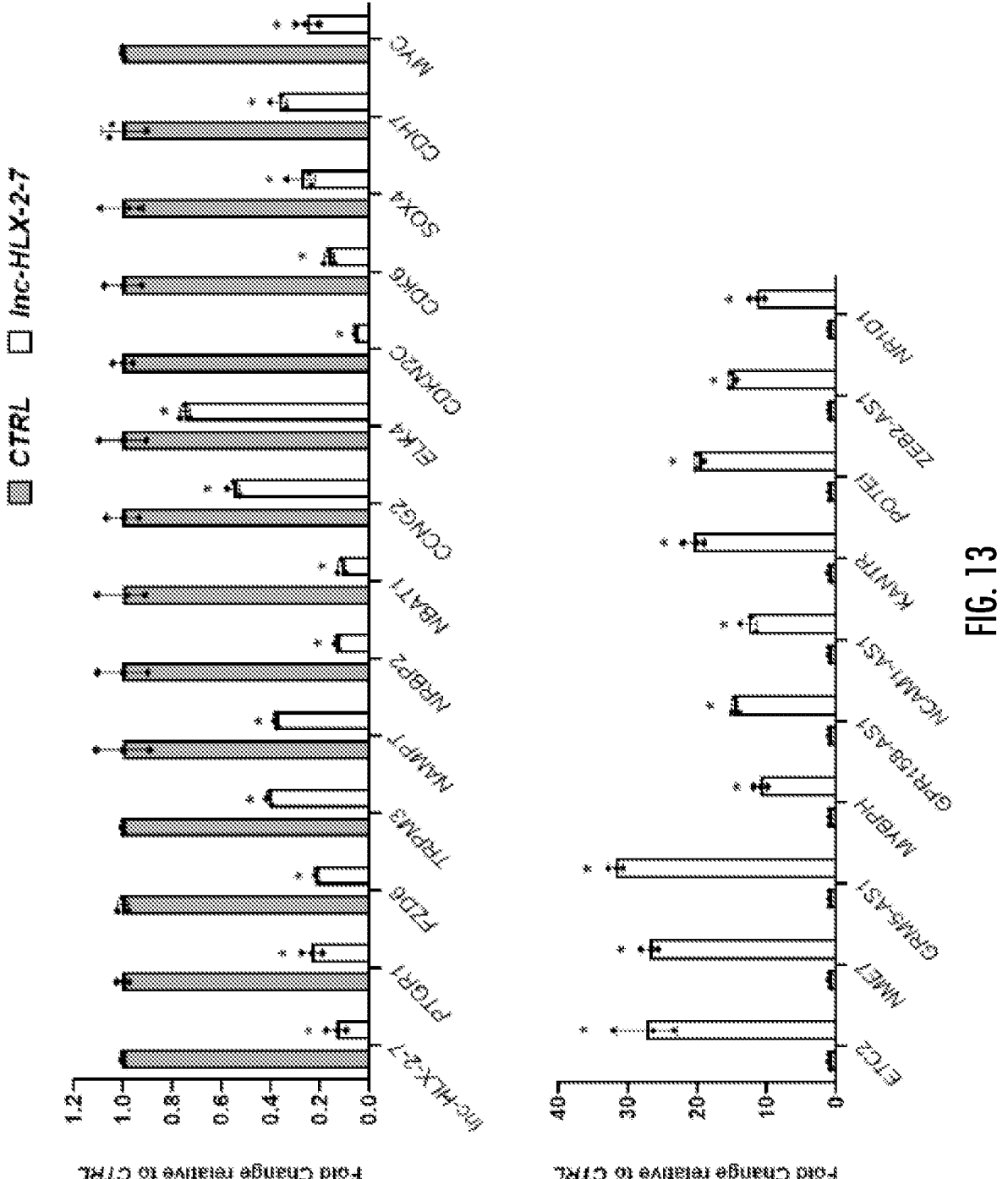
FIG. 13. qPCR validation of D425 Med xenograft RNA-sequencing data. Expression levels of lnc-HLX-2-7, PTGR1, FDZ6, TRPM, NAMPT, NRBP2, NBAT1, CCNG2, ELK4, CDKN2C, CDK6, SOX4, CHD7, MYC, ETC2, NME7, GRA15-AS1, MYBPH, GPR158-AS1, NCAM1-AS1, KANTR, POTEI, ZEB2-AS1, and NR1D1 were examined by qPCR in D425 Med xenografts. Relative expression levels compared with those in the CTRL tumors are indicated on the y-axis (n=3). Error bars indicate s.e.m. *p<0.01, Student's t-test.
Figure 14:
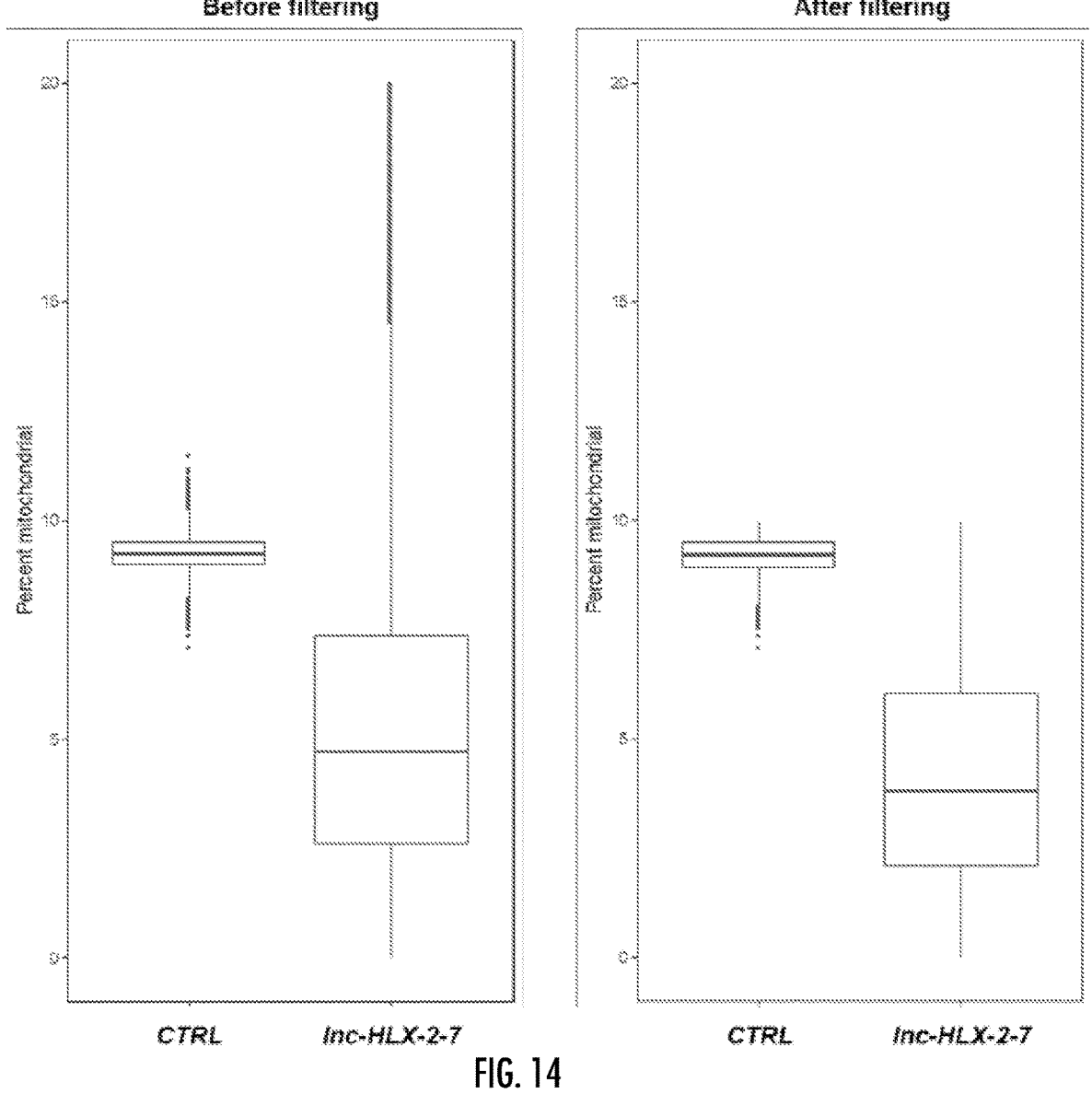
FIG. 14. Boxplots showing the distribution of percentage of reads emanating from mitochondrial genes before and after filtering cells based on mitochondrial content. Cells were filtered for <10% mitochondrial percentage prior to analysis using Seurat and Monocle3.
Figure 15:
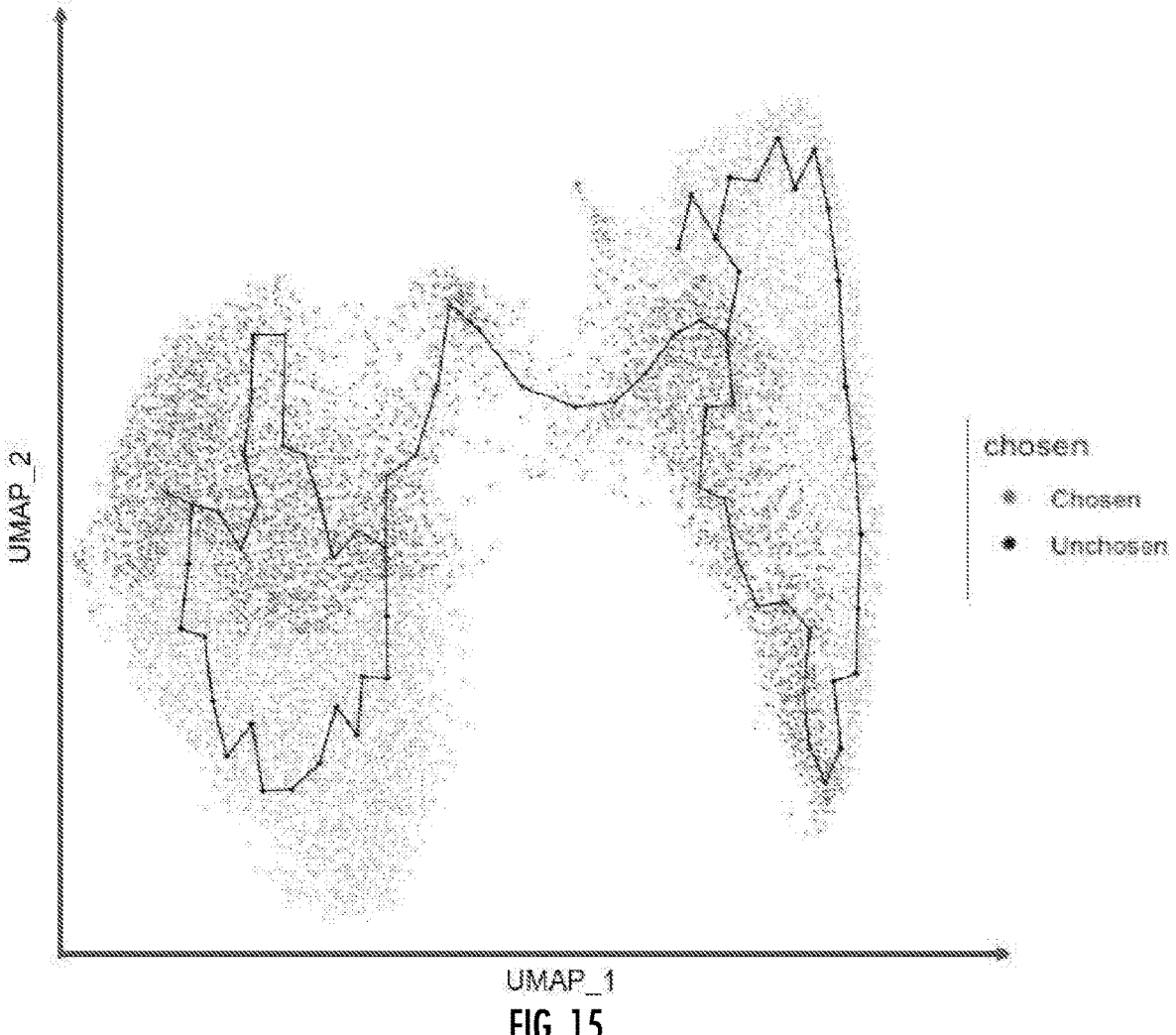
FIG. 15. Graph path corresponding to transition of cells from cluster 1 through 5. Selected cells (in purple) along a selected trajectory for pseudotemporal graph test to determine significant genes that vary along the chosen path. The UMAP space corresponds to FIG. 5D.
Figure 16A:
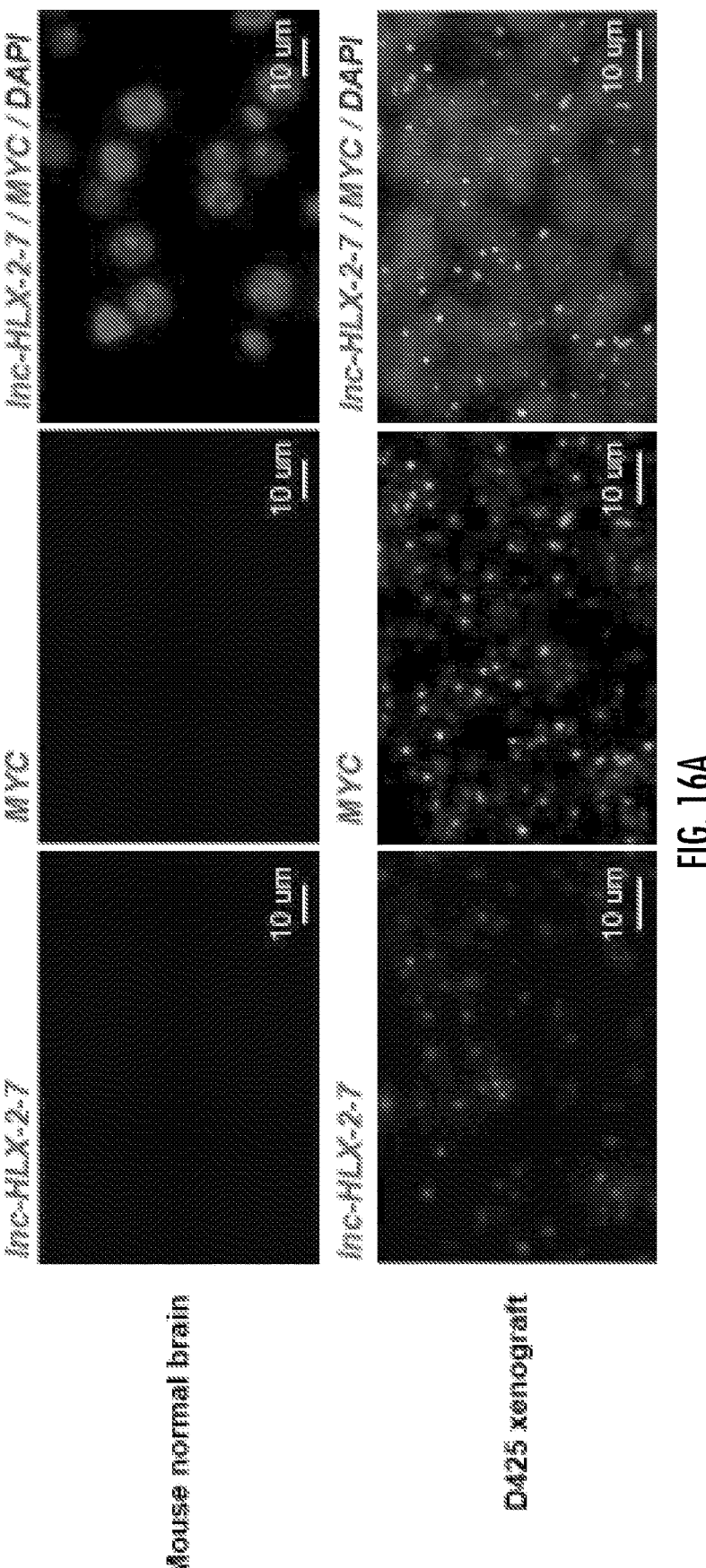
FIG. 16A-16B. Confirmation of the specificity of the lnc-HLX-2-7 probe.
Figure 16B:
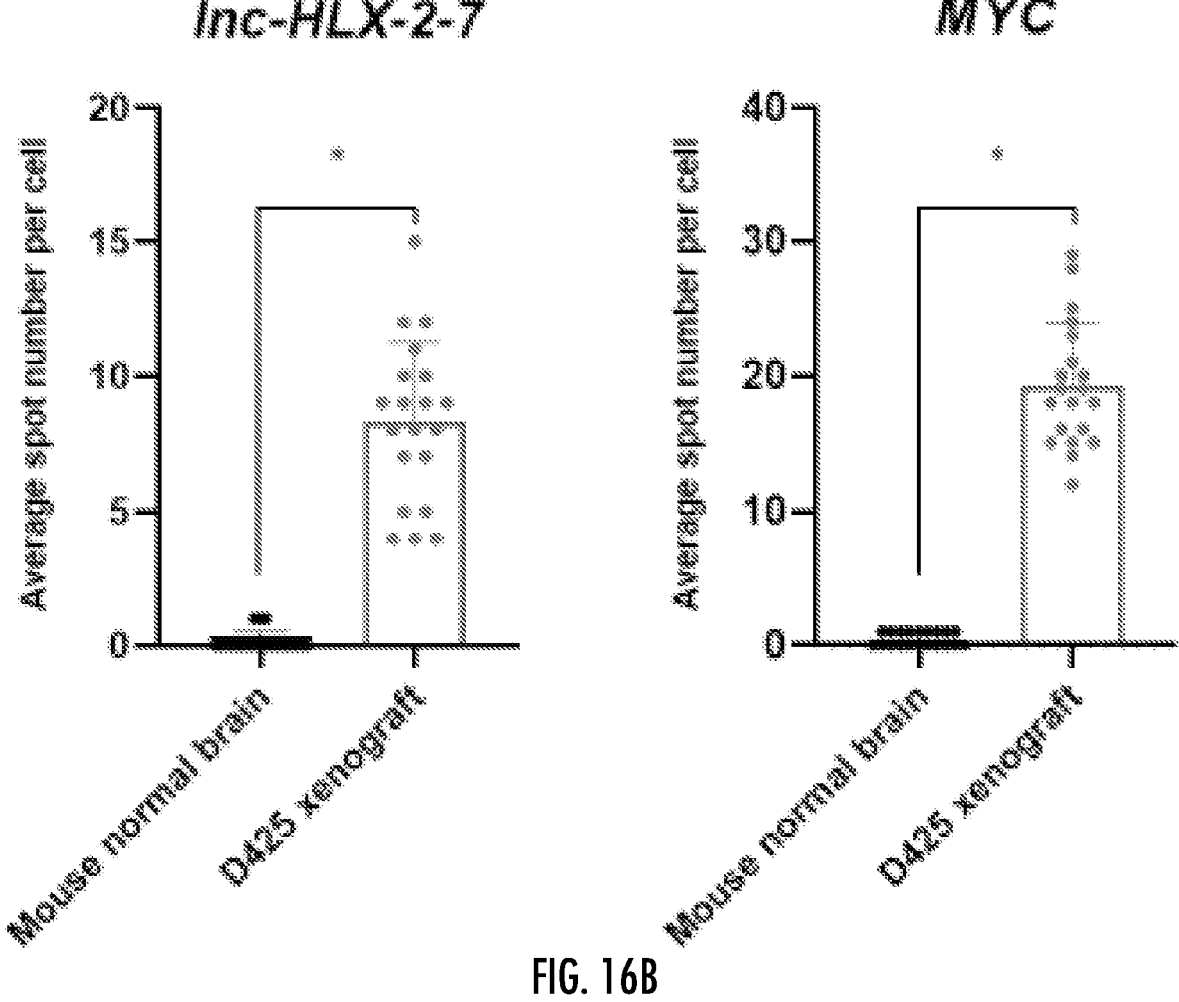
Figures 17A, 17B:
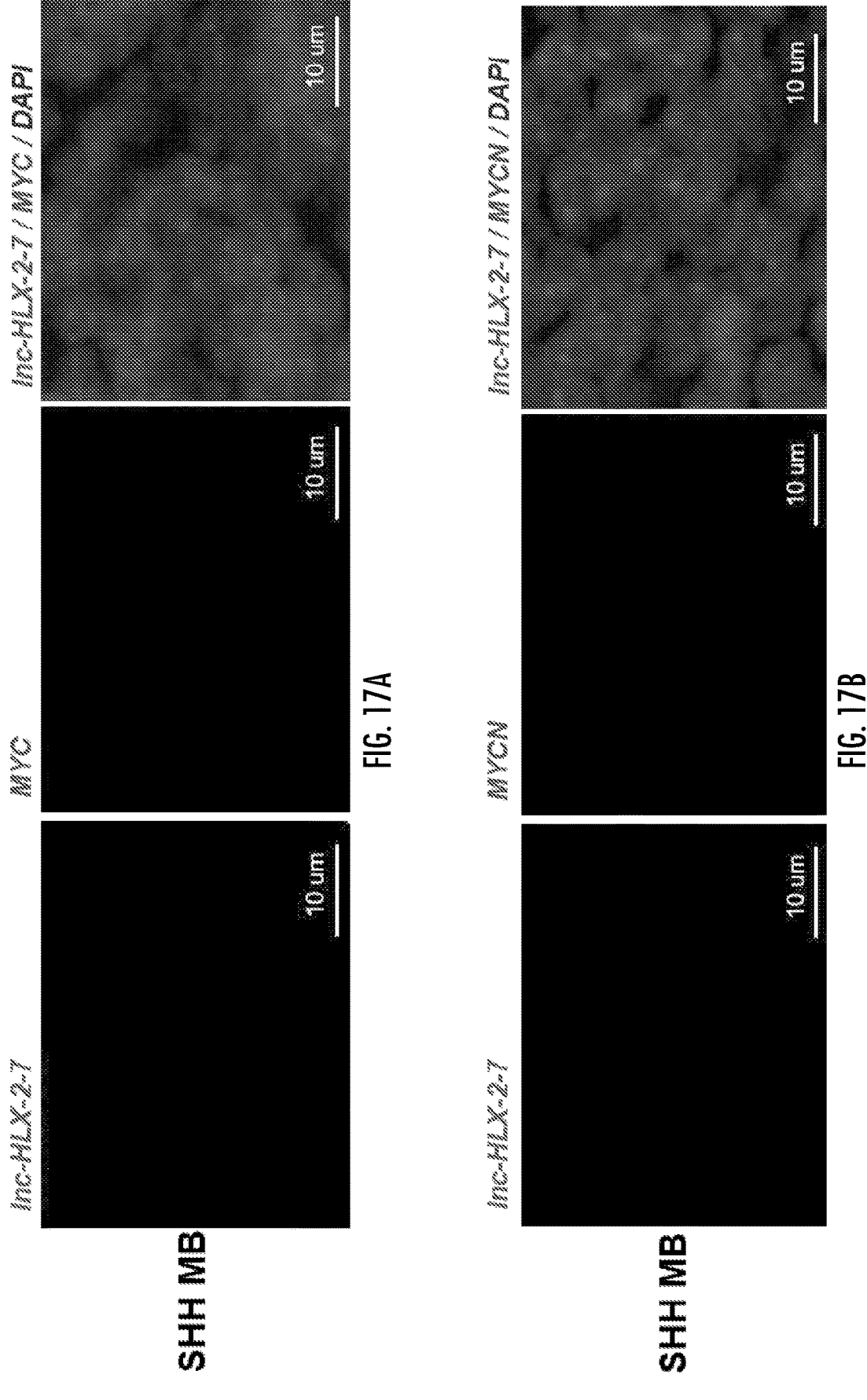
Figure 18:
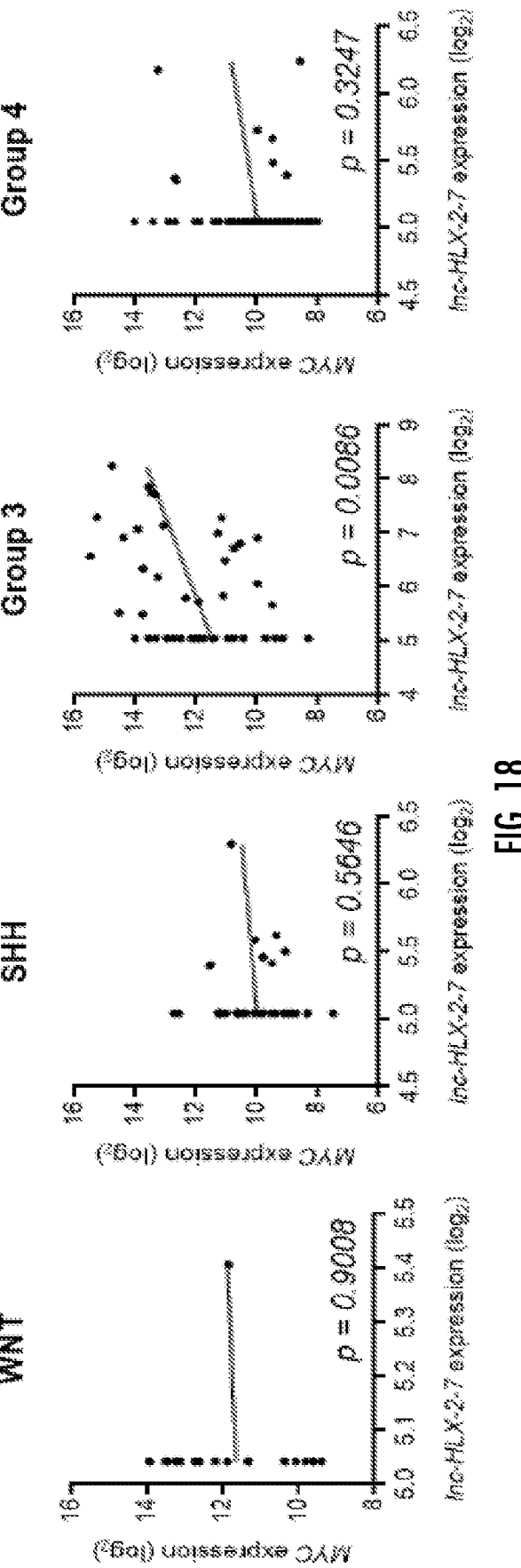
FIG. 18. Expression analysis of lnc-HLX-2-7 and MYC in clinical MB samples. Correlation between lnc-HLX-2-7 and MYC expression in clinical MB samples. Data were obtained from RNA sequencing data from 175 MB patients (ICGC). Each comparison is performed between the genes indicated on the x- and y-axes, respectively.
Figure 19:
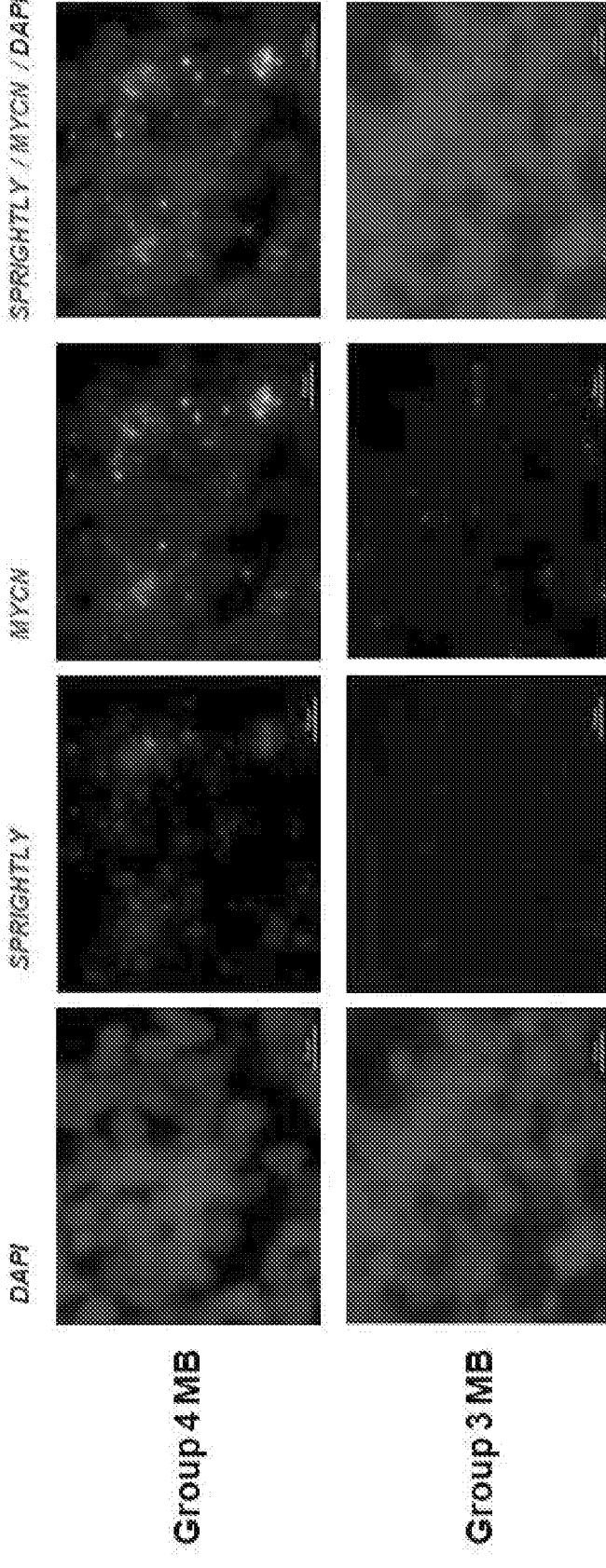
FIG. 19. Spry4-IT1 ("SPRIGHTLY"). RNA is expressed in medulloblastoma group 4 patient samples, but not in group 3. Sprightly (red), MYCN (green) are visualized in FFPE samples in group 4, but not in group 3. DAPI (blue) is stained to depict the nuclei. The control does not show the expression of either Sprightly or MYCN.

RNA sequencing detects lnc-HLX-2-7 interacting genes and pathways in group 3 MBs. To gain further insights into the functional significance of lnc-HLX-2-7, gene expression was measured by RNA-seq in D425 Med-lnc-HLX-2-7-sgRNA cells and in xenografts derived from them. Among 1033 genes with a significant change in expression (FDR<0.05), 484 genes were upregulated and 549 genes were downregulated in cultured D425 Med-lnc-HLX-2-7-sgRNA cells (FIG. 12A). Ingenuity Pathway Analysis (IPA) revealed that lnc-HLX-2-7 knockdown preferentially affected genes associated with cell death (FIG. 12B). Of note, upstream regulator analysis showed that these genes contribute to important cancer pathways including MYC, KRAS, HIF1A, and EGFR signaling (FIG. 12C). In xenografts, among 540 genes with a significant change in expression (FDR<0.05), 409 genes were upregulated and 131 genes were downregulated (FIG. 5A). Differentially expressed genes detected by RNA-seq and pathway analysis were validated by qRT-PCR (FIG. 13). IPA analysis revealed that lnc-HLX-2-7 knockdown preferentially regulated genes associated with cell viability (FIG. 5B). Canonical IPA pathway analysis showed that the pathways involved in important energy metabolism (oxidative phosphorylation, mitochondrial dysfunction, and sirtuin signaling pathways) were highly modulated by lnc-HLX2-7 (FIG. 5C). Xenograft tumors were further characterized by single-cell RNA-seq. Subsequent to quality control, 3,442 and 6,193 single cells were obtained for D425 and lnc-HLX-2-7 deleted D425 respectively (FIG. 14). Integrated clustering of D425 control and lnc-HLX-2-7 depleted xenografts resulted in 5 clusters of single cells (FIG. 5D). Clusters 1 and 2 were almost entirely from D425 control xenografts, while clusters 3, 4, and 5 were almost exclusively from lnc-HLX-2-7 depleted xenografts (FIG. 5E). The top canonical pathways impacted in lnc-HLX-2-7-depleted single cell populations compared to D425 controls included the oxidative phosphorylation and sirtuin signaling pathways (FIG. 5F), consistent with the bulk RNA-seq data. Based on our earlier result that D425 control and lnc-HLX-2-7 depleted single cells form separate clusters, we performed pseudotemporal ordering of cells using Monocle3[35] to identify genes responsible for the transition from the D425 control to lnc-HLX-2-7-depleted state (FIG. 5G). A graph path corresponding to transition of cells from cluster 1 through 5 was observed (FIG. 15). The top 370 genes contributing to the cell transition were selected based on Moran's I and consisted of important genes involved in the development and malignancy of MB such as MYC, SOX4, CDK6, and CHD7.

lnc-HLX-2-7 expression is specific to group 3 MBs. We next confirmed group 3 specificity by visualizing lnc-HLX-2-7 expression by RNA-FISH in formalin-fixed paraffin-embedded tissue samples from D425 Med mouse xenografts and patients with MB. lnc-HLX-2-7 was expressed in D425 Med mouse xenografts but not normal brain (FIGS. 16A-16B), and lnc-HLX-2-7 was readily detected in all group 3 MB samples but not in group 4 MBs (FIG. 6A, B). Quantitative analysis of the tissues further confirmed significantly higher lnc-HLX-2-7 expression in group 3 MBs compared to group 4 and SHH MBs with high sensitivity (95.0%) and specificity (95.0%, n=20, p<0.01, FIG. 6C and FIG. 17A-17C). Importantly, lnc-HLX-2-7 expression was highly correlated with MY C expression in group 3 MBs (n=20, p<0.01, FIG. 6D). This positive correlation between lnc-HLX-2-7 and MYC expression in group 3 MB was further validated in RNA-seq data from 175 MB patients (FIG. 18). Finally, lnc-HLX-2-7 overexpression was associated with poor patient outcomes and mirrored that of MYC expression in group 3 MB (FIG. 6E). Collectively, our analyses suggest that lnc-HLX-2-7 expression is specific to group 3 MBs and can be detected using an assay readily applicable to the clinical setting.

Discussion

The functions and clinical relevance of lncRNAs in MB are poorly described. Here we provide evidence that the lncRNA lnc-HLX-2-7 is clinically relevant and biologically functional in group 3 MBs. Using publicly available patient-derived RNA-seq datasets, we discovered that lnc-HLX-2-7 expression is particularly high in group 3 MBs compared to other groups. By depleting the expression of lnc-HLX-2-7 by CRISPR/Cas9 and ASOs, we showed both in vitro and in vivo that lnc-HLX-2-7 knockdown reduced proliferation and colony formation and increased apoptosis in MB.

The region encoded by lnc-HLX-2-7 has been reported as a group 3 MB-specific enhancer region.[24] Therefore, ncRNAs transcribed from this region may function as enhancer RNAs (eRNAs), a class of lncRNAs synthesized at enhancers, and may regulate the expression of their surrounding genes. We found that lnc-HLX-2-7 positively regulated the expression of the adjacent HLX gene. Although the mechanism by which lnc-HLX-2-7 regulates HLX remains unclear, lnc-HLX-2-7 may function as an eRNA in this context. HLX has recently been shown to be a key gene mediating BET inhibitor responses and resistance in group 3 MBs.[36] In this study, we discovered that lnc-HLX-2-7 controls HLX expression and contributes to MB cell proliferation, so it is possible that it may influence BET inhibitor resistance. In addition, our results show that the MYC oncogene regulates lnc-HLX-2-7 expression. A recent report suggests that the small molecule JQ1, a BET inhibitor that disrupts interactions with MYC, could be a therapeutic option to treat group 3 MBs.[37] However, group 3 MB tumors may also become resistant to BET inhibitor through mutations in the BRD4 gene, and transcription factors like MYC and HLX are poor therapeutic targets with short half-lives and pleiotropic properties.[38] We postulate that lnc-HLX-2-7 inhibition may provide a novel solution to BET inhibitor resistance or amplify the effects of BET inhibitors, a hypothesis that requires further investigation.

Recent evidence shows that HLX directly regulates several metabolic genes and controls mitochondrial biogenesis.[39] In the present study, we demonstrate that lnc-HLX2-7 modulated oxidative phosphorylation, mitochondrial dysfunction, and sirtuin signaling pathways in intracranial xenograft models. These findings suggest that lnc-HLX-2-7 contributes to the metabolic state of group 3 MBs by regulating HLX expression. This newly discovered link between lnc-HLX-2-7 and metabolism may have important therapeutic implications.

Group 3 and group 4 MBs display clinical and genetic overlap, with similar anatomic location and presence of isochromosome 17q, so it is not currently possible to distinguish them without applying multi-gene expression or methylation profiling. lnc-HLX-2-7 may represent a useful single molecular marker that could distinguish group 3 from group 4 MBs. Furthermore, RNA-FISH using probes targeting lnc-HLX-2-7, a technique readily applicable in clinical laboratories, readily discriminated group 3 from group 4 MBs. It was recently shown through a combined analysis of Group 3 and 4 MBs that they can be subdivided into eight molecular subtypes, designated I to VIII.[20] Subtypes II and III are characterized by amplification of the MYC oncogene and are associated with the poorest prognosis.[40] We found that lnc-HLX-2-7 is specifically expressed in subtype II and III MBs. These findings strongly suggest that lnc-HLX-2-7 may be an ideal prognostic marker in group 3 MBs.

In conclusion, we show that the lncRNA lnc-HLX-2-7 is clinically and functionally relevant in group 3 MBs. Future studies will determine the mechanism by which lnc-HLX-2-7 promotes MB tumorigenesis. Together, our findings support the hypothesis that lncRNAs, and lnc-HLX-2-7 in particular, are functional in human MBs and may offer promising future opportunities for diagnosis and therapy.

REFERENCES

1. Northcott P A, Jones D T, Kool M, et al. Medulloblastomics: the end of the beginning. *Nat Rev Cancer.* 2012; 12(12):818-834.
2. Northcott P A, Shih D J, Peacock J, et al. Subgroup-specific structural variation across 1,000 medulloblastoma genomes. *Nature.* 2012; 488(7409):49-56.
3. Jones D T, Jager N, Kool M, et al. Dissecting the genomic complexity underlying medulloblastoma. *Nature.* 2012; 488(7409):100-105.
4. Taylor M D, Northcott P A, Korshunov A, et al. Molecular subgroups of medulloblastoma: the current consensus. *Acta Neuropathol.* 2012; 123(4):465-472.
5. Wahlestedt C. Targeting long non-coding RNA to therapeutically upregulate gene expression. *Nat Rev Drug Discov.* 2013; 12(6):433-446.
6. Schmitt A M, Chang H Y. Long Noncoding RNAs in Cancer Pathways. *Cancer Cell.* 2016; 29(4):452-463.
7. Quinn J J, Chang H Y. Unique features of long non-coding RNA biogenesis and function. *Nat Rev Genet.* 2016; 17(1):47-62.
8. Khaitan D, Dinger M E, Mazar J, et al. The melanoma-upregulated long noncoding RNA SPRY4-IT1 modulates apoptosis and invasion. *Cancer Res.* 2011; 71(11):3852-3862.
9. Sahakyan A, Yang Y, Plath K. The Role of Xist in X-Chromosome Dosage Compensation. *Trends Cell Biol.* 2018; 28(12):999-1013.
10. Trimarchi T, Bilal E, Ntziachristos P, et al. Genome-wide mapping and characterization of Notch-regulated long noncoding RNAs in acute leukemia. *Cell.* 2014; 158(3):593-606.

11. Katsushima K, Natsume A, Ohka F, et al. Targeting the Notch-regulated non-coding RNA TUG1 for glioma treatment. *Nat Commun.* 2016; 7:13616.
12. Long Y, Wang X, Youmans D T, Cech T R. How do lncRNAs regulate transcription? *Sci Adv.* 2017; 3(9):eaao2110.
13. Esteller M. Non-coding RNAs in human disease. *Nat Rev Genet.* 2011; 12(12):861-874.
14. Wapinski O, Chang H Y. Long noncoding RNAs and human disease. *Trends Cell Biol.* 2011; 21(6):354-361.
15. Varon M, Levy T, Mazor G, et al. The long noncoding RNA TP73-AS1 promotes tumorigenicity of medulloblastoma cells. *Int J Cancer.* 2019; 145(12):3402-3413.
16. Joshi P, Katsushima K, Zhou R, et al. The therapeutic and diagnostic potential of regulatory noncoding RNAs in medulloblastoma. *Neurooncol Adv.* 2019; 1(1):vdz023.
17. Zhang Y, Wang T, Wang S, et al. Nkx2-2as Suppression Contributes to the Pathogenesis of Sonic Hedgehog Medulloblastoma. *Cancer Res.* 2018; 78(4):962-973.
18. Gao R, Zhang R, Zhang C, Zhao L, Zhang Y. Long noncoding RNA CCAT1 promotes cell proliferation and metastasis in human medulloblastoma via MAPK pathway. *Tumori.* 2018; 104(1):43-50.
19. Iyer M K, Niknafs Y S, Malik R, et al. The landscape of long noncoding RNAs in the human transcriptome. *Nat Genet.* 2015; 47(3):199-208.
20. Northcott P A, Buchhalter I, Morrissy A S, et al. The whole-genome landscape of medulloblastoma subtypes. *Nature.* 2017; 547(7663):311-317.
21. Lee B, Sahoo A, Marchica J, et al. The long noncoding RNA SPRIGHTLY acts as an intranuclear organizing hub for pre-mRNA molecules. *Sci Adv.* 2017; 3(5):e1602505-e1602505.
22. Uszczynska-Ratajczak B, Lagarde J, Frankish A, Guigo R, Johnson R. Towards a complete map of the human long non-coding RNA transcriptome. *Nat Rev Genet.* 2018; 19(9):535-548.
23. Joshi P, Perera R J. In silico analysis of long non-coding RNAs in medulloblastoma and its subgroups. *Neurobiology of disease.* 2020:104873.
24. Lin C Y, Erkek S, Tong Y, et al. Active medulloblastoma enhancers reveal subgroup-specific cellular origins. *Nature.* 2016; 530:57.
25. Engreitz J M, Haines J E, Perez E M, et al. Local regulation of gene expression by lncRNA promoters, transcription and splicing. *Nature.* 2016; 539(7629):452-455.
26. Joung J, Engreitz J M, Konermann S, et al. Genome-scale activation screen identifies a lncRNA locus regulating a gene neighbourhood. *Nature.* 2017; 548(7667):343-346.
27. Toiber D, Leprivier G, Rotblat B. Long noncoding RNA: noncoding and not coded. *Cell Death Discov.* 2017; 3:16104.
28. Cavalli F M G, Remke M, Rampasek L, et al. Intertumoral Heterogeneity within Medulloblastoma Subgroups. *Cancer Cell.* 2017; 31(6):737-754.e736.
29. Mathelier A, Wasserman W W. The next generation of transcription factor binding site prediction. *PLoS computational biology.* 2013; 9(9).
30. Bolin S, Borgenvik A, Persson C U, et al. Combined BET bromodomain and CDK2 inhibition in MYC-driven medulloblastoma. *Oncogene.* 2018; 37(21):2850-2862.
31. Venkataraman S, Alimova I, Balakrishnan I, et al. Inhibition of BRD4 attenuates tumor cell self-renewal and suppresses stem cell signaling in MYC driven medulloblastoma. *Oncotarget.* 2014; 5(9):2355-2371.

32. Henssen A, Thor T, Odersky A, et al. BET bromodomain protein inhibition is a therapeutic option for medulloblastoma. *Oncotarget.* 2013; 4(11):2080-2095.

33. Shi X, Liu C, Liu B, Chen J, Wu X, Gong W. JQ1: a novel potential therapeutic target. *Pharmazie.* 2018; 73(9):491-493.

34. Delmore J E, Issa G C, Lemieux M E, et al. BET bromodomain inhibition as a therapeutic strategy to target c-Myc. *Cell.* 2011; 146(6):904-917.

35. Trapnell C, Cacchiarelli D, Grimsby J, et al. The dynamics and regulators of cell fate decisions are revealed by pseudotemporal ordering of single cells. *Nat Biotechnol.* 2014; 32(4):381-386.

36. Bandopadhayay P, Piccioni F, O'Rourke R, et al. Neuronal differentiation and cell-cycle programs mediate response to BET-bromodomain inhibition in MYC-driven medulloblastoma. *Nat Commun.* 2019; 10(1):2400.

37. Bandopadhayay P, Bergthold G, Nguyen B, et al. BET bromodomain inhibition of MYC-amplified medulloblastoma. *Clin Cancer Res.* 2014; 20(4):912-925.

38. McKeown M R, Bradner J E. Therapeutic strategies to inhibit MYC. *Cold Spring Harb Perspect Med.* 2014; 4(10).

39. Piragyte I, Clapes T, Polyzou A, et al. A metabolic interplay coordinated by HLX regulates myeloid differentiation and AML through partly overlapping pathways. *Nature communications.* 2018; 9(1):3090.

40. Sharma T, Schwalbe E C, Williamson D, et al. Second-generation molecular subgrouping of medulloblastoma: an international meta-analysis of Group 3 and Group 4 subtypes. *Acta Neuropathol.* 2019; 138(2):309-326.

Supplementary Materials and Methods

Isolation of single cells from orthotopic xenografts. Thirty days after of the injection of D425 Med cells and D425 Med cells with lnc-HLX-2-7 deleted into the cerebellums, tumors were harvested and dissociated using a brain tumor dissociation kit (Miltenyi Biotech Inc., Auburn, CA) according to the manufacturer's protocol. To enrich human cells, mouse cells were depleted from the dissociated tumor cells using a mouse cell depletion kit (Miltenyi Biotech Inc.). The dissociated tumor cells were further sorted using a FACSAria (Beckton Dickinson, Franklin Lakes, NJ) to obtain live and singlet cells. The cells were resuspended in DPBS with 0.04% BSA to a final concentration of $1 \times 10^6$ cells per ml.

Processing of scRNA-seq data. Single-cell RNA-seq samples were classified into host and graft reads using XenoCell 1 and Xenome v1.0.1 2. The proportions of graft and host reads were 92.25% and 0.43% for D425, and 86.54% and 2.96% for lnc-HLX2-7 deleted D425 respectively. The remaining reads were classified as both, neither, or ambiguous. FASTQ files for graft were aligned to human genome hg38, indexed with GENCODE human annotations v34 3 and augmented with lncRNA annotations from LNCipedia v5.24, using 10× Genomics cellranger count (https://support.10xgenomics.com/) and STAR v 2.7.0d_0221 5. For downstream integrated analysis, both samples were combined and normalized for the number of mapped reads per cell across libraries using 10× Genomics cellranger aggr function. 5,547 and 10,039 cells were detected for D425 and lnc-HLX-2-7 deleted D425 respectively with post-normalization mean number of 18,034 reads per cell and median of 960 genes detected per cell.

Quality control and clustering analysis of scRNA-seq. Quality control and clustering of scRNA-seq data were performed using Seurat v3.1.26 in R v3.6.1. Low quality and doublet cells were filtered by selecting cells with <10% mitochondrial percentage and expressing 200-2500 genes. 3,442 and 6,193 cells were retained for D425 Med and lnc-HLX-2-7 deleted-xenograft samples after filtering. The count matrices for D425 and lnc-HLX-2-deleted xenograft were normalized and integrated using FindIntegrationAnchors and IntegrateData functions. Principle component analysis (PCA) was subsequently performed. For combined clustering, 15 PCs with resolution=0.5 were used to obtain 5 clusters. The marker genes associated with each cluster were identified by finding differentially expressed features across clusters and using log 2 fold change cutoff of ±0.2 and adjusted p-value of 0.05.

Supplementary References

1. Cheloni S, Hillje R, Luzi L, Pelicci P G, Gatti E. XenoCell: classification of cellular barcodes in single cell experiments from xenograft samples. *bioRxiv.* 2019.

2. Conway T, Wazny J, Bromage A, et al. Xenome—a tool for classifying reads from xenograft samples. *Bioinformatics.* 2012; 28(12):i172-178.

3. Frankish A, Diekhans M, Ferreira A M, et al. GENCODE reference annotation for the human and mouse genomes. *Nucleic Acids Res.* 2019; 47(D1):D766-D773.

4. Volders P-J, Anckaert J, Verheggen K, et al. LNCipedia 5: towards a reference set of human long non-coding RNAs. *Nucleic Acids Res.* 2019; 47(D1):D135-D139.

5. Dobin A, Davis C A, Schlesinger F, et al. STAR: ultrafast universal RNA-seq aligner. *Bioinformatics.* 2013; 29(1):15-21.

6. Butler A, Hoffman P, Smibert P, Papalexi E, Satija R. Integrating single-cell transcriptomic data across different conditions, technologies, and species. *Nat Biotechnol.* 2018; 36(5):411-420.

TABLE 1

| lncHLX2-7 Probes | | | | | |
|---|---|---|---|---|---|
| ACCESSION | NAME | FUNCTION | PROBE REGION | SEQUENCE | SEQ ID NO |
| GS10906 | Inc_HLX2_71-1R | LE | 19-39 bp | ccagacataaactcgccaagc | 3 |
| GS10906 | Inc_HLX2_72-1R | LE | 40-57 bp | ccgcatgtgtccaggcac | 4 |
| GS10906 | Inc_HLX2_73-1R | BL | 58-83 bp | gtgtgtgtgtgtgtgtgtgtttattc | 5 |
| GS10906 | Inc_HLX2_74-1R | BL | 84-108 bp | gcagtaacatcgaatgtgtgtgtgt | 6 |
| GS10906 | Inc_HLX2_75-1R | BL | 109-132 bp | aaaaaaatgaatggatgaaggaat | 7 |

TABLE 1-continued

| lncHLX2-7 Probes | | | | | |
|---|---|---|---|---|---|
| ACCESSION | NAME | FUNCTION | PROBE REGION | SEQUENCE | SEQ ID NO |
| GS10906 | Inc_HLX2_76-1R | LE | 133-155 bp | ggatccccataaatactgcaatg | 8 |
| GS10906 | Inc_HLX2_77-1R | LE | 156-179 bp | tctctatggtgcaaacactcacaa | 9 |
| GS10906 | Inc_HLX2_78-1R | LE | 180-206 bp | tggttaatgcttagtcaaatactttt | 10 |
| GS10906 | Inc_HLX2_79-1R | LE | 207-231 bp | acaaacactgatctcttagctggaa | 11 |
| GS10906 | Inc_HLX2_710-1R | LE | 232-255 bp | caaccacctcagctattttgaatg | 12 |
| GS10906 | Inc_HLX2_711-1R | LE | 256-277 bp | gggaatactggctgtcctctcc | 13 |
| GS10906 | Inc_HLX2_712-1R | LE | 278-303 bp | cctaggaaactaataaacctcttttg | 14 |
| GS10906 | Inc_HLX2_713-1R | LE | 304-327 bp | gtctgtgtcaatttgtgacagcag | 15 |
| GS10906 | Inc_HLX2_714-1R | LE | 328-355 bp | acacatttctgttgtttaagtcactaa | 16 |
| GS10906 | Inc_HLX2_715-1R | LE | 356-381 bp | gagaagcagagaatgtagtgacacaa | 17 |
| GS10906 | Inc_HLX2_716-1R | LE | 382-403 bp | cagaagaagagtccatgtgcca | 18 |
| GS10906 | Inc_HLX2_717-1R | LE | 404-426 bp | ggaagacagaggaaaactggatg | 19 |
| GS10906 | Inc_HLX2_718-1R | LE | 427-448 bp | taccacacgcatgcttatgaga | 20 |
| GS10906 | Inc_HLX2_719-1R | LE | 449-468 bp | cctgggtggacgctaaatgc | 21 |

LE: Label extenders; CE: Capture oligos; BL: Blocker oligos.

TABLE 2

| SPRY4-IT1 Probes | | | | | |
|---|---|---|---|---|---|
| ACCESSION | NAME | FUNCTION | PROBE REGION | SEQUENCE | SEQ ID NO |
| NR_131221 | SPRY4-IT11-4R | LE | 45-66 bp | ggcagatcacttgaggtcagga | 22 |
| NR_131221 | SPRY4-IT12-4R | LE | 67-86 bp | ccttttgggaggccaaggta | 23 |
| NR_131221 | SPRY4-IT13-4R | LE | 87-108 bp | tggctcatgcctgtaatctcag | 24 |
| NR_131221 | SPRY4-IT14-4R | LE | 109-126 bp | aaagaaggcctggcgcag | 25 |
| NR_131221 | SPRY4-IT15-4R | BL | 127-153 bp | aaaaaaaaagaaagaaaaaaagaaaag | 26 |
| NR_131221 | SPRY4-IT16-4R | LE | 154-177 bp | cagcacagctaaatgatgtctcaa | 27 |
| NR_131221 | SPRY4-IT17-4R | LE | 178-199 bp | agctgcctatttaagaacccct | 28 |
| NR_131221 | SPRY4-IT18-4R | LE | 200-224 bp | gctgacaaaggaaaacaattttctg | 29 |
| NR_131221 | SPRY4-IT19-4R | LE | 225-248 bp | aagagcctctgctgaatttatgtg | 30 |
| NR_131221 | SPRY4-IT110-4R | LE | 249-266 bp | caccagcagggaccctcc | 31 |
| NR_131221 | SPRY4-IT111-4R | LE | 267-284 bp | actgctggcctcacccct | 32 |
| NR_131221 | SPRY4-IT112-4R | LE | 285-307 bp | agcaaaaaccaaatcagagttcc | 33 |
| NR_131221 | SPRY4-IT113-4R | LE | 308-329 bp | gattcctttcaaccaccagctc | 34 |
| NR_131221 | SPRY4-IT114-4R | LE | 330-354 bp | ccctattataaccccgatgtagtag | 35 |
| NR_131221 | SPRY4-IT115-4R | LE | 355-380 bp | actgggcatattctaaaatgtatctt | 36 |
| NR_131221 | SPRY4-IT116-4R | LE | 381-398 bp | gcagcatccgatggctcc | 37 |
| NR_131221 | SPRY4-IT117-4R | LE | 399-417 bp | ttggctctctggggacgat | 38 |

TABLE 2-continued

SPRY4-IT1 Probes

| ACCESSION NAME | FUNCTION | PROBE REGION | SEQUENCE | SEQ ID NO |
|---|---|---|---|---|
| NR_131221 SPRY4-IT118-4R | LE | 418-436 bp | gagcttggcccacgatgac | 39 |
| NR_131221 SPRY4-IT119-4R | LE | 437-454 bp | ggccagacatggggatgg | 40 |
| NR_131221 SPRY4-IT120-4R | LE | 455-473 bp | catctgggcctgcagttga | 41 |
| NR_131221 SPRY4-IT121-4R | LE | 474-493 bp | cctccagaggcagctgtcaa | 42 |
| NR_131221 SPRY4-IT122-4R | LE | 494-514 bp | gcattcacaggctcccataac | 43 |
| NR_131221 SPRY4-IT123-4R | LE | 515-533 bp | gcaggcaatggggatgttg | 44 |
| NR_131221 SPRY4-IT124-4R | LE | 534-550 bp | ggatgggagcagccgct | 45 |
| NR_131221 SPRY4-IT125-4R | LE | 551-569 bp | aagtcccaccaggaagcca | 46 |
| NR_131221 SPRY4-IT126-4R | LE | 570-590 bp | cagattccccaattcatggaa | 47 |
| NR_131221 SPRY4-IT127-4R | LE | 591-613 bp | taataggccttggaatcagaaag | 48 |
| NR_131221 SPRY4-IT128-4R | LE | 614-634 bp | atgggcaatgctcagaaattt | 49 |
| NR_131221 SPRY4-IT129-4R | LE | 635-660 bp | catgtcctacagataaagcaaaagaa | 50 |

TABLE 3

MYC Probes

| ACCESSION NAME | FUNCTION | PROBE REGION | SEQUENCE | SEQ ID NO |
|---|---|---|---|---|
| NM_002467 MYC1-6R | LE | 566-583 bp | cgttgaggggcatcgtcg | 51 |
| NM_002467 MYC2-6R | LE | 584-607 bp | catagttcctgttggtgaagctaa | 52 |
| NM_002467 MYC3-6R | LE | 608-628 bp | gcaccgagtcgtagtcgaggt | 53 |
| NM_002467 MYC4-6R | LE | 629-649 bp | cgtcgcagtagaaatacggct | 54 |
| NM_002467 MYC5-6R | LE | 650-672 bp | ctgctggtagaagttctcctcct | 55 |
| NM_002467 MYC6-6R | LE | 673-691 bp | gcagctcgctctgctgctg | 56 |
| NM_002467 MYC7-6R | BL | 692-704 bp | ggcgccgggggct | 57 |
| NM_002467 MYC8-6R | BL | 705-726 bp | tttcttccagatatcctcgctg | 58 |
| NM_002467 MYC9-6R | LE | 727-744 bp | ggtgggcagcagctcgaa | 59 |
| NM_002467 MYC10-6R | LE | 745-761 bp | ctaggggacaggggcgg | 60 |
| NM_002467 MYC11-6R | BL | 762-774 bp | cccggagcggcgg | 61 |
| NM_002467 MYC12-6R | LE | 775-793 bp | cgtaggagggcgagcagag | 62 |
| NM_002467 MYC13-6R | LE | 794-813 bp | ggagaagggtgtgaccgcaa | 63 |
| NM_002467 MYC14-6R | BL | 814-832 bp | cgtcgttgtctccccgaag | 64 |
| NM_002467 MYC17-6R | BL | 865-884 bp | agctcggtcaccatctccag | 65 |
| NM_002467 MYC18-6R | LE | 885-904 bp | tcaccatgtctcctcccagc | 66 |
| NM_002467 MYC19-6R | LE | 905-925 bp | ggtcgcagatgaaactctggt | 67 |
| NM_002467 MYC20-6R | LE | 926-945 bp | gatgaaggtctcgtcgtccg | 68 |
| NM_002467 MYC21-6R | LE | 946-969 bp | acagtcctggatgatgatgttttt | 69 |
| NM_002467 MYC22-6R | BL | 970-988 bp | ccgagaagccgctccacat | 70 |
| NM_002467 MYC30-6R | BL | 1111-1124 bp | gcggcggcgctcag | 71 |

TABLE 3-continued

| | | | | MYC Probes | |
|---|---|---|---|---|---|
| ACCESSION NAME | FUNCTION | PROBE REGION | SEQUENCE | | SEQ ID NO |
| NM_002467 MYC31-6R | LE | 1125-1144 bp | aggggtcgatgcactctgag | | 72 |
| NM_002467 MYC32-6R | LE | 1145-1163 bp | gggtaggggaagaccaccg | | 73 |
| NM_002467 MYC33-6R | BL | 1164-1183 bp | gcgagctgctgtcgttgaga | | 74 |
| NM_002467 MYC34-6R | LE | 1184-1200 bp | cgaggcgcaggacttgg | | 75 |
| NM_002467 MYC35-6R | LE | 1201-1220 bp | gagaaggcgctggagtcttg | | 76 |
| NM_002467 MYC36-6R | LE | 1221-1240 bp | gcagagaatccgaggacgga | | 77 |
| NM_002467 MYC37-6R | LE | 1241-1260 bp | ggaggactccgtcgaggaga | | 78 |
| NM_002467 MYC38-6R | BL | 1261-1275 bp | ggggctgccctgcgg | | 79 |
| NM_002467 MYC39-6R | BL | 1276-1293 bp | atggagcaccaggggctc | | 80 |
| NM_002467 MYC40-6R | LE | 1294-1311 bp | ggtgggcggtgtctcctc | | 81 |
| NM_002467 MYC41-6R | LE | 1312-1331 bp | tcctcagagtcgctgctggt | | 82 |
| NM_002467 MYC42-6R | LE | 1332-1356 bp | gatttcttcctcatcttcttgttcc | | 83 |
| NM_002467 MYC43-6R | LE | 1357-1380 bp | cctcttttccacagaaacaacatc | | 84 |
| NM_002467 MYC44-6R | LE | 1381-1399 bp | accttttgccaggagcctg | | 85 |
| NM_002467 MYC45-6R | LE | 1400-1422 bp | agcagaaggtgatccagactctg | | 86 |
| NM_002467 MYC46-6R | LE | 1423-1441 bp | gaggtttgctgtggcctcc | | 87 |
| NM_002467 MYC47-6R | LE | 1442-1461 bp | gaggaccagtgggctgtgag | | 88 |
| NM_002467 MYC48-6R | LE | 1462-1481 bp | gtggagacgtggcacctctt | | 89 |
| NM_002467 MYC49-6R | LE | 1482-1502 bp | gctgcgtagttgtgctgatgt | | 90 |
| NM_002467 MYC50-6R | LE | 1503-1520 bp | ttccgagtggagggaggc | | 91 |
| NM_002467 MYC51-6R | LE | 1521-1541 bp | ctcttggcagcaggatagtcc | | 92 |
| NM_002467 MYC52-6R | LE | 1542-1565 bp | actctgacactgtccaacttgacc | | 93 |
| NM_002467 MYC53-6R | LE | 1566-1588 bp | ggttgttgctgatctgtctcagg | | 94 |
| NM_002467 MYC54-6R | LE | 1589-1606 bp | tggggctggtgcattttc | | 95 |
| NM_002467 MYC55-6R | LE | 1607-1624 bp | cctcggtgtccgaggacc | | 96 |
| NM_002467 MYC56-6R | LE | 1625-1646 bp | tgtgttcgcctcttgacattct | | 97 |
| NM_002467 MYC57-6R | LE | 1647-1664 bp | tggcgctccaagacgttg | | 98 |
| NM_002467 MYC58-6R | BL | 1665-1686 bp | ccgttttagctcgttcctcctc | | 99 |
| NM_002467 MYC62-6R | BL | 1744-1768 bp | tggctttttttaaggataactacctt | | 100 |
| NM_002467 MYC63-6R | LE | 1769-1789 bp | ggacggacaggatgtatgctg | | 101 |
| NM_002467 MYC64-6R | LE | 1790-1810 bp | tgagcttttgctcctctgctt | | 102 |

TABLE 4

| | | | | SEQ ID NO |
|---|---|---|---|---|
| ACCESSION NAME | FUNCTION | PROBE REGION | SEQUENCE | |
| NM_005378 MYCN1-6R | LE | 1357-1375 bp | gctcgctggactgagccct | 103 |
| NM_005378 MYCN2-6R | LE | 1376-1396 bp | gaaggcatcgtttgaggatca | 104 |
| NM_005378 MYCN3-6R | BL | 1397-1415 bp | ttgtgctgctggtggatgg | 105 |
| NM_005378 MYCN6-6R | BL | 1456-1478 bp | ctctttatcttcttctgtggggg | 106 |
| NM_005378 MYCN7-6R | LE | 1479-1494 bp | acgtggggacgcctcg | 107 |
| NM_005378 MYCN8-6R | LE | 1495-1514 bp | gggatgacactcttgagcgg | 108 |
| NM_005378 MYCN9-6R | BL | 1515-1535 bp | ctcaagctcttagcctttggg | 109 |
| NM_005378 MYCN10-6R | BL | 1536-1554 bp | cgagtcagagtttcggggg | 110 |
| NM_005378 MYCN11-6R | LE | 1555-1573 bp | tgcgacgctcactgtcctc | ill |
| NM_005378 MYCN12-6R | LE | 1574-1594 bp | gctccaggatgttgtggtttc | 112 |
| NM_005378 MYCN13-6R | BL | 1595-1609 bp | cgttgcggcgctggc | 113 |
| NM_005378 MYCN14-6R | LE | 1610-1630 bp | tgagaaagctggaccgaaggt | 114 |
| NM_005378 MYCN15-6R | LE | 1631-1648 bp | gcacgtggtccctgagcg | 115 |
| NM_005378 MYCN16-6R | LE | 1649-1672 bp | ccttctcattctttaccaactccg | 116 |
| NM_005378 MYCN17-6R | LE | 1673-1691 bp | aaaatgaccaccttggcgg | 117 |
| NM_005378 MYCN18-6R | LE | 1692-1714 bp | ggacatactcagtggcctttttc | 118 |
| NM_005378 MYCN19-6R | LE | 1715-1732 bp | cctcggcctggagggagt | 119 |
| NM_005378 MYCN20-6R | LE | 1733-1752 bp | ttccagcaaaagctggtgct | 120 |
| NM_005378 MYCN21-6R | LE | 1753-1773 bp | tcttgcctgcaattttttcctt | 121 |
| NM_005378 MYCN22-6R | LE | 1774-1796 bp | attttctttagcaactgctgctg | 122 |
| NM_005378 MYCN23-6R | LE | 1797-1815 bp | gcaagtccgagcgtgttca | 123 |
| NM_005378 MYCN24-6R | LE | 1816-1838 bp | tgtccagttttgagaagcgtcta | 124 |
| NM_005378 MYCN25-6R | LE | 1839-1860 bp | aaatgtgcaaagtggcagtgac | 125 |
| NM_005378 MYCN26-6R | BL | 1861-1887 bp | cacaatgtttgtttaaaaaaaaaatca | 126 |
| NM_005378 MYCN27-6R | LE | 1888-1914 bp | aaagtaaaccaacattcttaatgtcaa | 127 |
| NM_005378 MYCN28-6R | LE | 1915-1933 bp | tcgacaggggaccgatttg | 128 |
| NM_005378 MYCN29-6R | LE | 1934-1951 bp | gcccacccagagccgaac | 129 |
| NM_005378 MYCN30-6R | LE | 1952-1972 bp | ccccacactggtggtcctact | 130 |
| NM_005378 MYCN31-6R | BL | 1973-1992 bp | tctccaaggtcccagcagaa | 131 |
| NM_005378 MYCN34-6R | BL | 2027-2047 bp | catggaggtgaggtggaggag | 132 |
| NM_005378 MYCN35-6R | LE | 2048-2067 bp | tcaccaacgtttagcgctgt | 133 |
| NM_005378 MYCN36-6R | LE | 2068-2085 bp | cccagaggctcccaaccg | 134 |
| NM_005378 MYCN37-6R | LE | 2086-2108 bp | acacacaaggtgacttcaacagc | 135 |
| NM_005378 MYCN38-6R | LE | 2109-2131 bp | tttctgttgtttggaaacttgga | 136 |
| NM_005378 MYCN39-6R | LE | 2132-2156 bp | caccattttaaaaagaaggaatgac | 137 |
| NM_005378 MYCN40-6R | LE | 2157-2178 bp | gtggcatctgctggaacttaag | 138 |
| NM_005378 MYCN41-6R | LE | 2179-2200 bp | tatcaaatggcaaacccctat | 139 |

TABLE 4-continued

| | | | MYCN Probes | |
|---|---|---|---|---|
| ACCESSION NAME | FUNCTION | PROBE REGION | SEQUENCE | SEQ ID NO |
| NM_005378 MYCN42-6R | LE | 2201-2219 bp | cagaaatgttccccagggg | 140 |
| NM_005378 MYCN43-6R | LE | 2220-2242 bp | ggcggatgtgtcaatggtattta | 141 |
| NM_005378 MYCN44-6R | LE | 2243-2268 bp | tctcattacccaggatgtatacaaaa | 142 |
| NM_005378 MYCN45-6R | LE | 2269-2284 bp | ggccgcaaaagccacc | 143 |
| NM_005378 MYCN46-6R | LE | 2285-2313 bp | acttaggtatgaacttccagtctaatact | 144 |
| NM_005378 MYCN47-6R | BL | 2314-2340 bp | cctcaaacattgaggtattattacagt | 145 |
| NM_005378 MYCN54-6R | BL | 2518-2552 bp | catatatatatagtaaatttctttacaaa agtttc | 146 |
| NM_005378 MYCN55-6R | LE | 2553-2575 bp | gaagaaacaggctaggaaaaagg | 147 |
| NM_005378 MYCN56-6R | LE | 2576-2601 bp | ccaaacatgaacaaatacattaacag | 148 |
| NM_005378 MYCN57-6R | LE | 2602-2624 bp | ttgcatttacccagttctatgca | 149 |
| NM_005378 MYCN58-6R | LE | 2625-2651 bp | cattttgaagaaattaaacacagaact | 150 |
| NM_005378 MYCN59-6R | LE | 2652-2679 bp | tgctataagatgcagcactaaatatata | 151 |
| NM_005378 MYCN60-6R | LE | 2680-2706 bp | ttttcataaacatgaggtatttcaaag | 152 |

TABLE 5

| | | | MALAT Probes | |
|---|---|---|---|---|
| ACCESSION NAME | FUNCTION | PROBE REGION | SEQUENCE | SEQ ID NO |
| NR_002819 MALAT11-4R | LE | 4056-4078 bp | caggctggttatgactcagaaga | 153 |
| NR_002819 MALAT12-4R | LE | 4079-4100 bp | tgcatctaggccatcatactgc | 154 |
| NR_002819 MALAT13-4R | LE | 4101-4123 bp | attcaccaaggagctgttttctc | 155 |
| NR_002819 MALAT14-4R | LE | 4124-4151 bp | atataatcttttctgcctttacttatca | 156 |
| NR_002819 MALAT15-4R | LE | 4152-4174 bp | ttattecccaatggaggtatgac | 157 |
| NR_002819 MALAT16-4R | LE | 4175-4200 bp | cagtagtaagaatctcagggttatgc | 158 |
| NR_002819 MALAT17-4R | LE | 4201-4225 bp | tggcatatgcagataatgttctcat | 159 |
| NR_002819 MALAT18-4R | LE | 4226-4250 bp | tagctttcatttgcttaaaattttt | 160 |
| NR_002819 MALAT19-4R | LE | 4251-4275 bp | ggtagattccgtaactttaaattgg | 161 |
| NR_002819 MALAT110-4R | LE | 4276-4301 bp | gcttgacaagcaattaactttaaaat | 162 |
| NR_002819 MALAT111-4R | LE | 4302-4328 bp | catcaattcattattttttgtggttata | 163 |
| NR_002819 MALAT112-4R | LE | 4329-4353 bp | gacattgcctcttcattgtatttct | 164 |
| NR_002819 MALAT113-4R | LE | 4354-4379 bp | ttttgtaaaagcagtattttgagatg | 165 |
| NR_002819 MALAT114-4R | LE | 4380-4403 bp | catttcttttcgcttttattctgc | 166 |
| NR_002819 MALAT115-4R | LE | 4404-4430 bp | tccaggattaatgtagtgtaacatttt | 167 |
| NR_002819 MALAT116-4R | LE | 4431-4455 bp | tctcatttatttcggcttcttttat | 168 |
| NR_002819 MALAT117-4R | LE | 4456-4478 bp | aatccacttgatcccaactcatc | 169 |
| NR_002819 MALAT118-4R | LE | 4479-4498 bp | gcacacagcacagcctcctc | 170 |
| NR_002819 MALAT119-4R | BL | 4499-4520 bp | gtctgaggcaaacgaaacattg | 171 |

TABLE 5-continued

MALAT Probes

| ACCESSION NAME | FUNCTION | PROBE REGION | SEQUENCE | SEQ ID NO |
|---|---|---|---|---|
| NR_002819 MALAT120-4R | LE | 4521-4547 bp | aactcttctgataacgaagagatacct | 172 |
| NR_002819 MALAT121-4R | LE | 4548-4568 bp | tgctcccagatgaaatgaagc | 173 |
| NR_002819 MALAT122-4R | BL | 4569-4590 bp | ttaacagctgcctgctgttttc | 174 |
| NR_002819 MALAT123-4R | BL | 4591-4615 bp | tgcagatgcaagttaaacttatctg | 175 |
| NR_002819 MALAT124-4R | LE | 4616-4640 bp | agcacttatccctaacatgcaatac | 176 |
| NR_002819 MALAT125-4R | LE | 4641-4667 bp | ttaagaactccacagctcttaaaaata | 177 |
| NR_002819 MALAT126-4R | BL | 4668-4690 bp | ggagaaagtgccatggttgatat | 178 |
| NR_002819 MALAT127-4R | BL | 4691-4709 bp | tcccctagggaaggggtca | 179 |
| NR_002819 MALAT128-4R | LE | 4710-4733 bp | tggaaaaatttctcaatcctgaaa | 180 |
| NR_002819 MALAT129-4R | LE | 4734-4756 bp | cctacaattttaaaaaggctcga | 181 |
| NR_002819 MALAT130-4R | LE | 4757-4777 bp | ctgaagcccacaggaacaagt | 182 |
| NR_002819 MALAT131-4R | LE | 4778-4803 bp | tctgagtgaagtgtactatcccatca | 183 |
| NR_002819 MALAT132-4R | LE | 4804-4828 bp | gaaattatttaaagatgcaaatgcc | 184 |
| NR_002819 MALAT133-4R | LE | 4829-4854 bp | gcactgatcactttagaggcttttaa | 185 |
| NR_002819 MALAT134-4R | LE | 4855-4878 bp | caaatttccttagttggcatcaag | 186 |
| NR_002819 MALAT135-4R | LE | 4879-4901 bp | gccttcagagattcaatgctaaa | 187 |
| NR_002819 MALAT136-4R | LE | 4902-4926 bp | cacatcatgctattcctttcataga | 188 |
| NR_002819 MALAT137-4R | LE | 4927-4954 bp | ttttagcagtaacatctgattctaacag | 189 |
| NR_002819 MALAT138-4R | LE | 4955-4982 bp | ctacacaatttacatcacaacatgtaaa | 190 |
| NR_002819 MALAT139-4R | LE | 4983-5010 bp | ttattattttgaatgatttaatggtttt | 191 |
| NR_002819 MALAT140-4R | BL | 5011-5043 bp | ttctaaaagtatacattctctaataaaaatagt | 192 |
| NR_002819 MALAT141-4R | LE | 5044-5072 bp | cactattttatttaaataaggagacagct | 193 |
| NR_002819 MALAT142-4R | LE | 5073-5096 bp | ccccaacactgaactacagacaaa | 194 |
| NR_002819 MALAT143-4R | BL | 5097-5116 bp | aagaatccccccccaagattg | 195 |
| NR_002819 MALAT144-4R | LE | 5117-5143 bp | gcagacaaagtttctgaaagattagag | 196 |
| NR_002819 MALAT145-4R | LE | 5144-5168 bp | tgatctggtccattaaagagtgttc | 197 |
| NR_002819 MALAT146-4R | LE | 5169-5188 bp | tcgttcttccgctcaaatcc | 198 |
| NR_002819 MALAT147-4R | LE | 5189-5213 bp | tgtctttcctgccttaaagttacat | 199 |

TABLE 6

17-lncRNAs Associated with Prognostic Signature in MB

| Gene Name | Penalized Coefficient |
|---|---|
| lnc-TMEM258-3 | −0.47771 |
| ZNRF3-AS1 | −0.24098 |
| lnc-TMEM121-3 | −0.17041 |
| MAP3K14-AS1 | −0.07358 |
| LINC01152 | −0.0675 |
| KLF3-AS1 | −0.05371 |
| lnc-PRR34-l | −0.0379 |
| lnc-FOXD4L5-25 | −0.03664 |
| AC209154.1 | −0.01405 |

TABLE 6-continued 17-lncRNAs Associated with Prognostic Signature in MB

| Gene Name | Penalized Coefficient |
|---|---|
| TTC28-AS1 | −0.00891 |
| FAM222A-AS1 | 0.07403 |
| LINC00336 | 0.042296 |
| LINC01551 | 0.073539 |
| H19 | 0.102589 |
| lnc-RRM2-3 | 0.107783 |
| lnc-CDYL-1 | 0.198379 |
| AL139393.2 | 0.231787 |

17-lncRNAs identified from penalized COX regression analysis of Cavalli17 dataset. Negative coefficient values highlights good prognosis marker candidates and positive coefficient value highlights bad prognosis marker candidates.

TABLE 7

List of MB Cases with Clinical Features Analyzed in RNA-FISH

| Tissue Diagnosis ID | Subgroup | Historogy | Age | Sex | Overall Survival to Last Visit |
|---|---|---|---|---|---|
| 18828 | SHH | Nodular MB | 9 | M | 16 |
| 18830 | Group 4 | Classic MB | 12 | M | 37 |
| 18831 | SHH | Nodular MB | 3 | M | 72 |
| 18834 | SHH | Nodular MB | 20 | M | 200 |
| 18837 | SHH | Nodular MB | 6 | M | 25 |
| 18838 | SHH | Nodular MB | 2 | F | 215 |
| 18840 | SHH | Nodular MB | 12 | F | 34 |
| 18841 | Group 4 | Nod MB with Anap | 2 | M | 21 |
| 18842 | Unknown | MB | 11 | F | 101 |
| 18843 | Group 3 | Mod A | 12 | F | Unknown |
| 18844 | Unknown | Classic MB | 5 | F | 8 |
| 18845 | Unknown | Classic MB | 16 | F | 58 |
| 18846 | SHH | Sev A | | M | 28 |
| 18847 | SHH | Nodular MB | 1 | M | Unknown |
| 18850 | Unknown | PNET/Pineoblastoma | 21 | F | 46 |
| 18851 | Group 3 | LC MB | 9 | M | 9 |
| 18852 | SHH | Classic MB | 22 | M | Unknown |
| 18853 | Unknown | AT/RT | 8 | M | 1M |
| 18854 | Unknown | AT/RT | 8M | F | 4 |
| 18855 | Unknown | AT/RT | 11M | M | 1M |
| 18856 | SHH | Nodular MB | 11 | M | 109 |
| 18857 | Unknown | Medulloblastoma | 11 | F | Unknown |
| 18858 | Unknown | PNET | 3 | F | 1M |
| 18859 | Group 4 | MB | 2 | F | 27 |
| 18860 | Unknown | Anaplastic MB | 8 | F | 27 |
| 18861 | SHH | Classic MB | 8 | F | 123 |
| 18862 | Group 4 | MB | 10 | Unknown | Unknown |
| 18863 | Group 4 | MB | 5 | M | 198 |
| 18864 | SHH | Desmoplastic MB | 7 | M | 119 |
| 18865 | Group 4 | F Mod A | 10 | M | 119 |
| 18866 | Group 4 | Classic MB | 9 | M | 103 |
| 18867 | Unknown | Mod A | 18 | M | 84 |
| 18868 | Group 4 | Classic MB | 15 | M | 118 |
| 18869 | Group 4 | MB | 13 | F | 69 |
| 18870 | Group 3 | LC MB | 5 | M | 10 |
| 18871 | Group 4 | Classic MB | 13 | F | 121 |
| 18872 | SHH | Nodular MB | 11M | M | 39 |
| 18873 | SHH | Nodular MB | 38 | F | 207 |
| 18874 | Unknown | Mod A | 9 | M | 170 |
| 18875 | Unknown | Medulloepithelioma | 1 | F | 1 |
| 18876 | Unknown | Medulloepithelioma | 1 | F | 19M |
| 18877 | SHH | MB | 15 | F | 63 |
| 18878 | unknown | Classic MB | 6 | F | 18 |
| 18879 | SHH | Classic MB | 38 | M | 32M |
| 18880 | Group 4 | F Mod A | 5 | F | 35 |
| 18881 | SHH | Classic MB | 6 | M | 127 |
| 18882 | Group 3 | Classic MB | 1 | M | 1M |
| 18883 | SHH | MB with desmoplasia | 16 | F | 167 |
| 18884 | SHH | Sev A with Nodules | | M | 12 |
| 18885 | SHH | Classic MB | 3 | M | 100 |
| 18886 | Group 4 | Sev A | 6 | F | 147 |
| 18887 | Group 4 | Sev A | | M | 96 |
| 18888 | Group 3 | Sev A | 18 | M | 12 |
| 18890 | SHH | LC MB | 2 | M | 47 |
| 18891 | Group 4 | F Mod A | 6 | F | 37 |
| 18892 | Group 3 | Sev A | 12 | M | 23 |
| 18893 | SHH | Classic MB | 38 | M | 12 |
| 18894 | SHH | F Mod A | 16 | M | 20 |
| 18895 | SHH | Mod A | | F | 12 |
| 18896 | Unknown | F Mod A | 9 | F | 101 |
| 18897 | Group 3 | F Mod A | 10 | M | Unknown |
| 18898 | SHH | Nodular MB | 29 | F | 28 |
| 18899 | Unknown | Classic MB | 12 | F | 183 |
| 18900 | Unknown | PNET | 10 | F | 55 |
| 18901 | SHH | Mod A | 31 | F | 10 |

TABLE 7-continued

List of MB Cases with Clinical Features Analyzed in RNA-FISH

| Tissue Diagnosis ID | Subgroup | Historogy | Age | Sex | Overall Survival to Last Visit |
|---|---|---|---|---|---|
| 18902 | Group 3 | Unknown | 4 | M | 12 |
| 18903 | Unknown | PNET | 35 | M | 20 |
| 18904 | unknown | MB met to mandible | 9 | M | 19 |
| 18905 | WNT | Mod A | 9 | F | 187 |
| 18906 | SHH | Classic MB | 2 | F | 120 |
| 18907 | Group 4 | Classic MB | 8 | F | 31 |
| 56510 | Unknown | MB | 11 | F | 101 |
| 61379 | Group 3 | Sev A | 11 | M | 27 |
| 61380 | Group 4 | Mod A | 32 | F | 60 |
| 61382 | SHH | Unknown | 55 | F | 9 |
| 61383 | SHH | Nodular MB/MBEN | 1 | M | Unknown |
| 61384 | Unknown | MB | 16 | M | 147 |
| 61386 | Group 4 | Nodular MB | 28 | M | 25 |
| 61387 | Unknown | Medulloepithelioma | 5 | M | 22 |
| 61403 | Unknown | PNET | 1 | M | 34 |

TABLE 8

Primer sequences for qRT-PCR

| Target gene | Primer sequence (5' to 3') | | SEQ ID NO. |
|---|---|---|---|
| ACTB | Forward: | cctggcattgccgacaggatg | 204 |
| | Reverse: | ccgatccacacggagtacttgcg | 205 |
| lnc-HLX-2-7 | Forward: | gcttctctggcacatggact | 206 |
| | Reverse: | gtccttcgtgagcacagcat | 207 |
| HLX | Forward: | gcttctctggcacatggact | 208 |
| | Reverse: | gtccttcgtgagcacagcat | 209 |
| MYC | Forward: | aaaggcccccaaggtagtta | 210 |
| | Reverse: | gcacaagagttccgtagctg | 211 |
| MYCN | Forward: | ctaatactggccgcaaaagc | 212 |
| | Reverse: | cataaggggtttgccatttg | 213 |
| PTGR1 | Forward: | cagacacaataccactgtctttgg | 214 |
| | Reverse: | ctgcattaaccatcactgtttctc | 215 |
| FZD6 | Forward: | agactctctggggaacaggtc | 216 |
| | Reverse: | ggccagtgtcagtaatatcactctt | 217 |
| TRPM3 | Forward: | aatacttcagagaaaaggatgatcg | 218 |
| | Reverse: | gagtgctctctctcgttgacttc | 219 |
| NAMPT | Forward: | aaaagggccgattatctttacatag | 220 |
| | Reverse: | ccattcttgaagacagtatggagaa | 221 |
| NRBP2 | Forward: | aggacgagagcgacatcct | 222 |
| | Reverse: | ggctaggaaggtgctctgaag | 223 |
| NBAT1 | Forward: | gtttatccatcttcagctccactct | 224 |
| | Reverse: | tctgtgggtttcagtttcttcat | 225 |
| CCNG2 | Forward: | caacagctactatagtgttcctgagc | 226 |
| | Reverse: | tctcctctccacaactcatatcttc | 227 |
| ELK4 | Forward: | gcaagaacaagcctaacatgaatta | 228 |
| | Reverse: | acacaaacttctgaccattcacttt | 229 |
| CDKN2C | Forward: | ttgcaaaataatgtaaacgtcaatg | 230 |
| | Reverse: | ttagcacctctaagtagcagtctcc | 231 |
| CDK6 | Forward: | caaccaattgagaagtttgtaacag | 232 |
| | Reverse: | ggcactgtaggcagatattctttt | 233 |

TABLE 9

Primer sequences for ChIP-qPCR

| Target gene | Primer sequence (5' to 3') | SEQ ID NO. |
|---|---|---|
| HLX-2KB | Forward: ttatttcttaagagagagggtgagg | 234 |
| | Reverse: aatttgactgcaaacatttagacct | 235 |
| HLX-TSS | Forward: tacgcagagtagcaagaagcact | 236 |
| | Reverse: tggaggggaattaggaacaag | 237 |
| E-box | Forward: taataaacaaaaccgcctagatgag | 238 |
| | Reverse: aaaggctttacataaatcggcttac | 239 |

TABLE 10

Top 50 Differentially Upregulated lncRNAs in Group 3 MB

| Gene.ID | Fold Change (log2) | p-value |
|---|---|---|
| lnc-STAP1-13 | 12.3151 | 1.0645E−04 |
| lnc-SLITRK1-1 | 12.2487 | 9.3581E−09 |
| lnc-MYO3A-l | 11.7062 | 6.4649E−06 |
| lnc-AXIN1-1 | 10.4428 | 6.0770E−05 |
| lnc-POU5F1B-5 | 10.3653 | 1.0766E−16 |
| LINC02342 | 9.9339 | 1.7037E−09 |
| lnc-PDGFA-17 | 9.8875 | 6.7468E−08 |
| lnc-SERPINB3-3 | 9.7623 | 6.1748E−17 |
| lnc-STAP1-2 | 9.6277 | 6.6276E−12 |
| LINC01467 | 9.3207 | 2.0908E−20 |
| lnc-IGLL1-4 | 9.2966 | 3.1889E−05 |
| lnc-HLX-1 | 8.7256 | 7.1143E−22 |
| lnc-SYT1-2 | 8.6991 | 5.2255E−10 |
| lnc-SYK-13 | 8.4236 | 3.7254E−06 |
| lnc-HLX-5 | 7.8451 | 1.2979E−14 |
| lnc-NFATC1-1 | 7.6858 | 7.9406E−06 |
| lnc-APBA2-9 | 7.6460 | 6.4510E−09 |

TABLE 10-continued

Top 50 Differentially Upregulated lncRNAs in Group 3 MB

| Gene.ID | Fold Change (log2) | p-value |
|---|---|---|
| lnc-MAGEA12-3 | 7.5857 | 6.3922E−10 |
| LINC02378 | 7.2464 | 2.8975E−06 |
| lnc-PRSS1-1 | 7.0733 | 4.6988E−13 |
| lnc-MGST1-7 | 6.8156 | 8.2139E−12 |
| ESRG | 6.7417 | 1.5129E−36 |
| lnc-KIAA1210-1 | 6.5451 | 2.5660E−06 |
| lnc-PRSS1-7 | 6.5187 | 7.3174E−13 |
| lnc-VCX-6 | 6.4619 | 1.2289E−06 |
| lnc-ANXA1-3 | 6.4276 | 1.3172E−11 |
| lnc-BARD1-1 | 6.4074 | 1.5158E−08 |
| lnc-CSAG3-l | 6.3320 | 2.2890E−10 |
| lnc-EHF-1 | 6.2428 | 1.4561E−06 |
| lnc-UTP23-12 | 6.2302 | 6.4442E−09 |
| lnc-WRN-6 | 6.1788 | 1.9794E−07 |
| lnc-WRN-5 | 6.1445 | 6.4673E−06 |
| lnc-MYO3A-2 | 6.1383 | 3.6319E−06 |
| lnc-DDX60L-3 | 6.0955 | 2.0418E−07 |
| lnc-HLX-6 | 6.0672 | 1.3604E−23 |
| LINC01501 | 6.0319 | 1.8883E−16 |
| lnc-HLX-2 | 5.9981 | 7.5051E−11 |
| lnc-FRG2C-5 | 5.9857 | 7.8191E−04 |
| lnc-ALX1-2 | 5.9346 | 2.2683E−44 |
| lnc-PLXNA2-3 | 5.9338 | 3.8248E−04 |
| LINC02466 | 5.9253 | 4.1574E−06 |
| lnc-RAB17-1 | 5.8827 | 4.4016E−12 |
| lnc-PLA2G4A-5 | 5.8815 | 3.0865E−04 |
| lnc-CCT8L2-1 | 5.8456 | 1.3576E−04 |
| LINC01323 | 5.8226 | 2.5514E−06 |
| lnc-BMP2-2 | 5.7603 | 8.9155E−06 |
| lnc-WRN-3 | 5.7561 | 2.3437E−09 |
| lnc-RMDN1-2 | 5.6879 | 2.9128E−05 |
| lnc-SLC22A16-2 | 5.6778 | 1.7633E−32 |
| LINC01324 | 5.6254 | 7.7208E−12 |

We claim:

1. A method comprising detecting long non-coding (lnc) RNA HLX2-7 in a biological sample obtained from a patient having or suspected of having medulloblastoma, wherein the detecting step is performed using RNA fluorescence in situ hybridization (FISH) assay.

2. The method of claim 1, wherein the biological sample is a tissue sample.

3. The method of claim 2, wherein the tissue sample is a formalin-fixed paraffin-embedded (FFPE) sample.

4. The method of claim 1, wherein the FISH assay comprises oligonucleotide probes that hybridize to lncHLX2-7 and branched DNA signal amplification.

5. The method of claim 4, wherein the probes comprise at least one of SEQ ID NOS: 3-4 and 8-21.

6. The method of claim 4, wherein the probes comprise SEQ ID NOS: 2-3 and 8-21.

7. The method of claim 5, wherein the probes further comprise at least one of SEQ ID NOS: 5-7.

8. The method of claim 6, wherein the probes further comprise SEQ ID NOS: 5-7.

9. The method of claim 1, further comprising detecting MYC expression in the biological sample.

10. The method of claim 9, wherein the biological sample is a tissue sample.

11. The method of claim 10, wherein the tissue sample is a formalin-fixed paraffin-embedded (FFPE) sample.

12. The method of claim 9, wherein the FISH assay comprises oligonucleotide probes that hybridize to MYC and branched DNA signal amplification.

13. The method of claim 12, wherein the probes comprise at least one of SEQ ID NOS: 51-56, 59-60, 62-63, 66-69, 72-73, 75-78, 81-98, 101-102.

14. The method of claim 13, wherein the probes comprise SEQ ID NOS: 51-56, 59-60, 62-63, 66-69, 72-73, 75-78, 81-98, 101-102.

15. The method of claim 13, wherein the probes further comprise at least one of SEQ ID NOS: 57-58, 61, 64-65, 70-71, 74, 79-80, 99-100.

16. The method of claim 14, wherein the probes further comprise SEQ ID NOS: 57-58, 61, 64-65, 70-71, 74, 79-80, 99-100.

17. The method of claim 9, further comprising detecting lnc RNA SPRY4-IT1 in the biological sample.

18. The method of claim 17, wherein the biological sample is a tissue sample.

19. The method of claim 18, wherein the tissue sample is a formalin-fixed paraffin-embedded (FFPE) sample.

20. The method of claim 17, wherein the FISH assay comprises oligonucleotide probes that hybridize to lnc SPRY4-IT1 and branched DNA signal amplification.

21. The method of claim 20, wherein the probes comprise at least one of SEQ ID NOS: 22-25 and 27-50.

22. The method of claim 21, wherein the probes comprise SEQ ID NOS: 22-25 and 27-50.

23. The method of claim 21, wherein the probes further comprise SEQ ID NO: 26.

24. The method claim 17, further comprising detecting MYCN in the biological sample.

25. The method of claim 24, wherein the biological sample is a tissue sample.

26. The method of claim 25, wherein the tissue sample is a formalin-fixed paraffin-embedded (FFPE) sample.

27. The method of claim 24, wherein the FISH assay comprises oligonucleotide probes that hybridize to MYCN and branched DNA signal amplification.

28. The method of claim 27, wherein the probes comprise at least one of SEQ ID NOS: 103-104, 107-108, 111-112, 114-125, 127-130, 133-144, 147-152.

29. The method of claim 27, wherein the probes comprise SEQ ID NOS: 103-104, 107-108, 111-112, 114-125, 127-130, 133-144, 147-152.

30. The method of claim 28, wherein the probes further comprise at least one of SEQ ID NOS: 105-106, 109-110, 113, 126, 131-132, 145-146.

31. The method of claim 29, wherein the probes further comprise SEQ ID NOS: 105-106, 109-110, 113, 126, 131-132, 145-146.

32. The method of claim 17, further comprising detecting one or more lnc RNAs selected from the group consisting of MIR100HG, USP2-AS1, lnc-CFAP100-4, ARHGEF7-AS2, lnc-HLX-1, lnc-EXPH5-2, lnc-CH25H-2, and lnc-TDRP-3.

* * * * *

SEQUENCE LISTING

<160> NUMBER OF SEQ ID NOS: 241

<210> SEQ ID NO 1
<211> LENGTH: 20
<212> TYPE: RNA
<213> ORGANISM: Artificial Sequence
<220> FEATURE:
<223> OTHER INFORMATION: 5' gRNA encompassing the HLX2-7 region

<400> SEQUENCE: 1
ggacccacuc uccaacgcag                                                    20

<210> SEQ ID NO 2
<211> LENGTH: 20
<212> TYPE: RNA
<213> ORGANISM: Artificial Sequence
<220> FEATURE:
<223> OTHER INFORMATION: 3' gRNA encompassing the HLX2-7 region

<400> SEQUENCE: 2
gcagggaccc cucauugacg                                                    20

<210> SEQ ID NO 3
<211> LENGTH: 21
<212> TYPE: DNA
<213> ORGANISM: Artificial Sequence -continued

```
<220> FEATURE:
<223> OTHER INFORMATION: lnc_HLX2_71-1R

<400> SEQUENCE: 3
ccagacataa actcgccaag c                                               21

<210> SEQ ID NO 4
<211> LENGTH: 18
<212> TYPE: DNA
<213> ORGANISM: Artificial Sequence
<220> FEATURE:
<223> OTHER INFORMATION: lnc_HLX2_72-1R

<400> SEQUENCE: 4
ccgcatgtgt ccaggcac                                                   18

<210> SEQ ID NO 5
<211> LENGTH: 26
<212> TYPE: DNA
<213> ORGANISM: Artificial Sequence
<220> FEATURE:
<223> OTHER INFORMATION: lnc_HLX2_73-1R

<400> SEQUENCE: 5
gtgtgtgtgt gtgtgtgtgt ttattc                                         26

<210> SEQ ID NO 6
<211> LENGTH: 25
<212> TYPE: DNA
<213> ORGANISM: Artificial Sequence
<220> FEATURE:
<223> OTHER INFORMATION: lnc_HLX2_74-1R

<400> SEQUENCE: 6
gcagtaacat cgaatgtgtg tgtgt                                          25

<210> SEQ ID NO 7
<211> LENGTH: 24
<212> TYPE: DNA
<213> ORGANISM: Artificial Sequence
<220> FEATURE:
<223> OTHER INFORMATION: lnc_HLX2_75-1R

<400> SEQUENCE: 7
aaaaaaatga atggatgaag gaat                                           24

<210> SEQ ID NO 8
<211> LENGTH: 23
<212> TYPE: DNA
<213> ORGANISM: Artificial Sequence
<220> FEATURE:
<223> OTHER INFORMATION: lnc_HLX2_76-1R

<400> SEQUENCE: 8
ggatccccat aaatactgca atg                                            23

<210> SEQ ID NO 9
<211> LENGTH: 24
<212> TYPE: DNA
<213> ORGANISM: Artificial Sequence
<220> FEATURE:
<223> OTHER INFORMATION: lnc_HLX2_77-1R

<400> SEQUENCE: 9
tctctatggt gcaaacactc acaa                                           24
```

-continued

```
<210> SEQ ID NO 10
<211> LENGTH: 27
<212> TYPE: DNA
<213> ORGANISM: Artificial Sequence
<220> FEATURE:
<223> OTHER INFORMATION: lnc_HLX2_78-1R

<400> SEQUENCE: 10
tggttaatgc ttagtcaaat acttttt                                            27

<210> SEQ ID NO 11
<211> LENGTH: 25
<212> TYPE: DNA
<213> ORGANISM: Artificial Sequence
<220> FEATURE:
<223> OTHER INFORMATION: lnc_HLX2_79-1R

<400> SEQUENCE: 11
acaaacactg atctcttagc tggaa                                              25

<210> SEQ ID NO 12
<211> LENGTH: 24
<212> TYPE: DNA
<213> ORGANISM: Artificial Sequence
<220> FEATURE:
<223> OTHER INFORMATION: lnc_HLX2_710-1R

<400> SEQUENCE: 12
caaccacctc agctattttg aatg                                               24

<210> SEQ ID NO 13
<211> LENGTH: 22
<212> TYPE: DNA
<213> ORGANISM: Artificial Sequence
<220> FEATURE:
<223> OTHER INFORMATION: lnc_HLX2_711-1R

<400> SEQUENCE: 13
gggaatactg gctgtcctct cc                                                 22

<210> SEQ ID NO 14
<211> LENGTH: 26
<212> TYPE: DNA
<213> ORGANISM: Artificial Sequence
<220> FEATURE:
<223> OTHER INFORMATION: lnc_HLX2_712-1R

<400> SEQUENCE: 14
cctaggaaac taataaacct cttttg                                             26

<210> SEQ ID NO 15
<211> LENGTH: 24
<212> TYPE: DNA
<213> ORGANISM: Artificial Sequence
<220> FEATURE:
<223> OTHER INFORMATION: lnc_HLX2_713-1R

<400> SEQUENCE: 15
gtctgtgtca atttgtgaca gcag                                               24

<210> SEQ ID NO 16
<211> LENGTH: 28
<212> TYPE: DNA
<213> ORGANISM: Artificial Sequence
<220> FEATURE:
<223> OTHER INFORMATION: lnc_HLX2_714-1R
```

<400> SEQUENCE: 16
acacatttct gttgttttaa gtcactaa                                                    28

<210> SEQ ID NO 17
<211> LENGTH: 26
<212> TYPE: DNA
<213> ORGANISM: Artificial Sequence
<220> FEATURE:
<223> OTHER INFORMATION: lnc_HLX2_715-1R

<400> SEQUENCE: 17
gagaagcaga gaatgtagtg acacaa                                                      26

<210> SEQ ID NO 18
<211> LENGTH: 22
<212> TYPE: DNA
<213> ORGANISM: Artificial Sequence
<220> FEATURE:
<223> OTHER INFORMATION: lnc_HLX2_716-1R

<400> SEQUENCE: 18
cagaagaaga gtccatgtgc ca                                                          22

<210> SEQ ID NO 19
<211> LENGTH: 23
<212> TYPE: DNA
<213> ORGANISM: Artificial Sequence
<220> FEATURE:
<223> OTHER INFORMATION: lnc_HLX2_717-1R

<400> SEQUENCE: 19
ggaagacaga ggaaaactgg atg                                                         23

<210> SEQ ID NO 20
<211> LENGTH: 22
<212> TYPE: DNA
<213> ORGANISM: Artificial Sequence
<220> FEATURE:
<223> OTHER INFORMATION: lnc_HLX2_718-1R

<400> SEQUENCE: 20
taccacacgc atgcttatga ga                                                          22

<210> SEQ ID NO 21
<211> LENGTH: 20
<212> TYPE: DNA
<213> ORGANISM: Artificial Sequence
<220> FEATURE:
<223> OTHER INFORMATION: lnc_HLX2_719-1R

<400> SEQUENCE: 21
cctgggtgga cgctaaatgc                                                             20

<210> SEQ ID NO 22
<211> LENGTH: 22
<212> TYPE: DNA
<213> ORGANISM: Artificial Sequence
<220> FEATURE:
<223> OTHER INFORMATION: SPRY4-IT11-4R

<400> SEQUENCE: 22
ggcagatcac ttgaggtcag ga                                                          22

<210> SEQ ID NO 23

```
<211> LENGTH: 20
<212> TYPE: DNA
<213> ORGANISM: Artificial Sequence
<220> FEATURE:
<223> OTHER INFORMATION: SPRY4-IT12-4R

<400> SEQUENCE: 23
ccttttggga ggccaaggta                                          20

<210> SEQ ID NO 24
<211> LENGTH: 22
<212> TYPE: DNA
<213> ORGANISM: Artificial Sequence
<220> FEATURE:
<223> OTHER INFORMATION: SPRY4-IT13-4R

<400> SEQUENCE: 24
tggctcatgc ctgtaatctc ag                                       22

<210> SEQ ID NO 25
<211> LENGTH: 18
<212> TYPE: DNA
<213> ORGANISM: Artificial Sequence
<220> FEATURE:
<223> OTHER INFORMATION: SPRY4-IT14-4R

<400> SEQUENCE: 25
aaagaaggcc tggcgcag                                            18

<210> SEQ ID NO 26
<211> LENGTH: 27
<212> TYPE: DNA
<213> ORGANISM: Artificial Sequence
<220> FEATURE:
<223> OTHER INFORMATION: SPRY4-IT15-4R

<400> SEQUENCE: 26
aaaaaaaaag aaagaaaaaa agaaaag                                  27

<210> SEQ ID NO 27
<211> LENGTH: 24
<212> TYPE: DNA
<213> ORGANISM: Artificial Sequence
<220> FEATURE:
<223> OTHER INFORMATION: SPRY4-IT16-4R

<400> SEQUENCE: 27
cagcacagct aaatgatgtc tcaa                                     24

<210> SEQ ID NO 28
<211> LENGTH: 22
<212> TYPE: DNA
<213> ORGANISM: Artificial Sequence
<220> FEATURE:
<223> OTHER INFORMATION: SPRY4-IT17-4R

<400> SEQUENCE: 28
agctgcctat ttaagaaccc ct                                       22

<210> SEQ ID NO 29
<211> LENGTH: 25
<212> TYPE: DNA
<213> ORGANISM: Artificial Sequence
<220> FEATURE:
<223> OTHER INFORMATION: SPRY4-IT18-4R

<400> SEQUENCE: 29
```
gctgacaaag gaaaacaatt ttctg                                             25

<210> SEQ ID NO 30
<211> LENGTH: 24
<212> TYPE: DNA
<213> ORGANISM: Artificial Sequence
<220> FEATURE:
<223> OTHER INFORMATION: SPRY4-IT19-4R

<400> SEQUENCE: 30
aagagcctct gctgaattta tgtg                                              24

<210> SEQ ID NO 31
<211> LENGTH: 18
<212> TYPE: DNA
<213> ORGANISM: Artificial Sequence
<220> FEATURE:
<223> OTHER INFORMATION: SPRY4-IT110-4R

<400> SEQUENCE: 31
caccagcagg gaccctcc                                                     18

<210> SEQ ID NO 32
<211> LENGTH: 18
<212> TYPE: DNA
<213> ORGANISM: Artificial Sequence
<220> FEATURE:
<223> OTHER INFORMATION: SPRY4-IT111-4R

<400> SEQUENCE: 32
actgctggcc tcacccct                                                     18

<210> SEQ ID NO 33
<211> LENGTH: 23
<212> TYPE: DNA
<213> ORGANISM: Artificial Sequence
<220> FEATURE:
<223> OTHER INFORMATION: SPRY4-IT112-4R

<400> SEQUENCE: 33
agcaaaaacc aaatcagagt tcc                                               23

<210> SEQ ID NO 34
<211> LENGTH: 22
<212> TYPE: DNA
<213> ORGANISM: Artificial Sequence
<220> FEATURE:
<223> OTHER INFORMATION: SPRY4-IT113-4R

<400> SEQUENCE: 34
gattcctttc aaccaccagc tc                                                22

<210> SEQ ID NO 35
<211> LENGTH: 25
<212> TYPE: DNA
<213> ORGANISM: Artificial Sequence
<220> FEATURE:
<223> OTHER INFORMATION: SPRY4-IT114-4R

<400> SEQUENCE: 35
ccctattata accccgatgt agtag                                             25

<210> SEQ ID NO 36
<211> LENGTH: 26
<212> TYPE: DNA

<213> ORGANISM: Artificial Sequence
<220> FEATURE:
<223> OTHER INFORMATION: SPRY4-IT115-4R

<400> SEQUENCE: 36
actgggcata ttctaaaatg tatctt                                    26

<210> SEQ ID NO 37
<211> LENGTH: 18
<212> TYPE: DNA
<213> ORGANISM: Artificial Sequence
<220> FEATURE:
<223> OTHER INFORMATION: SPRY4-IT116-4R

<400> SEQUENCE: 37
gcagcatccg atggctcc                                             18

<210> SEQ ID NO 38
<211> LENGTH: 19
<212> TYPE: DNA
<213> ORGANISM: Artificial Sequence
<220> FEATURE:
<223> OTHER INFORMATION: SPRY4-IT117-4R

<400> SEQUENCE: 38
ttggctctct ggggacgat                                            19

<210> SEQ ID NO 39
<211> LENGTH: 19
<212> TYPE: DNA
<213> ORGANISM: Artificial Sequence
<220> FEATURE:
<223> OTHER INFORMATION: SPRY4-IT118-4R

<400> SEQUENCE: 39
gagcttggcc cacgatgac                                            19

<210> SEQ ID NO 40
<211> LENGTH: 18
<212> TYPE: DNA
<213> ORGANISM: Artificial Sequence
<220> FEATURE:
<223> OTHER INFORMATION: SPRY4-IT119-4R

<400> SEQUENCE: 40
ggccagacat ggggatgg                                             18

<210> SEQ ID NO 41
<211> LENGTH: 19
<212> TYPE: DNA
<213> ORGANISM: Artificial Sequence
<220> FEATURE:
<223> OTHER INFORMATION: SPRY4-IT120-4R

<400> SEQUENCE: 41
catctgggcc tgcagttga                                            19

<210> SEQ ID NO 42
<211> LENGTH: 20
<212> TYPE: DNA
<213> ORGANISM: Artificial Sequence
<220> FEATURE:
<223> OTHER INFORMATION: SPRY4-IT121-4R

<400> SEQUENCE: 42
cctccagagg cagctgtcaa                                           20

```
<210> SEQ ID NO 43
<211> LENGTH: 21
<212> TYPE: DNA
<213> ORGANISM: Artificial Sequence
<220> FEATURE:
<223> OTHER INFORMATION: SPRY4-IT122-4R

<400> SEQUENCE: 43
gcattcacag gctcccataa c                                              21

<210> SEQ ID NO 44
<211> LENGTH: 19
<212> TYPE: DNA
<213> ORGANISM: Artificial Sequence
<220> FEATURE:
<223> OTHER INFORMATION: SPRY4-IT123-4R

<400> SEQUENCE: 44
gcaggcaatg gggatgttg                                                 19

<210> SEQ ID NO 45
<211> LENGTH: 17
<212> TYPE: DNA
<213> ORGANISM: Artificial Sequence
<220> FEATURE:
<223> OTHER INFORMATION: SPRY4-IT124-4R

<400> SEQUENCE: 45
ggatgggagc agccgct                                                   17

<210> SEQ ID NO 46
<211> LENGTH: 19
<212> TYPE: DNA
<213> ORGANISM: Artificial Sequence
<220> FEATURE:
<223> OTHER INFORMATION: SPRY4-IT125-4R

<400> SEQUENCE: 46
aagtcccacc aggaagcca                                                 19

<210> SEQ ID NO 47
<211> LENGTH: 21
<212> TYPE: DNA
<213> ORGANISM: Artificial Sequence
<220> FEATURE:
<223> OTHER INFORMATION: SPRY4-IT126-4R

<400> SEQUENCE: 47
cagattcccc aattcatgga a                                              21

<210> SEQ ID NO 48
<211> LENGTH: 23
<212> TYPE: DNA
<213> ORGANISM: Artificial Sequence
<220> FEATURE:
<223> OTHER INFORMATION: SPRY4-IT127-4R

<400> SEQUENCE: 48
taataggcct tggaatcaga aag                                            23

<210> SEQ ID NO 49
<211> LENGTH: 21
<212> TYPE: DNA
<213> ORGANISM: Artificial Sequence
<220> FEATURE:
```

<223> OTHER INFORMATION: SPRY4-IT128-4R

<400> SEQUENCE: 49
atgggcaatg ctcagaaatt t                                                         21

<210> SEQ ID NO 50
<211> LENGTH: 26
<212> TYPE: DNA
<213> ORGANISM: Artificial Sequence
<220> FEATURE:
<223> OTHER INFORMATION: SPRY4-IT129-4R

<400> SEQUENCE: 50
catgtcctac agataaagca aaagaa                                                    26

<210> SEQ ID NO 51
<211> LENGTH: 18
<212> TYPE: DNA
<213> ORGANISM: Artificial Sequence
<220> FEATURE:
<223> OTHER INFORMATION: MYC1-6R

<400> SEQUENCE: 51
cgttgagggg catcgtcg                                                             18

<210> SEQ ID NO 52
<211> LENGTH: 24
<212> TYPE: DNA
<213> ORGANISM: Artificial Sequence
<220> FEATURE:
<223> OTHER INFORMATION: MYC2-6R

<400> SEQUENCE: 52
catagttcct gttggtgaag ctaa                                                      24

<210> SEQ ID NO 53
<211> LENGTH: 21
<212> TYPE: DNA
<213> ORGANISM: Artificial Sequence
<220> FEATURE:
<223> OTHER INFORMATION: MYC3-6R

<400> SEQUENCE: 53
gcaccgagtc gtagtcgagg t                                                         21

<210> SEQ ID NO 54
<211> LENGTH: 21
<212> TYPE: DNA
<213> ORGANISM: Artificial Sequence
<220> FEATURE:
<223> OTHER INFORMATION: MYC4-6R

<400> SEQUENCE: 54
cgtcgcagta gaaatacggc t                                                         21

<210> SEQ ID NO 55
<211> LENGTH: 23
<212> TYPE: DNA
<213> ORGANISM: Artificial Sequence
<220> FEATURE:
<223> OTHER INFORMATION: MYC5-6R

<400> SEQUENCE: 55
ctgctggtag aagttctcct cct                                                       23

-continued

```
<210> SEQ ID NO 56
<211> LENGTH: 19
<212> TYPE: DNA
<213> ORGANISM: Artificial Sequence
<220> FEATURE:
<223> OTHER INFORMATION: MYC6-6R

<400> SEQUENCE: 56
gcagctcgct ctgctgctg                                              19

<210> SEQ ID NO 57
<211> LENGTH: 13
<212> TYPE: DNA
<213> ORGANISM: Artificial Sequence
<220> FEATURE:
<223> OTHER INFORMATION: MYC7-6R

<400> SEQUENCE: 57
ggcgccgggg gct                                                    13

<210> SEQ ID NO 58
<211> LENGTH: 22
<212> TYPE: DNA
<213> ORGANISM: Artificial Sequence
<220> FEATURE:
<223> OTHER INFORMATION: MYC8-6R

<400> SEQUENCE: 58
tttcttccag atatcctcgc tg                                          22

<210> SEQ ID NO 59
<211> LENGTH: 18
<212> TYPE: DNA
<213> ORGANISM: Artificial Sequence
<220> FEATURE:
<223> OTHER INFORMATION: MYC9-6R

<400> SEQUENCE: 59
ggtgggcagc agctcgaa                                               18

<210> SEQ ID NO 60
<211> LENGTH: 17
<212> TYPE: DNA
<213> ORGANISM: Artificial Sequence
<220> FEATURE:
<223> OTHER INFORMATION: MYC10-6R

<400> SEQUENCE: 60
ctaggggaca ggggcgg                                                17

<210> SEQ ID NO 61
<211> LENGTH: 13
<212> TYPE: DNA
<213> ORGANISM: Artificial Sequence
<220> FEATURE:
<223> OTHER INFORMATION: MYC11-6R

<400> SEQUENCE: 61
cccggagcgg cgg                                                    13

<210> SEQ ID NO 62
<211> LENGTH: 19
<212> TYPE: DNA
<213> ORGANISM: Artificial Sequence
<220> FEATURE:
<223> OTHER INFORMATION: MYC12-6R
```

-continued

<400> SEQUENCE: 62
cgtaggaggg cgagcagag                                                     19

<210> SEQ ID NO 63
<211> LENGTH: 20
<212> TYPE: DNA
<213> ORGANISM: Artificial Sequence
<220> FEATURE:
<223> OTHER INFORMATION: MYC13-6R

<400> SEQUENCE: 63
ggagaagggt gtgaccgcaa                                                    20

<210> SEQ ID NO 64
<211> LENGTH: 19
<212> TYPE: DNA
<213> ORGANISM: Artificial Sequence
<220> FEATURE:
<223> OTHER INFORMATION: MYC14-6R

<400> SEQUENCE: 64
cgtcgttgtc tccccgaag                                                     19

<210> SEQ ID NO 65
<211> LENGTH: 20
<212> TYPE: DNA
<213> ORGANISM: Artificial Sequence
<220> FEATURE:
<223> OTHER INFORMATION: MYC17-6R

<400> SEQUENCE: 65
agctcggtca ccatctccag                                                    20

<210> SEQ ID NO 66
<211> LENGTH: 20
<212> TYPE: DNA
<213> ORGANISM: Artificial Sequence
<220> FEATURE:
<223> OTHER INFORMATION: MYC18-6R

<400> SEQUENCE: 66
tcaccatgtc tcctcccagc                                                    20

<210> SEQ ID NO 67
<211> LENGTH: 21
<212> TYPE: DNA
<213> ORGANISM: Artificial Sequence
<220> FEATURE:
<223> OTHER INFORMATION: MYC19-6R

<400> SEQUENCE: 67
ggtcgcagat gaaactctgg t                                                  21

<210> SEQ ID NO 68
<211> LENGTH: 20
<212> TYPE: DNA
<213> ORGANISM: Artificial Sequence
<220> FEATURE:
<223> OTHER INFORMATION: MYC20-6R

<400> SEQUENCE: 68
gatgaaggtc tcgtcgtccg                                                    20

<210> SEQ ID NO 69
<211> LENGTH: 24

-continued

```
<212> TYPE: DNA
<213> ORGANISM: Artificial Sequence
<220> FEATURE:
<223> OTHER INFORMATION: MYC21-6R

<400> SEQUENCE: 69
acagtcctgg atgatgatgt tttt                                            24

<210> SEQ ID NO 70
<211> LENGTH: 19
<212> TYPE: DNA
<213> ORGANISM: Artificial Sequence
<220> FEATURE:
<223> OTHER INFORMATION: MYC22-6R

<400> SEQUENCE: 70
ccgagaagcc gctccacat                                                  19

<210> SEQ ID NO 71
<211> LENGTH: 14
<212> TYPE: DNA
<213> ORGANISM: Artificial Sequence
<220> FEATURE:
<223> OTHER INFORMATION: MYC30-6R

<400> SEQUENCE: 71
gcggcggcgc tcag                                                       14

<210> SEQ ID NO 72
<211> LENGTH: 20
<212> TYPE: DNA
<213> ORGANISM: Artificial Sequence
<220> FEATURE:
<223> OTHER INFORMATION: MYC31-6R

<400> SEQUENCE: 72
aggggtcgat gcactctgag                                                 20

<210> SEQ ID NO 73
<211> LENGTH: 19
<212> TYPE: DNA
<213> ORGANISM: Artificial Sequence
<220> FEATURE:
<223> OTHER INFORMATION: MYC32-6R

<400> SEQUENCE: 73
gggtagggga agaccaccg                                                  19

<210> SEQ ID NO 74
<211> LENGTH: 20
<212> TYPE: DNA
<213> ORGANISM: Artificial Sequence
<220> FEATURE:
<223> OTHER INFORMATION: MYC33-6R

<400> SEQUENCE: 74
gcgagctgct gtcgttgaga                                                 20

<210> SEQ ID NO 75
<211> LENGTH: 17
<212> TYPE: DNA
<213> ORGANISM: Artificial Sequence
<220> FEATURE:
<223> OTHER INFORMATION: MYC34-6R

<400> SEQUENCE: 75
```
cgaggcgcag gacttgg                                                              17

<210> SEQ ID NO 76
<211> LENGTH: 20
<212> TYPE: DNA
<213> ORGANISM: Artificial Sequence
<220> FEATURE:
<223> OTHER INFORMATION: MYC35-6R

<400> SEQUENCE: 76
gagaaggcgc tggagtcttg                                                          20

<210> SEQ ID NO 77
<211> LENGTH: 20
<212> TYPE: DNA
<213> ORGANISM: Artificial Sequence
<220> FEATURE:
<223> OTHER INFORMATION: MYC36-6R

<400> SEQUENCE: 77
gcagagaatc cgaggacgga                                                          20

<210> SEQ ID NO 78
<211> LENGTH: 20
<212> TYPE: DNA
<213> ORGANISM: Artificial Sequence
<220> FEATURE:
<223> OTHER INFORMATION: MYC37-6R

<400> SEQUENCE: 78
ggaggactcc gtcgaggaga                                                          20

<210> SEQ ID NO 79
<211> LENGTH: 15
<212> TYPE: DNA
<213> ORGANISM: Artificial Sequence
<220> FEATURE:
<223> OTHER INFORMATION: MYC38-6R

<400> SEQUENCE: 79
ggggctgccc tgcgg                                                               15

<210> SEQ ID NO 80
<211> LENGTH: 18
<212> TYPE: DNA
<213> ORGANISM: Artificial Sequence
<220> FEATURE:
<223> OTHER INFORMATION: MYC39-6R

<400> SEQUENCE: 80
atggagcacc aggggctc                                                           18

<210> SEQ ID NO 81
<211> LENGTH: 18
<212> TYPE: DNA
<213> ORGANISM: Artificial Sequence
<220> FEATURE:
<223> OTHER INFORMATION: MYC40-6R

<400> SEQUENCE: 81
ggtgggcggt gtctcctc                                                           18

<210> SEQ ID NO 82
<211> LENGTH: 20
<212> TYPE: DNA
<213> ORGANISM: Artificial Sequence

<220> FEATURE:
<223> OTHER INFORMATION: MYC41-6R

<400> SEQUENCE: 82
tcctcagagt cgctgctggt                                                                                         20

<210> SEQ ID NO 83
<211> LENGTH: 25
<212> TYPE: DNA
<213> ORGANISM: Artificial Sequence
<220> FEATURE:
<223> OTHER INFORMATION: MYC42-6R

<400> SEQUENCE: 83
gatttcttcc tcatcttctt gttcc                                                                                   25

<210> SEQ ID NO 84
<211> LENGTH: 24
<212> TYPE: DNA
<213> ORGANISM: Artificial Sequence
<220> FEATURE:
<223> OTHER INFORMATION: MYC43-6R

<400> SEQUENCE: 84
cctcttttcc acagaaacaa catc                                                                                    24

<210> SEQ ID NO 85
<211> LENGTH: 19
<212> TYPE: DNA
<213> ORGANISM: Artificial Sequence
<220> FEATURE:
<223> OTHER INFORMATION: MYC44-6R

<400> SEQUENCE: 85
accttttgcc aggagcctg                                                                                          19

<210> SEQ ID NO 86
<211> LENGTH: 23
<212> TYPE: DNA
<213> ORGANISM: Artificial Sequence
<220> FEATURE:
<223> OTHER INFORMATION: MYC45-6R

<400> SEQUENCE: 86
agcagaaggt gatccagact ctg                                                                                     23

<210> SEQ ID NO 87
<211> LENGTH: 19
<212> TYPE: DNA
<213> ORGANISM: Artificial Sequence
<220> FEATURE:
<223> OTHER INFORMATION: MYC46-6R

<400> SEQUENCE: 87
gaggtttgct gtggcctcc                                                                                          19

<210> SEQ ID NO 88
<211> LENGTH: 20
<212> TYPE: DNA
<213> ORGANISM: Artificial Sequence
<220> FEATURE:
<223> OTHER INFORMATION: MYC47-6R

<400> SEQUENCE: 88
gaggaccagt gggctgtgag                                                                                         20

-continued

```
<210> SEQ ID NO 89
<211> LENGTH: 20
<212> TYPE: DNA
<213> ORGANISM: Artificial Sequence
<220> FEATURE:
<223> OTHER INFORMATION: MYC48-6R

<400> SEQUENCE: 89
gtggagacgt ggcacctctt                                               20

<210> SEQ ID NO 90
<211> LENGTH: 21
<212> TYPE: DNA
<213> ORGANISM: Artificial Sequence
<220> FEATURE:
<223> OTHER INFORMATION: MYC49-6R

<400> SEQUENCE: 90
gctgcgtagt tgtgctgatg t                                             21

<210> SEQ ID NO 91
<211> LENGTH: 18
<212> TYPE: DNA
<213> ORGANISM: Artificial Sequence
<220> FEATURE:
<223> OTHER INFORMATION: MYC50-6R

<400> SEQUENCE: 91
ttccgagtgg agggaggc                                                 18

<210> SEQ ID NO 92
<211> LENGTH: 21
<212> TYPE: DNA
<213> ORGANISM: Artificial Sequence
<220> FEATURE:
<223> OTHER INFORMATION: MYC51-6R

<400> SEQUENCE: 92
ctcttggcag caggatagtc c                                             21

<210> SEQ ID NO 93
<211> LENGTH: 24
<212> TYPE: DNA
<213> ORGANISM: Artificial Sequence
<220> FEATURE:
<223> OTHER INFORMATION: MYC52-6R

<400> SEQUENCE: 93
actctgacac tgtccaactt gacc                                          24

<210> SEQ ID NO 94
<211> LENGTH: 23
<212> TYPE: DNA
<213> ORGANISM: Artificial Sequence
<220> FEATURE:
<223> OTHER INFORMATION: MYC53-6R

<400> SEQUENCE: 94
ggttgttgct gatctgtctc agg                                           23

<210> SEQ ID NO 95
<211> LENGTH: 18
<212> TYPE: DNA
<213> ORGANISM: Artificial Sequence
<220> FEATURE:
<223> OTHER INFORMATION: MYC54-6R
```

-continued

<400> SEQUENCE: 95
tggggctggt gcattttc                                                    18

<210> SEQ ID NO 96
<211> LENGTH: 18
<212> TYPE: DNA
<213> ORGANISM: Artificial Sequence
<220> FEATURE:
<223> OTHER INFORMATION: MYC55-6R

<400> SEQUENCE: 96
cctcggtgtc cgaggacc                                                    18

<210> SEQ ID NO 97
<211> LENGTH: 22
<212> TYPE: DNA
<213> ORGANISM: Artificial Sequence
<220> FEATURE:
<223> OTHER INFORMATION: MYC56-6R

<400> SEQUENCE: 97
tgtgttcgcc tcttgacatt ct                                               22

<210> SEQ ID NO 98
<211> LENGTH: 18
<212> TYPE: DNA
<213> ORGANISM: Artificial Sequence
<220> FEATURE:
<223> OTHER INFORMATION: MYC57-6R

<400> SEQUENCE: 98
tggcgctcca agacgttg                                                    18

<210> SEQ ID NO 99
<211> LENGTH: 22
<212> TYPE: DNA
<213> ORGANISM: Artificial Sequence
<220> FEATURE:
<223> OTHER INFORMATION: MYC58-6R

<400> SEQUENCE: 99
ccgttttagc tcgttcctcc tc                                               22

<210> SEQ ID NO 100
<211> LENGTH: 25
<212> TYPE: DNA
<213> ORGANISM: Artificial Sequence
<220> FEATURE:
<223> OTHER INFORMATION: MYC62-6R

<400> SEQUENCE: 100 tggcttttttt aaggataact acctt                                          25

<210> SEQ ID NO 101
<211> LENGTH: 21
<212> TYPE: DNA
<213> ORGANISM: Artificial Sequence
<220> FEATURE:
<223> OTHER INFORMATION: MYC63-6R

<400> SEQUENCE: 101
ggacggacag gatgtatgct g                                                21

<210> SEQ ID NO 102

```
<211> LENGTH: 21
<212> TYPE: DNA
<213> ORGANISM: Artificial Sequence
<220> FEATURE:
<223> OTHER INFORMATION: MYC64-6R

<400> SEQUENCE: 102
tgagcttttg ctcctctgct t                                                 21

<210> SEQ ID NO 103
<211> LENGTH: 19
<212> TYPE: DNA
<213> ORGANISM: Artificial Sequence
<220> FEATURE:
<223> OTHER INFORMATION: MYCN1-6R

<400> SEQUENCE: 103
gctcgctgga ctgagccct                                                    19

<210> SEQ ID NO 104
<211> LENGTH: 21
<212> TYPE: DNA
<213> ORGANISM: Artificial Sequence
<220> FEATURE:
<223> OTHER INFORMATION: MYCN2-6R

<400> SEQUENCE: 104
gaaggcatcg tttgaggatc a                                                 21

<210> SEQ ID NO 105
<211> LENGTH: 19
<212> TYPE: DNA
<213> ORGANISM: Artificial Sequence
<220> FEATURE:
<223> OTHER INFORMATION: MYCN3-6R

<400> SEQUENCE: 105
ttgtgctgct ggtggatgg                                                    19

<210> SEQ ID NO 106
<211> LENGTH: 23
<212> TYPE: DNA
<213> ORGANISM: Artificial Sequence
<220> FEATURE:
<223> OTHER INFORMATION: MYCN6-6R

<400> SEQUENCE: 106
ctctttatct tcttctgtgg ggg                                               23

<210> SEQ ID NO 107
<211> LENGTH: 16
<212> TYPE: DNA
<213> ORGANISM: Artificial Sequence
<220> FEATURE:
<223> OTHER INFORMATION: MYCN7-6R

<400> SEQUENCE: 107
acgtggggac gcctcg                                                       16

<210> SEQ ID NO 108
<211> LENGTH: 20
<212> TYPE: DNA
<213> ORGANISM: Artificial Sequence
<220> FEATURE:
<223> OTHER INFORMATION: MYCN8-6R

<400> SEQUENCE: 108
```
gggatgacac tcttgagcgg                                                   20

<210> SEQ ID NO 109
<211> LENGTH: 21
<212> TYPE: DNA
<213> ORGANISM: Artificial Sequence
<220> FEATURE:
<223> OTHER INFORMATION: MYCN9-6R

<400> SEQUENCE: 109
ctcaagctct tagcctttgg g                                                 21

<210> SEQ ID NO 110
<211> LENGTH: 19
<212> TYPE: DNA
<213> ORGANISM: Artificial Sequence
<220> FEATURE:
<223> OTHER INFORMATION: MYCN10-6R

<400> SEQUENCE: 110
cgagtcagag tttcggggg                                                    19

<210> SEQ ID NO 111
<211> LENGTH: 19
<212> TYPE: DNA
<213> ORGANISM: Artificial Sequence
<220> FEATURE:
<223> OTHER INFORMATION: MYCN11-6R

<400> SEQUENCE: 111
tgcgacgctc actgtcctc                                                    19

<210> SEQ ID NO 112
<211> LENGTH: 21
<212> TYPE: DNA
<213> ORGANISM: Artificial Sequence
<220> FEATURE:
<223> OTHER INFORMATION: MYCN12-6R

<400> SEQUENCE: 112
gctccaggat gttgtggttt c                                                 21

<210> SEQ ID NO 113
<211> LENGTH: 15
<212> TYPE: DNA
<213> ORGANISM: Artificial Sequence
<220> FEATURE:
<223> OTHER INFORMATION: MYCN13-6R

<400> SEQUENCE: 113
cgttgcggcg ctggc                                                        15

<210> SEQ ID NO 114
<211> LENGTH: 21
<212> TYPE: DNA
<213> ORGANISM: Artificial Sequence
<220> FEATURE:
<223> OTHER INFORMATION: MYCN14-6R

<400> SEQUENCE: 114
tgagaaagct ggaccgaagg t                                                 21

<210> SEQ ID NO 115
<211> LENGTH: 18
<212> TYPE: DNA

-continued

```
<213> ORGANISM: Artificial Sequence
<220> FEATURE:
<223> OTHER INFORMATION: MYCN15-6R

<400> SEQUENCE: 115
gcacgtggtc cctgagcg                                                    18

<210> SEQ ID NO 116
<211> LENGTH: 24
<212> TYPE: DNA
<213> ORGANISM: Artificial Sequence
<220> FEATURE:
<223> OTHER INFORMATION: MYCN16-6R

<400> SEQUENCE: 116
ccttctcatt ctttaccaac tccg                                            24

<210> SEQ ID NO 117
<211> LENGTH: 19
<212> TYPE: DNA
<213> ORGANISM: Artificial Sequence
<220> FEATURE:
<223> OTHER INFORMATION: MYCN17-6R

<400> SEQUENCE: 117
aaaatgacca ccttggcgg                                                  19

<210> SEQ ID NO 118
<211> LENGTH: 23
<212> TYPE: DNA
<213> ORGANISM: Artificial Sequence
<220> FEATURE:
<223> OTHER INFORMATION: MYCN18-6R

<400> SEQUENCE: 118
ggacatactc agtggccttt ttc                                             23

<210> SEQ ID NO 119
<211> LENGTH: 18
<212> TYPE: DNA
<213> ORGANISM: Artificial Sequence
<220> FEATURE:
<223> OTHER INFORMATION: MYCN19-6R

<400> SEQUENCE: 119
cctcggcctg gagggagt                                                   18

<210> SEQ ID NO 120
<211> LENGTH: 20
<212> TYPE: DNA
<213> ORGANISM: Artificial Sequence
<220> FEATURE:
<223> OTHER INFORMATION: MYCN20-6R

<400> SEQUENCE: 120
ttccagcaaa agctggtgct                                                 20

<210> SEQ ID NO 121
<211> LENGTH: 21
<212> TYPE: DNA
<213> ORGANISM: Artificial Sequence
<220> FEATURE:
<223> OTHER INFORMATION: MYCN21-6R

<400> SEQUENCE: 121
tcttgcctgc aatttttcct t                                               21
```

<210> SEQ ID NO 122
<211> LENGTH: 23
<212> TYPE: DNA
<213> ORGANISM: Artificial Sequence
<220> FEATURE:
<223> OTHER INFORMATION: MYCN22-6R

<400> SEQUENCE: 122
attttcttta gcaactgctg ctg                                                23

<210> SEQ ID NO 123
<211> LENGTH: 19
<212> TYPE: DNA
<213> ORGANISM: Artificial Sequence
<220> FEATURE:
<223> OTHER INFORMATION: MYCN23-6R

<400> SEQUENCE: 123
gcaagtccga gcgtgttca                                                     19

<210> SEQ ID NO 124
<211> LENGTH: 23
<212> TYPE: DNA
<213> ORGANISM: Artificial Sequence
<220> FEATURE:
<223> OTHER INFORMATION: MYCN24-6R

<400> SEQUENCE: 124
tgtccagttt tgagaagcgt cta                                                23

<210> SEQ ID NO 125
<211> LENGTH: 22
<212> TYPE: DNA
<213> ORGANISM: Artificial Sequence
<220> FEATURE:
<223> OTHER INFORMATION: MYCN25-6R

<400> SEQUENCE: 125
aaatgtgcaa agtggcagtg ac                                                 22

<210> SEQ ID NO 126
<211> LENGTH: 27
<212> TYPE: DNA
<213> ORGANISM: Artificial Sequence
<220> FEATURE:
<223> OTHER INFORMATION: MYCN26-6R

<400> SEQUENCE: 126
cacaatgttt gtttaaaaaa aaaatca                                            27

<210> SEQ ID NO 127
<211> LENGTH: 27
<212> TYPE: DNA
<213> ORGANISM: Artificial Sequence
<220> FEATURE:
<223> OTHER INFORMATION: MYCN27-6R

<400> SEQUENCE: 127
aaagtaaacc aacattctta atgtcaa                                            27

<210> SEQ ID NO 128
<211> LENGTH: 19
<212> TYPE: DNA
<213> ORGANISM: Artificial Sequence
<220> FEATURE:

```
<223> OTHER INFORMATION: MYCN28-6R

<400> SEQUENCE: 128
tcgacagggg accgatttg                                          19

<210> SEQ ID NO 129
<211> LENGTH: 18
<212> TYPE: DNA
<213> ORGANISM: Artificial Sequence
<220> FEATURE:
<223> OTHER INFORMATION: MYCN29-6R

<400> SEQUENCE: 129
gcccacccag agccgaac                                           18

<210> SEQ ID NO 130
<211> LENGTH: 21
<212> TYPE: DNA
<213> ORGANISM: Artificial Sequence
<220> FEATURE:
<223> OTHER INFORMATION: MYCN30-6R

<400> SEQUENCE: 130
ccccacactg gtggtcctac t                                       21

<210> SEQ ID NO 131
<211> LENGTH: 20
<212> TYPE: DNA
<213> ORGANISM: Artificial Sequence
<220> FEATURE:
<223> OTHER INFORMATION: MYCN31-6R

<400> SEQUENCE: 131
tctccaaggt cccagcagaa                                         20

<210> SEQ ID NO 132
<211> LENGTH: 21
<212> TYPE: DNA
<213> ORGANISM: Artificial Sequence
<220> FEATURE:
<223> OTHER INFORMATION: MYCN34-6R

<400> SEQUENCE: 132
catggaggtg aggtggagga g                                       21

<210> SEQ ID NO 133
<211> LENGTH: 20
<212> TYPE: DNA
<213> ORGANISM: Artificial Sequence
<220> FEATURE:
<223> OTHER INFORMATION: MYCN35-6R

<400> SEQUENCE: 133
tcaccaacgt ttagcgctgt                                         20

<210> SEQ ID NO 134
<211> LENGTH: 18
<212> TYPE: DNA
<213> ORGANISM: Artificial Sequence
<220> FEATURE:
<223> OTHER INFORMATION: MYCN36-6R

<400> SEQUENCE: 134
cccagaggct cccaaccg                                           18
```

```
<210> SEQ ID NO 135
<211> LENGTH: 23
<212> TYPE: DNA
<213> ORGANISM: Artificial Sequence
<220> FEATURE:
<223> OTHER INFORMATION: MYCN37-6R

<400> SEQUENCE: 135
acacacaagg tgacttcaac agc                                                    23

<210> SEQ ID NO 136
<211> LENGTH: 23
<212> TYPE: DNA
<213> ORGANISM: Artificial Sequence
<220> FEATURE:
<223> OTHER INFORMATION: MYCN38-6R

<400> SEQUENCE: 136
tttctgttgt ttggaaactt gga                                                    23

<210> SEQ ID NO 137
<211> LENGTH: 25
<212> TYPE: DNA
<213> ORGANISM: Artificial Sequence
<220> FEATURE:
<223> OTHER INFORMATION: MYCN39-6R

<400> SEQUENCE: 137
caccatttta aaagaagga atgac                                                   25

<210> SEQ ID NO 138
<211> LENGTH: 22
<212> TYPE: DNA
<213> ORGANISM: Artificial Sequence
<220> FEATURE:
<223> OTHER INFORMATION: MYCN40-6R

<400> SEQUENCE: 138
gtggcatctg ctggaactta ag                                                     22

<210> SEQ ID NO 139
<211> LENGTH: 22
<212> TYPE: DNA
<213> ORGANISM: Artificial Sequence
<220> FEATURE:
<223> OTHER INFORMATION: MYCN41-6R

<400> SEQUENCE: 139
tatcaaatgg caaacccctt at                                                     22

<210> SEQ ID NO 140
<211> LENGTH: 19
<212> TYPE: DNA
<213> ORGANISM: Artificial Sequence
<220> FEATURE:
<223> OTHER INFORMATION: MYCN42-6R

<400> SEQUENCE: 140
cagaaatgtt ccccagggg                                                         19

<210> SEQ ID NO 141
<211> LENGTH: 23
<212> TYPE: DNA
<213> ORGANISM: Artificial Sequence
<220> FEATURE:
<223> OTHER INFORMATION: MYCN43-6R
```

-continued

<400> SEQUENCE: 141
ggcggatgtg tcaatggtat tta                                    23

<210> SEQ ID NO 142
<211> LENGTH: 26
<212> TYPE: DNA
<213> ORGANISM: Artificial Sequence
<220> FEATURE:
<223> OTHER INFORMATION: MYCN44-6R

<400> SEQUENCE: 142
tctcattacc caggatgtat acaaaa                                 26

<210> SEQ ID NO 143
<211> LENGTH: 16
<212> TYPE: DNA
<213> ORGANISM: Artificial Sequence
<220> FEATURE:
<223> OTHER INFORMATION: MYCN45-6R

<400> SEQUENCE: 143
ggccgcaaaa gccacc                                            16

<210> SEQ ID NO 144
<211> LENGTH: 29
<212> TYPE: DNA
<213> ORGANISM: Artificial Sequence
<220> FEATURE:
<223> OTHER INFORMATION: MYCN46-6R

<400> SEQUENCE: 144
acttaggtat gaacttccag tctaatact                              29

<210> SEQ ID NO 145
<211> LENGTH: 27
<212> TYPE: DNA
<213> ORGANISM: Artificial Sequence
<220> FEATURE:
<223> OTHER INFORMATION: MYCN47-6R

<400> SEQUENCE: 145
cctcaaacat tgaggtatta ttacagt                                27

<210> SEQ ID NO 146
<211> LENGTH: 35
<212> TYPE: DNA
<213> ORGANISM: Artificial Sequence
<220> FEATURE:
<223> OTHER INFORMATION: MYCN54-6R

<400> SEQUENCE: 146
catatatata tagtaaattt ctttacaaaa gtttc                       35

<210> SEQ ID NO 147
<211> LENGTH: 23
<212> TYPE: DNA
<213> ORGANISM: Artificial Sequence
<220> FEATURE:
<223> OTHER INFORMATION: MYCN55-6R

<400> SEQUENCE: 147
gaagaaacag gctaggaaaa agg                                    23

<210> SEQ ID NO 148
<211> LENGTH: 26

```
<212> TYPE: DNA
<213> ORGANISM: Artificial Sequence
<220> FEATURE:
<223> OTHER INFORMATION: MYCN56-6R

<400> SEQUENCE: 148
ccaaacatga acaaatacat taacag                                                    26

<210> SEQ ID NO 149
<211> LENGTH: 23
<212> TYPE: DNA
<213> ORGANISM: Artificial Sequence
<220> FEATURE:
<223> OTHER INFORMATION: MYCN57-6R

<400> SEQUENCE: 149
ttgcatttac ccagttctat gca                                                       23

<210> SEQ ID NO 150
<211> LENGTH: 27
<212> TYPE: DNA
<213> ORGANISM: Artificial Sequence
<220> FEATURE:
<223> OTHER INFORMATION: MYCN58-6R

<400> SEQUENCE: 150
cattttgaag aaattaaaca cagaact                                                   27

<210> SEQ ID NO 151
<211> LENGTH: 28
<212> TYPE: DNA
<213> ORGANISM: Artificial Sequence
<220> FEATURE:
<223> OTHER INFORMATION: MYCN59-6R

<400> SEQUENCE: 151
tgctataaga tgcagcacta aatatata                                                  28

<210> SEQ ID NO 152
<211> LENGTH: 27
<212> TYPE: DNA
<213> ORGANISM: Artificial Sequence
<220> FEATURE:
<223> OTHER INFORMATION: MYCN60-6R

<400> SEQUENCE: 152
ttttcataaa catgaggtat ttcaaag                                                   27

<210> SEQ ID NO 153
<211> LENGTH: 23
<212> TYPE: DNA
<213> ORGANISM: Artificial Sequence
<220> FEATURE:
<223> OTHER INFORMATION: MALAT11-4R

<400> SEQUENCE: 153
caggctggtt atgactcaga aga                                                       23

<210> SEQ ID NO 154
<211> LENGTH: 22
<212> TYPE: DNA
<213> ORGANISM: Artificial Sequence
<220> FEATURE:
<223> OTHER INFORMATION: MALAT12-4R

<400> SEQUENCE: 154
```

-continued tgcatctagg ccatcatact gc                                                    22

<210> SEQ ID NO 155
<211> LENGTH: 23
<212> TYPE: DNA
<213> ORGANISM: Artificial Sequence
<220> FEATURE:
<223> OTHER INFORMATION: MALAT13-4R

<400> SEQUENCE: 155
attcaccaag gagctgtttt ctc                                                   23

<210> SEQ ID NO 156
<211> LENGTH: 28
<212> TYPE: DNA
<213> ORGANISM: Artificial Sequence
<220> FEATURE:
<223> OTHER INFORMATION: MALAT14-4R

<400> SEQUENCE: 156
atataatctt ttctgccttt acttatca                                             28

<210> SEQ ID NO 157
<211> LENGTH: 23
<212> TYPE: DNA
<213> ORGANISM: Artificial Sequence
<220> FEATURE:
<223> OTHER INFORMATION: MALAT15-4R

<400> SEQUENCE: 157
ttattcccca atggaggtat gac                                                   23

<210> SEQ ID NO 158
<211> LENGTH: 26
<212> TYPE: DNA
<213> ORGANISM: Artificial Sequence
<220> FEATURE:
<223> OTHER INFORMATION: MALAT16-4R

<400> SEQUENCE: 158
cagtagtaag aatctcaggg ttatgc                                               26

<210> SEQ ID NO 159
<211> LENGTH: 25
<212> TYPE: DNA
<213> ORGANISM: Artificial Sequence
<220> FEATURE:
<223> OTHER INFORMATION: MALAT17-4R

<400> SEQUENCE: 159
tggcatatgc agataatgtt ctcat                                                 25

<210> SEQ ID NO 160
<211> LENGTH: 25
<212> TYPE: DNA
<213> ORGANISM: Artificial Sequence
<220> FEATURE:
<223> OTHER INFORMATION: MALAT18-4R

<400> SEQUENCE: 160
tagctttcat ttgcttaaaa ttttt                                                 25

<210> SEQ ID NO 161
<211> LENGTH: 25
<212> TYPE: DNA
<213> ORGANISM: Artificial Sequence

```
<220> FEATURE:
<223> OTHER INFORMATION: MALAT19-4R

<400> SEQUENCE: 161
ggtagattcc gtaactttaa attgg                                          25

<210> SEQ ID NO 162
<211> LENGTH: 26
<212> TYPE: DNA
<213> ORGANISM: Artificial Sequence
<220> FEATURE:
<223> OTHER INFORMATION: MALAT110-4R

<400> SEQUENCE: 162
gcttgacaag caattaactt taaaat                                         26

<210> SEQ ID NO 163
<211> LENGTH: 27
<212> TYPE: DNA
<213> ORGANISM: Artificial Sequence
<220> FEATURE:
<223> OTHER INFORMATION: MALAT111-4R

<400> SEQUENCE: 163
catcaattca ttatttttgt ggttata                                        27

<210> SEQ ID NO 164
<211> LENGTH: 25
<212> TYPE: DNA
<213> ORGANISM: Artificial Sequence
<220> FEATURE:
<223> OTHER INFORMATION: MALAT112-4R

<400> SEQUENCE: 164
gacattgcct cttcattgta tttct                                          25

<210> SEQ ID NO 165
<211> LENGTH: 26
<212> TYPE: DNA
<213> ORGANISM: Artificial Sequence
<220> FEATURE:
<223> OTHER INFORMATION: MALAT113-4R

<400> SEQUENCE: 165
ttttgtaaaa gcagtatttt gagatg                                         26

<210> SEQ ID NO 166
<211> LENGTH: 24
<212> TYPE: DNA
<213> ORGANISM: Artificial Sequence
<220> FEATURE:
<223> OTHER INFORMATION: MALAT114-4R

<400> SEQUENCE: 166
catttctttt cgcttttatt ctgc                                           24

<210> SEQ ID NO 167
<211> LENGTH: 27
<212> TYPE: DNA
<213> ORGANISM: Artificial Sequence
<220> FEATURE:
<223> OTHER INFORMATION: MALAT115-4R

<400> SEQUENCE: 167
tccaggatta atgtagtgta acatttt                                        27
```

```
<210> SEQ ID NO 168
<211> LENGTH: 25
<212> TYPE: DNA
<213> ORGANISM: Artificial Sequence
<220> FEATURE:
<223> OTHER INFORMATION: MALAT116-4R

<400> SEQUENCE: 168
tctcatttat ttcggcttct tttat                                        25

<210> SEQ ID NO 169
<211> LENGTH: 23
<212> TYPE: DNA
<213> ORGANISM: Artificial Sequence
<220> FEATURE:
<223> OTHER INFORMATION: MALAT117-4R

<400> SEQUENCE: 169
aatccacttg atcccaactc atc                                          23

<210> SEQ ID NO 170
<211> LENGTH: 20
<212> TYPE: DNA
<213> ORGANISM: Artificial Sequence
<220> FEATURE:
<223> OTHER INFORMATION: MALAT118-4R

<400> SEQUENCE: 170
gcacacagca cagcctcctc                                              20

<210> SEQ ID NO 171
<211> LENGTH: 22
<212> TYPE: DNA
<213> ORGANISM: Artificial Sequence
<220> FEATURE:
<223> OTHER INFORMATION: MALAT119-4R

<400> SEQUENCE: 171
gtctgaggca aacgaaacat tg                                           22

<210> SEQ ID NO 172
<211> LENGTH: 27
<212> TYPE: DNA
<213> ORGANISM: Artificial Sequence
<220> FEATURE:
<223> OTHER INFORMATION: MALAT120-4R

<400> SEQUENCE: 172
aactcttctg ataacgaaga gatacct                                      27

<210> SEQ ID NO 173
<211> LENGTH: 21
<212> TYPE: DNA
<213> ORGANISM: Artificial Sequence
<220> FEATURE:
<223> OTHER INFORMATION: MALAT121-4R

<400> SEQUENCE: 173
tgctcccaga tgaaatgaag c                                            21

<210> SEQ ID NO 174
<211> LENGTH: 22
<212> TYPE: DNA
<213> ORGANISM: Artificial Sequence
<220> FEATURE:
<223> OTHER INFORMATION: MALAT122-4R
```

<400> SEQUENCE: 174
ttaacagctg cctgctgttt tc                                            22

<210> SEQ ID NO 175
<211> LENGTH: 25
<212> TYPE: DNA
<213> ORGANISM: Artificial Sequence
<220> FEATURE:
<223> OTHER INFORMATION: MALAT123-4R

<400> SEQUENCE: 175
tgcagatgca agttaaactt atctg                                         25

<210> SEQ ID NO 176
<211> LENGTH: 25
<212> TYPE: DNA
<213> ORGANISM: Artificial Sequence
<220> FEATURE:
<223> OTHER INFORMATION: MALAT124-4R

<400> SEQUENCE: 176
agcacttatc cctaacatgc aatac                                         25

<210> SEQ ID NO 177
<211> LENGTH: 27
<212> TYPE: DNA
<213> ORGANISM: Artificial Sequence
<220> FEATURE:
<223> OTHER INFORMATION: MALAT125-4R

<400> SEQUENCE: 177
ttaagaactc cacagctctt aaaaata                                       27

<210> SEQ ID NO 178
<211> LENGTH: 23
<212> TYPE: DNA
<213> ORGANISM: Artificial Sequence
<220> FEATURE:
<223> OTHER INFORMATION: MALAT126-4R

<400> SEQUENCE: 178
ggagaaagtg ccatggttga tat                                           23

<210> SEQ ID NO 179
<211> LENGTH: 19
<212> TYPE: DNA
<213> ORGANISM: Artificial Sequence
<220> FEATURE:
<223> OTHER INFORMATION: MALAT127-4R

<400> SEQUENCE: 179
tcccctaggg aaggggtca                                                19

<210> SEQ ID NO 180
<211> LENGTH: 24
<212> TYPE: DNA
<213> ORGANISM: Artificial Sequence
<220> FEATURE:
<223> OTHER INFORMATION: MALAT128-4R

<400> SEQUENCE: 180
tggaaaaatt tctcaatcct gaaa                                          24

<210> SEQ ID NO 181

```
<211> LENGTH: 23
<212> TYPE: DNA
<213> ORGANISM: Artificial Sequence
<220> FEATURE:
<223> OTHER INFORMATION: MALAT129-4R

<400> SEQUENCE: 181
cctacaattt taaaaaggct cga                                              23

<210> SEQ ID NO 182
<211> LENGTH: 21
<212> TYPE: DNA
<213> ORGANISM: Artificial Sequence
<220> FEATURE:
<223> OTHER INFORMATION: MALAT130-4R

<400> SEQUENCE: 182
ctgaagccca caggaacaag t                                                21

<210> SEQ ID NO 183
<211> LENGTH: 26
<212> TYPE: DNA
<213> ORGANISM: Artificial Sequence
<220> FEATURE:
<223> OTHER INFORMATION: MALAT131-4R

<400> SEQUENCE: 183
tctgagtgaa gtgtactatc ccatca                                          26

<210> SEQ ID NO 184
<211> LENGTH: 25
<212> TYPE: DNA
<213> ORGANISM: Artificial Sequence
<220> FEATURE:
<223> OTHER INFORMATION: MALAT132-4R

<400> SEQUENCE: 184
gaaattattt aaagatgcaa atgcc                                           25

<210> SEQ ID NO 185
<211> LENGTH: 26
<212> TYPE: DNA
<213> ORGANISM: Artificial Sequence
<220> FEATURE:
<223> OTHER INFORMATION: MALAT133-4R

<400> SEQUENCE: 185
gcactgatca ctttagaggc ttttaa                                          26

<210> SEQ ID NO 186
<211> LENGTH: 24
<212> TYPE: DNA
<213> ORGANISM: Artificial Sequence
<220> FEATURE:
<223> OTHER INFORMATION: MALAT134-4R

<400> SEQUENCE: 186
caaatttcct tagttggcat caag                                            24

<210> SEQ ID NO 187
<211> LENGTH: 23
<212> TYPE: DNA
<213> ORGANISM: Artificial Sequence
<220> FEATURE:
<223> OTHER INFORMATION: MALAT135-4R

<400> SEQUENCE: 187
```
gccttcagag attcaatgct aaa                                                23

<210> SEQ ID NO 188
<211> LENGTH: 25
<212> TYPE: DNA
<213> ORGANISM: Artificial Sequence
<220> FEATURE:
<223> OTHER INFORMATION: MALAT136-4R

<400> SEQUENCE: 188
cacatcatgc tattcctttc ataga                                              25

<210> SEQ ID NO 189
<211> LENGTH: 28
<212> TYPE: DNA
<213> ORGANISM: Artificial Sequence
<220> FEATURE:
<223> OTHER INFORMATION: MALAT137-4R

<400> SEQUENCE: 189
ttttagcagt aacatctgat tctaacag                                          28

<210> SEQ ID NO 190
<211> LENGTH: 28
<212> TYPE: DNA
<213> ORGANISM: Artificial Sequence
<220> FEATURE:
<223> OTHER INFORMATION: MALAT138-4R

<400> SEQUENCE: 190
ctacacaatt tacatcacaa catgtaaa                                          28

<210> SEQ ID NO 191
<211> LENGTH: 28
<212> TYPE: DNA
<213> ORGANISM: Artificial Sequence
<220> FEATURE:
<223> OTHER INFORMATION: MALAT139-4R

<400> SEQUENCE: 191
ttattatttt gaatgattta atggtttt                                          28

<210> SEQ ID NO 192
<211> LENGTH: 33
<212> TYPE: DNA
<213> ORGANISM: Artificial Sequence
<220> FEATURE:
<223> OTHER INFORMATION: MALAT140-4R

<400> SEQUENCE: 192
ttctaaaagt atacattctc taataaaaat agt                                    33

<210> SEQ ID NO 193
<211> LENGTH: 29
<212> TYPE: DNA
<213> ORGANISM: Artificial Sequence
<220> FEATURE:
<223> OTHER INFORMATION: MALAT141-4R

<400> SEQUENCE: 193
cactatttta tttaaataag gagacagct                                         29

<210> SEQ ID NO 194
<211> LENGTH: 24
<212> TYPE: DNA

-continued

```
<213> ORGANISM: Artificial Sequence
<220> FEATURE:
<223> OTHER INFORMATION: MALAT142-4R

<400> SEQUENCE: 194
ccccaacact gaactacaga caaa                                       24

<210> SEQ ID NO 195
<211> LENGTH: 20
<212> TYPE: DNA
<213> ORGANISM: Artificial Sequence
<220> FEATURE:
<223> OTHER INFORMATION: MALAT143-4R

<400> SEQUENCE: 195
aagaatcccc cccaagattg                                           20

<210> SEQ ID NO 196
<211> LENGTH: 27
<212> TYPE: DNA
<213> ORGANISM: Artificial Sequence
<220> FEATURE:
<223> OTHER INFORMATION: MALAT144-4R

<400> SEQUENCE: 196
gcagacaaag tttctgaaag attagag                                   27

<210> SEQ ID NO 197
<211> LENGTH: 25
<212> TYPE: DNA
<213> ORGANISM: Artificial Sequence
<220> FEATURE:
<223> OTHER INFORMATION: MALAT145-4R

<400> SEQUENCE: 197
tgatctggtc cattaaagag tgttc                                     25

<210> SEQ ID NO 198
<211> LENGTH: 20
<212> TYPE: DNA
<213> ORGANISM: Artificial Sequence
<220> FEATURE:
<223> OTHER INFORMATION: MALAT146-4R

<400> SEQUENCE: 198
tcgttcttcc gctcaaatcc                                           20

<210> SEQ ID NO 199
<211> LENGTH: 25
<212> TYPE: DNA
<213> ORGANISM: Artificial Sequence
<220> FEATURE:
<223> OTHER INFORMATION: MALAT147-4R

<400> SEQUENCE: 199
tgtctttcct gccttaaagt tacat                                     25

<210> SEQ ID NO 200
<211> LENGTH: 517
<212> TYPE: RNA
<213> ORGANISM: Homo sapiens
<220> FEATURE:
<221> NAME/KEY: misc_feature
<222> LOCATION: (1)..(517)
<223> OTHER INFORMATION: HLX2-7 lnc RNA sequence

<400> SEQUENCE: 200
```

```
augaccucaa acacuugugc uuggcgaguu uaugucuggg ugccuggaca caugcgggaa      60
uaaacacaca cacacacaca cacacacaca cacauucgau guuacugcau uccuucaucc     120
auucauuuuu uucauugcag uauuuauggg gauccuugug aguguuugca ccauagagaa     180
aaaaguauuu gacuaagcau uaaccauucc agcuaagaga ucaguguuug ucauucaaaa     240
uagcugaggu gguugggaga ggacagccag uauuccccaa aagagguuua uuaguuuccu     300
aggcugcugu cacaaauuga cacagacuua gugacuuaaa acaacagaaa uguguuugug     360
ucacuacauu cucugcuucu cuggcacaug gacucuucuu cugcauccag uuuuccucug     420
ucuuccucuc auaagcaugc gugugguagc auuuagcguc cacccaggca aucuagauua     480
aucucucacc ucaagcuccu uaacugaauc acaucug                             517
```

```
<210> SEQ ID NO 201
<211> LENGTH: 703
<212> TYPE: RNA
<213> ORGANISM: Homo sapiens
<220> FEATURE:
<221> NAME/KEY: misc_feature
<222> LOCATION: (1)..(703)
<223> OTHER INFORMATION: SPRY4-IT lncRNA sequence

<400> SEQUENCE: 201
```

```
guagagaugg ggguuucauc cguuugguca ggcuggucuu gaacuccuga ccucaaguga      60
ucugccuacc uuggccuccc aaaaggcuga gauuacaggc augagccacu gcgccaggcc     120
uucuuucuuu ucuuuuuuuc uuucuuuuuu uuuuugagac aucauuuagc ugugcugagg     180
gguucuuaaa uaggcagcuc agaaaauugu uuuccuuugu cagccacaua aauucagcag     240
aggcucuugg agggucccug cuggugaggg gugaggccag caguggaacu cugauuuggu     300
uuuugcugag cuggugguug aaaggaaucc uacuacaucg ggguuauaau agggaagaua     360
cauuuuagaa uaugcccagu ggagccaucg gaugcugcau cguccccaga gagccaaguc     420
aucgugggcc aagcucccau ccccaugucu ggccucaacu gcaggcccag auguugacag     480
cugccucugg aggguuaugg gagccuguga augccaacau ccccauugcc ugcagcggcu     540
gcucccaucc uggcuuccug gugggacuuu uccaugaauu ggggaaucug cuuucugauu     600
ccaaggccua uuaaaauuuc ugagcauugc ccauuucuuu ugcuuuaucu guaggacaug     660
ggcuguuuuu aaagaaccuc acaaaugaaa aaaaaaaaa aaa                        703
```

```
<210> SEQ ID NO 202
<211> LENGTH: 3721
<212> TYPE: RNA
<213> ORGANISM: Homo sapiens
<220> FEATURE:
<221> NAME/KEY: misc_feature
<222> LOCATION: (1)..(3721)
<223> OTHER INFORMATION: MYC RNA sequence

<400> SEQUENCE: 202
```

```
aacucgcugu aguaauucca gcgagaggca gagggagcga gcgggcggcc ggcuagggug      60
gaagagccgg gcgagcagag cugcgcugcg ggcguccugg gaagggagau ccggagcgaa     120
uagggggcuu cgccucuggc ccagcccucc cgcugauccc ccagccagcg guccgcaacc     180
cuugccgcau ccacgaaacu uugcccauag cagcgggcgg gcacuuugca cuggaacuua     240
caacacccga gcaaggacgc gacucucccg acgcggggag gcuauucugc ccauuugggg     300
acacuucccc gccgcugcca ggacccgcuu cucugaaagg cucuccuugc agcugcuuag     360
```

-continued

```
acgcuggauu uuuuucgggu aguggaaaac cagcagccuc ccgcgacgau gccccucaac      420
guuagcuuca ccaacaggaa cuaugaccuc gacuacgacu cggugcagcc guauuucuac      480
ugcgacgagg aggagaacuu cuaccagcag cagcagcaga gcgagcugca gcccccggcg      540
cccagcgagg auaucuggaa gaaauucgag cugcugccca ccccgccccu guccccuagc      600
cgccgcuccg ggcucugcuc gcccuccuac guugcgguca cacccuucuc ccuucgggga      660
gacaacgacg gcgguggcgg gagcuucucc acggccgacc agcuggagau ggugaccgag      720
cugcugggag gagacauggu gaaccagagu uucaucugcg acccggacga cgagaccuuc      780
aucaaaaaca ucaucaucca ggacuguaug uggagcggcu ucucggccgc cgccaagcuc      840
gucucagaga agcuggccuc cuaccaggcu gcgcgcaaag acagcggcag cccgaacccc      900
gcccgcggcc acagcgucug cuccaccucc agcuuguacc ugcaggaucu gagcgccgcc      960
gccucagagu gcaucgaccc cucggugguc uuccccuacc cucucaacga cagcagcucg     1020
cccaaguccu gcgccucgca agacuccagc gccuucucuc cgccucggaa uucucugcuc     1080
uccucgacgg aguccuccc gcagggcagc cccgagcccc uggugcucca ugaggagaca     1140
ccgcccacca ccagcagcga cucugaggag gaacaagaag augaggaaga aaucgauguu     1200
guuucugugg aaaagaggca ggcuccuggc aaaaggucag agucuggauc accuucugcu     1260
ggaggccaca gcaaaccucc ucacagccca cugguccuca agaggugcca cgucuccaca     1320
caucagcaca acuacgcagc gccucccucc acucggaagg acuauccugc ugccaagagg     1380
gucaaguugg acagugucag aguccugaga cagaucagca caaccgaaa augcaccagc      1440 cccagguccu cggacaccga ggagaauguc aagaggcgaa cacacaacgu cuuggagcgc     1500
cagaggagga acgagcuaaa acggagcuuu uuugcccugc gugaccagau cccggaguug     1560
gaaaacaaug aaaaggcccc caagguaguu auccuuaaaa aagccacagc auacauccug     1620
uccguccaag cagaggagca aaagcucauu ucugaagagg acuuguugcg gaaacgacga     1680
gaacaguuga aacacaaacu ugaacagcua cggaacucuu gugcguaagg aaaaguaagg     1740
aaaacgauuc cuucuaacag aaauguccug agcaaucacc uaugaacuug uuucaaaugc     1800
augaucaaau gcaaccucac aaccuuggcu gagucuugag acugaaagau uuagccauaa     1860
uguaaacugc cucaaauugg acuuugggca uaaaagaacu uuuuuaugcu uaccaucuuu     1920
uuuuuuucuu uaacagauuu guauuuaaga auuguuuuua aaaaauuuua agauuuacac     1980
aauguuucuc uguaaauauu gccauuaaau guaaauaacu uuaauaaaac guuuauagca     2040
guuacacaga auuucaaucc uaguauauag uaccuaguau uauagguacu auaaacccua     2100
auuuuuuuua uuuaaguaca uuuugcuuuu uaaaguugau uuuuuucuau uguuuuuaga     2160
aaaaauaaaa uaacuggcaa auauaucauu gagccaaauc uuaaguugug aauguuuugu     2220
uucguuucuu ccccucccca accaccacca ucccuguuug uuuucaucaa uugccccuuc     2280 agagggguggu cuuaagaaag gcaagaguuu uccucuguug aaaugggucu ggggggccuua     2340 aggucuuuaa guucuuggag guucuaagau gcuuccugga gacuaugaua acagccagag     2400
uugacaguua gaaggaaugg cagaaggcag gugagaaggu gagagguagg caaaggagau     2460
acaagagguc aaagguagca guuaaguaca caaagaggca uaggacuggg gaguuggga      2520 ggaaggugag gaagaaacuc cuguuacuuu aguuaaccag ugccaguccc cugcucacuc     2580
caaacccagg aauucugccc aguugauggg gacacggugg gaaccagcuu cugcugccuu     2640
cacaaccagg cgccaguccu guccauggu uaucucgcaa accccagagg aucucuggga      2700
ggaaugcuac uauuaacccu auuucacaaa caaggaaaua gaagagcuca aagagguuau     2760
```

-continued

```
guaacuuauc uguagccacg cagauaaauac aaagcagcaa ucuggaccca uucuguucaa    2820
aacacuuaac ccuucgcuau caugccuugg uucaucuggg ucuaaugugc ugagaucaag    2880
aagguuuagg accuaaugga cagacucaag ucauaacaau gcuaagcucu auuuguguc    2940 caagcacucc uaagcauuuu auccuaacu cuacaucaac cccaugaagg agauacuguu    3000
gauuucccca uauuagaagu agagagggaa gcugaggcac acaaagacuc auccacaugc    3060
ccaagauuca cugauaggga aaaguggaag cgagauuuga acccaggcug uuuacuccua    3120
accuguccaa gccaccucuc agacgacggu aggaaucagc uggcugcuug ugaguacagg    3180
aguuacaguc cagugggua uguuuuuuaa gucucaacau cuaagccugg ucaggcauca    3240 guucccuuu uuuugugauu uauuuuguuu uuauuuuguu guucauuguu uaauuuuucc    3300
uuuuacaaug agaaggucac caucuugacu ccuaccuuag ccauuuguug aaucagacuc    3360
augacggcuc cuggggaagaa gccaguucag aucauaaaau aaaacauauu uauucuuugu    3420
caugggaguc auuauuuuag aaacuacaaa cucuccuugc uuccauccuu uuuuacauac    3480
ucaugacaca ugcucauccu gaguccuuga aaagguauuu uugaacaugu guauuaauua    3540
uaagccucug aaaaccuaug gcccaaacca gaaaugaugu ugauuauaua gguaaaugaa    3600
ggaugcuauu gcuguucuaa uuaccucauu gucucagucu caaaguaggu cuucagcucc    3660 cguguacuuug ggauuuuaau cuaccaccac ccauaaauca auaaauaauu acuuucuuug    3720
a    3721
```

<210> SEQ ID NO 203
<211> LENGTH: 2923
<212> TYPE: RNA
<213> ORGANISM: Homo sapiens
<220> FEATURE:
<221> NAME/KEY: misc_feature
<222> LOCATION: (1)..(2923)
<223> OTHER INFORMATION: MYCN RNA sequence

<400> SEQUENCE: 203

```
aggcugugac agucaucugu cuggacgcgc uggguggaug cgggggggcuc cugggaacug      60 uguuggagcc gagcaagcgc uagccaggcg caagcgcgca cagacuguag ccauccgagg     120 acaccccgc cccccccggcc cacccggaga cacccgcgca gaaucgccuc cggaucccu     180 gcagucggcg ggagguaagg agcagggcuu gcaaaccgcc cggcgcccag ggaagcgacg     240
agcgccgggg caaggcaagc ccuggacggg auugcgacgu gcgcaccggg cgcccuaaua     300
ugcccggggg acuguuucug cuuccgaaac aaaaccaucu cuggguuuc ccagaaaagc     360 caguuccagc cccgaaggca uccuggcuag aggagacccg cccuaauccu uuugcagccc     420
uuaccggggg gaguaauggc uucugcgaaa agaaauuccc ucggcucuag aagaucuguc     480
uguguuugag cugucggaga gccguguugg aggucggcgc cggcccccgc cuuccgcgcc     540
ccccacggga aggaagcacc cccgguauua aaacgaacgg ggcggaaaga agcccucagu     600
cgccggccgg gaggcgagcc gaugccgagc ugcuccacgu ccaccaugcc gggcaugauc     660
ugcaagaacc cagaccucga guuugacucg cuacagcccu gcuucuaccc ggacgaagau     720
gacuucuacu ucggcggccc cgacucgacc ccccgggggg aggacaucug gaagaaguuu     780
gagcugcugc ccacgccccc gcugucgccc agccguggcu ucgcgagca cagcuccgag     840 cccccgagcu gggucacgga gaugcugcuu gagaacgagc uguggggcag cccggccgag     900
gaggacgcgu ucggccuggg gggacuggu ggccucaccc ccaacccggu cauccuccag     960
```

-continued

```
gacugcaugu ggagcggcuu cuccgcccgc gagaagcugg agcgcgccgu gagcgagaag     1020
cugcagcacg gccgcgggcc gccaaccgcc gguuccaccg cccagucccc gggagccggc     1080
gccgccagcc cugcggbucg cgggcacggc ggggcugcgg gagccggccg cgccgggggcc    1140 gcccugcccg ccgagcucgc ccacccggcc gccgagugcg uggaucccgc cguggucuuc     1200
cccuuucccg ugaacaagcg cgagccagcg cccgugcccg cagccccggc cagugccccg     1260 gcggcggggcc cugcggucgc cucgggggcg gguauugccg ccccagccgg ggccccgggg    1320
gucgccccuc cgcgcccagg cggccgccag accagcggcg gcgaccacaa ggcccucagu     1380
accuccggag aggacacccu gagcgauuca gaugaugaag augaugaaga ggaagaugaa     1440
gaggaagaaa ucgacguggu cacuguggag aagcggcguu ccuccuccaa caccaaggcu     1500
gucaccacau ucaccaucac ugugcgucco aagaacgcag cccugggucc cgggagggcu     1560
caguccagcg agcugauccu caaacgaugc cuucccaucc accagcagca caacuaugcc     1620
gcccccucuc ccuacgugga gagugaggau gcacccccac agaagaagau aaagagcgag     1680 gcgucccco guccgcucaa gagugucauc cccccaaagg cuaagagcuu gagccccgca     1740 aacucgacu cggaggacag ugagcgucgc agaaaccaca acauccugga gcgccagcgc      1800
cgcaacgacc uucggucccag cuuucucacg cucagggacc acgugccgga guugguaaag    1860
aaugagaagg ccgccaaggu ggucauuuug aaaaaggcca cugaguaugu ccacucccuc     1920
caggccgagg agcaccagcu uuugcuggaa aaggaaaaau ugcaggcaag acagcagcag     1980
uugcuaaaga aaauugaaca cgcucggacu ugcuagacgc uucucaaaac uggacaguca    2040
cugccacuuu gcacauuuug auuuuuuuuu uaaacaaaca uuguguugac auuaagaaug    2100
uugguuuacu uucaaaucgg uccccugucg aguucggcuc uggguggca guaggaccac     2160 caguguggg uucugcuggg accuuggaga gccugcaucc caggaugcug gguggcccug     2220
cagccuccuc caccucaccu ccaugacagc gcuaaacguu ggugacgguu gggagccucu     2280
ggggcuguug aagucaccuu gugguguucca aguuuccaaa caacagaaag ucauuccuuc    2340
uuuuuaaaau ggugcuuaag uuccagcaga ugccacauaa ggggguuugcc auuugauacc    2400 ccugggggaac auuucuguaa auaccauuga cacauccgcc uuuuguauac auccugggua    2460
augagaggug gcuuuugcgg ccaguauuag acuggaaguu cauaccuaag uacuguaaua    2520
auaccucaau guuugaggag cauguuuugu auacaaauau auuguuaauc ucuguuaugu    2580
acuguacuaa uucuuacacu gccuguauac uuuaguauga cgcugauaca uaacuaaauu    2640
ugauacuuau auuuucguau gaaaaugagu gugaaaguu uugaguagau auuacuuuau     2700
cacuuuuuga acuaagaaac uuuuguaaag aaauuuacua uauauauaug ccuuuuuccu    2760
agccuguuuc uuccuguuaa uguauuuguu cauguuuggu gcauagaacu ggguaaaugc    2820
aaaguucugu guuuaauuuc uucaaaaugu auauauuuag ugcugcaucu uauagcacuu     2880
ugaaauaccu cauguuuaug aaaauaaaua gcuuaaaauu aaa                       2923
```

<210> SEQ ID NO 204
<211> LENGTH: 21
<212> TYPE: DNA
<213> ORGANISM: Artificial Sequence
<220> FEATURE:
<223> OTHER INFORMATION: ACTB forward primer

<400> SEQUENCE: 204
cctggcattg ccgacaggat g                                               21

```
<210> SEQ ID NO 205
<211> LENGTH: 23
<212> TYPE: DNA
<213> ORGANISM: Artificial Sequence
<220> FEATURE:
<223> OTHER INFORMATION: ACTB reverse primer

<400> SEQUENCE: 205
ccgatccaca cggagtactt gcg                                                   23

<210> SEQ ID NO 206
<211> LENGTH: 20
<212> TYPE: DNA
<213> ORGANISM: Artificial Sequence
<220> FEATURE:
<223> OTHER INFORMATION: lnc-HLX-2-7 forward primer

<400> SEQUENCE: 206
gcttctctgg cacatggact                                                       20

<210> SEQ ID NO 207
<211> LENGTH: 20
<212> TYPE: DNA
<213> ORGANISM: Artificial Sequence
<220> FEATURE:
<223> OTHER INFORMATION: lnc-HLX-2-7 reverse primer

<400> SEQUENCE: 207
gtccttcgtg agcacagcat                                                       20

<210> SEQ ID NO 208
<211> LENGTH: 20
<212> TYPE: DNA
<213> ORGANISM: Artificial Sequence
<220> FEATURE:
<223> OTHER INFORMATION: HLX forward primer

<400> SEQUENCE: 208
gcttctctgg cacatggact                                                       20

<210> SEQ ID NO 209
<211> LENGTH: 20
<212> TYPE: DNA
<213> ORGANISM: Artificial Sequence
<220> FEATURE:
<223> OTHER INFORMATION: HLX reverse primer

<400> SEQUENCE: 209
gtccttcgtg agcacagcat                                                       20

<210> SEQ ID NO 210
<211> LENGTH: 20
<212> TYPE: DNA
<213> ORGANISM: Artificial Sequence
<220> FEATURE:
<223> OTHER INFORMATION: MYC forward primer

<400> SEQUENCE: 210
aaaggccccc aaggtagtta                                                       20

<210> SEQ ID NO 211
<211> LENGTH: 20
<212> TYPE: DNA
<213> ORGANISM: Artificial Sequence
<220> FEATURE:
<223> OTHER INFORMATION: MYC reverse primer
```

-continued

```
<400> SEQUENCE: 211
gcacaagagt tccgtagctg                                                    20

<210> SEQ ID NO 212
<211> LENGTH: 20
<212> TYPE: DNA
<213> ORGANISM: Artificial Sequence
<220> FEATURE:
<223> OTHER INFORMATION: MYCN forward primer

<400> SEQUENCE: 212
ctaatactgg ccgcaaaagc                                                    20

<210> SEQ ID NO 213
<211> LENGTH: 20
<212> TYPE: DNA
<213> ORGANISM: Artificial Sequence
<220> FEATURE:
<223> OTHER INFORMATION: MYCN reverse primer

<400> SEQUENCE: 213
cataaggggt ttgccatttg                                                    20

<210> SEQ ID NO 214
<211> LENGTH: 24
<212> TYPE: DNA
<213> ORGANISM: Artificial Sequence
<220> FEATURE:
<223> OTHER INFORMATION: PTGR1 forward primer

<400> SEQUENCE: 214
cagacacaat accactgtct ttgg                                               24

<210> SEQ ID NO 215
<211> LENGTH: 24
<212> TYPE: DNA
<213> ORGANISM: Artificial Sequence
<220> FEATURE:
<223> OTHER INFORMATION: PTGR1 reverse primer

<400> SEQUENCE: 215
ctgcattaac catcactgtt tctc                                               24

<210> SEQ ID NO 216
<211> LENGTH: 21
<212> TYPE: DNA
<213> ORGANISM: Artificial Sequence
<220> FEATURE:
<223> OTHER INFORMATION: FZD6 forward primer

<400> SEQUENCE: 216
agactctctg gggaacaggt c                                                  21

<210> SEQ ID NO 217
<211> LENGTH: 25
<212> TYPE: DNA
<213> ORGANISM: Artificial Sequence
<220> FEATURE:
<223> OTHER INFORMATION: FZD6 reverse primer

<400> SEQUENCE: 217
ggccagtgtc agtaatatca ctctt                                              25

<210> SEQ ID NO 218
<211> LENGTH: 25
```

-continued

```
<212> TYPE: DNA
<213> ORGANISM: Artificial Sequence
<220> FEATURE:
<223> OTHER INFORMATION: TRPM3 forward primer

<400> SEQUENCE: 218
aatacttcag agaaaaggat gatcg                                                    25

<210> SEQ ID NO 219
<211> LENGTH: 23
<212> TYPE: DNA
<213> ORGANISM: Artificial Sequence
<220> FEATURE:
<223> OTHER INFORMATION: TRPM3 reverse primer

<400> SEQUENCE: 219
gagtgctctc tctcgttgac ttc                                                      23

<210> SEQ ID NO 220
<211> LENGTH: 25
<212> TYPE: DNA
<213> ORGANISM: Artificial Sequence
<220> FEATURE:
<223> OTHER INFORMATION: NAMPT forward primer

<400> SEQUENCE: 220
aaaagggccg attatcttta catag                                                    25

<210> SEQ ID NO 221
<211> LENGTH: 25
<212> TYPE: DNA
<213> ORGANISM: Artificial Sequence
<220> FEATURE:
<223> OTHER INFORMATION: NAMPT reverse primer

<400> SEQUENCE: 221
ccattcttga agacagtatg gagaa                                                    25

<210> SEQ ID NO 222
<211> LENGTH: 19
<212> TYPE: DNA
<213> ORGANISM: Artificial Sequence
<220> FEATURE:
<223> OTHER INFORMATION: NRBP2 forward primer

<400> SEQUENCE: 222
aggacgagag cgacatcct                                                           19

<210> SEQ ID NO 223
<211> LENGTH: 21
<212> TYPE: DNA
<213> ORGANISM: Artificial Sequence
<220> FEATURE:
<223> OTHER INFORMATION: NRBP2 reverse primer

<400> SEQUENCE: 223
ggctaggaag gtgctctgaa g                                                        21

<210> SEQ ID NO 224
<211> LENGTH: 25
<212> TYPE: DNA
<213> ORGANISM: Artificial Sequence
<220> FEATURE:
<223> OTHER INFORMATION: NBAT1 forward primer

<400> SEQUENCE: 224
```

-continued gtttatccat cttcagctcc actct                                           25

<210> SEQ ID NO 225
<211> LENGTH: 23
<212> TYPE: DNA
<213> ORGANISM: Artificial Sequence
<220> FEATURE:
<223> OTHER INFORMATION: NBAT1 reverse primer

<400> SEQUENCE: 225
tctgtgggtt tcagtttctt cat                                             23

<210> SEQ ID NO 226
<211> LENGTH: 26
<212> TYPE: DNA
<213> ORGANISM: Artificial Sequence
<220> FEATURE:
<223> OTHER INFORMATION: CCNG2 forward primer

<400> SEQUENCE: 226
caacagctac tatagtgttc ctgagc                                          26

<210> SEQ ID NO 227
<211> LENGTH: 25
<212> TYPE: DNA
<213> ORGANISM: Artificial Sequence
<220> FEATURE:
<223> OTHER INFORMATION: CCNG2 reverse primer

<400> SEQUENCE: 227
tctcctctcc acaactcata tcttc                                           25

<210> SEQ ID NO 228
<211> LENGTH: 25
<212> TYPE: DNA
<213> ORGANISM: Artificial Sequence
<220> FEATURE:
<223> OTHER INFORMATION: ELK4 forward primer

<400> SEQUENCE: 228
gcaagaacaa gcctaacatg aatta                                           25

<210> SEQ ID NO 229
<211> LENGTH: 25
<212> TYPE: DNA
<213> ORGANISM: Artificial Sequence
<220> FEATURE:
<223> OTHER INFORMATION: ELK4 reverse primer

<400> SEQUENCE: 229
acacaaactt ctgaccattc acttt                                           25

<210> SEQ ID NO 230
<211> LENGTH: 25
<212> TYPE: DNA
<213> ORGANISM: Artificial Sequence
<220> FEATURE:
<223> OTHER INFORMATION: CDKN2C forward primer

<400> SEQUENCE: 230
ttgcaaaata atgtaaacgt caatg                                           25

<210> SEQ ID NO 231
<211> LENGTH: 25
<212> TYPE: DNA
<213> ORGANISM: Artificial Sequence -continued
<220> FEATURE:
<223> OTHER INFORMATION: CDKN2C reverse primer

<400> SEQUENCE: 231
ttagcacctc taagtagcag tctcc                                              25

<210> SEQ ID NO 232
<211> LENGTH: 25
<212> TYPE: DNA
<213> ORGANISM: Artificial Sequence
<220> FEATURE:
<223> OTHER INFORMATION: CDK6 forward primer

<400> SEQUENCE: 232
caaccaattg agaagtttgt aacag                                              25

<210> SEQ ID NO 233
<211> LENGTH: 24
<212> TYPE: DNA
<213> ORGANISM: Artificial Sequence
<220> FEATURE:
<223> OTHER INFORMATION: CDK6 reverse primer

<400> SEQUENCE: 233
ggcactgtag gcagatattc tttt                                               24

<210> SEQ ID NO 234
<211> LENGTH: 25
<212> TYPE: DNA
<213> ORGANISM: Artificial Sequence
<220> FEATURE:
<223> OTHER INFORMATION: HLX-2KB forward primer

<400> SEQUENCE: 234
ttatttctta agagagaggg tgagg                                              25

<210> SEQ ID NO 235
<211> LENGTH: 25
<212> TYPE: DNA
<213> ORGANISM: Artificial Sequence
<220> FEATURE:
<223> OTHER INFORMATION: HLX-2KB reverse primer

<400> SEQUENCE: 235
aatttgactg caaacattta gacct                                             25

<210> SEQ ID NO 236
<211> LENGTH: 23
<212> TYPE: DNA
<213> ORGANISM: Artificial Sequence
<220> FEATURE:
<223> OTHER INFORMATION: HLX-TSS forward primer

<400> SEQUENCE: 236
tacgcagagt agcaagaagc act                                                23

<210> SEQ ID NO 237
<211> LENGTH: 21
<212> TYPE: DNA
<213> ORGANISM: Artificial Sequence
<220> FEATURE:
<223> OTHER INFORMATION: HLX-TSS reverse primer

<400> SEQUENCE: 237
tggaggggaa ttaggaacaa g                                                  21

-continued

```
<210> SEQ ID NO 238
<211> LENGTH: 25
<212> TYPE: DNA
<213> ORGANISM: Artificial Sequence
<220> FEATURE:
<223> OTHER INFORMATION: E-box forward primer

<400> SEQUENCE: 238
taataaacaa aaccgcctag atgag                                             25

<210> SEQ ID NO 239
<211> LENGTH: 25
<212> TYPE: DNA
<213> ORGANISM: Artificial Sequence
<220> FEATURE:
<223> OTHER INFORMATION: E-box reverse primer

<400> SEQUENCE: 239
aaaggcttta cataaatcgg cttac                                             25

<210> SEQ ID NO 240
<211> LENGTH: 21
<212> TYPE: DNA
<213> ORGANISM: Artificial Sequence
<220> FEATURE:
<223> OTHER INFORMATION: Antisense oligonucleotide targeting lnc-HLX-2-7
<220> FEATURE:
<221> NAME/KEY: misc_feature
<222> LOCATION: (1)..(20)
<223> OTHER INFORMATION: Phosphorothioate linkages

<400> SEQUENCE: 240
tgagagatta atctagattg c                                                 21

<210> SEQ ID NO 241
<211> LENGTH: 21
<212> TYPE: DNA
<213> ORGANISM: Artificial Sequence
<220> FEATURE:
<223> OTHER INFORMATION: control antisense olignucleotide targeting
      luciferase
<220> FEATURE:
<221> NAME/KEY: misc_feature
<222> LOCATION: (1)..(20)
<223> OTHER INFORMATION: Phosphorotioate linkages

<400> SEQUENCE: 241
tcgaagtact cagcgtaagt t                                                 21
```